US006803366B2

(12) United States Patent
Kawamura et al.

(10) Patent No.: US 6,803,366 B2
(45) Date of Patent: Oct. 12, 2004

(54) AGENT FOR IMPROVING LEARNING OR MEMORY

(75) Inventors: Kuniaki Kawamura, Kamakura (JP); Hiroshi Nagase, Kamakura (JP); Noriyuki Hirano, Yokohama (JP); Junzo Kamei, Yokohama (JP)

(73) Assignee: Toray Industries, Inc., Tokyo (JP)

( * ) Notice: Subject to any disclaimer, the term of this patent is extended or adjusted under 35 U.S.C. 154(b) by 66 days.

(21) Appl. No.: 10/148,489

(22) PCT Filed: Nov. 30, 2000

(86) PCT No.: PCT/JP00/08447

§ 371 (c)(1),
(2), (4) Date: May 30, 2002

(87) PCT Pub. No.: WO01/40226

PCT Pub. Date: Jun. 7, 2001

(65) Prior Publication Data

US 2003/0186986 A1 Oct. 2, 2003

(30) Foreign Application Priority Data

Nov. 30, 1999 (JP) .......................................... 11-339191

(51) Int. Cl.$^7$ ................. A61K 31/4375; A61K 31/4985

(52) U.S. Cl. ........................................ 514/250; 514/287

(58) Field of Search ................................. 514/250, 287

(56) References Cited

FOREIGN PATENT DOCUMENTS

| | | |
|---|---|---|
| JP | 4-257288 A | 9/1992 |
| WO | WO 93-01186 | 1/1993 |
| WO | 99/02157 A1 | 1/1999 |

OTHER PUBLICATIONS

Freeman et al., Brain Res., vol. 864, No. 2, pp. 230–239 (2000).

Pavone et al., Peptides, vol. 11, No. 3, pp. 591–594 (1990).

*Primary Examiner*—Richard L. Raymond
(74) *Attorney, Agent, or Firm*—Birch, Stewart, Kolasch & Birch, LLP

(57) ABSTRACT

Disclosed is an agent for improving learning and/or memory, which is useful for therapy of dementia accompanying disorder of memory due to a cerebrovascular disease, neurodegenerative disease such as Alzheimer's disease, endocrine disease, nutritional or metabolic disorder, infectious disease, drug addiction or the like. The agent for improving learning and/or memory according to the present invention comprises as an effective ingredient an isoquinoline derivative having a specific structure, such as (4aR, 12aR)-2-methyl-4a-(3-hydroxyphenyl)-1,2,3,4,4a,5,12,12a-octahydro-quinoline[2,3-g]isoquinoline or a pharmaceutically acceptable salt thereof.

2 Claims, 3 Drawing Sheets

AGENT FOR IMPROVING LEARNING OR MEMORY

This application is the national phase under 35 U.S.C. §371 of PCT International Application No. PCT/JP00/08847 which has an International filing date of Nov. 30, 2000, which designated the United States of America.

TECHNICAL FIELD

The present invention relates to an agent for improving learning and/or memory comprising as an effective ingredient a quinolinoisoquinoline derivative or a pharmaceutically acceptable acid addition salt thereof.

BACKGROUND ART

Learning means to acquire change in behavior, which continues for a relatively long time, which is caused by experience or practice, or the process for acquiring the change in behavior. Memory means to retain information for a certain time, which information is obtained through experience, and to retrieve the information as required. However, the definitions of these two concepts are not simple, and are not independent for each other but most of them overlap. Therefore, learning ability and mneme are often measured by similar experiments in the field of behavioral pharmacology.

Learning includes the steps of encoding, storage, recognition and retrieval. Even if one of these steps is inhibited, disorder of memory occurs (Seiden, L. S. & Dykstra, L. A., Psychopharmacology, a biochemical and behavioral approach. Van Nostrand Reinhold Co., New York(1077)). A representative disease accompanying memory disorder and/or learning disability is dementia. The term "dementia" means the continuous state in which the intellectual ability is reduced, which intellectual ability had ever developed to the normal level. Symptoms of dementia include, in addition to memory disorder and/or learning disability, mood disorder, emotional disorder, intellectual disturbance and psychomotor disturbance. Improvement of memory disorder which likely to cause serious problems in social life is an indispensable action of anti-dementia drugs.

In the brains of patients suffering from senile dementia or Alzheimer's disease, remarkable reduction in neurotransmitters and biosynthesis enzymes thereof is observed. Therefore, therapy by drugs such as dopamine, noradrenalin, serotonin, acetylcholine and GABA, which act on the transmission process through neurotransmitters is drawing attention. Since it is known that the hypofunction of acetylcholine system is prominent in brains of patients suffering from dementia, the current mainstream of development of therapeutic method for dementia is the development of drugs targeting the activation of acetylcholine nervous system. An anti-dementia drug, tacrine, which has obtained approval, is an acetylcholinesterase inhibitor, and it has been confirmed that improvement of intellectual function to a certain degree is observed in about half of the cases in which the drug is administered. However, this drug has a problem in the hepatic toxicity and choline-related side effects. With Aricept effective for Alzheimer's disease through the similar mechanism, improvement is observed in about half cases for patients suffering from the dementia in light to medium degree.

On the other hand, references disclosing quinolinoisoquinoline derivatives include Japanese Laid-open Patent Application (Kokai) No. 4-275288, WO93/01186 and WO99/02157. These patent literatures disclose the uses of the derivatives as immunosuppressive agents, analgesics and antitussives. However, these references are totally silent about improvement of learning or memory.

DISCLOSURE OF THE INVENTION

The present inventors intensively studied to discover that specific isoquinoline derivatives exhibit excellent effect for improving learning and/or memory, thereby completing the present invention.

That is, the present invention provides an agent for improving learning and/or memory comprising as an effective ingredient an isoquinoline derivative of the Formula (I):

(I)

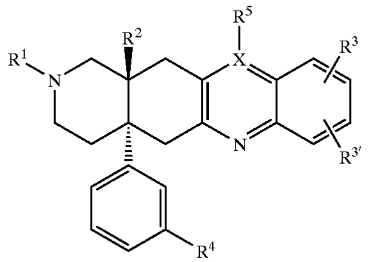

{wherein $R^1$ represents hydrogen, $C_1$–$C_5$ alkyl, $C_4$–$C_7$ cycloalkylalkyl, $C_5$–$C_7$ cycloalkenylalkyl, $C_7$–$C_{14}$ aralkyl, $C_4$–$C_5$ transalkenyl, allyl, furanyl-2-ylalkyl, thienyl-2-ylalkyl, $C_1$–$C_5$ alkanoyl, benzoyl, vinyloxycarbonyl, trichloroethoxycarbonyl, benzyloxycarbonyl or $C_8$–$C_{14}$ arylalkanoyl; $R^2$ represents hydrogen or $OR^6$ (wherein $R^6$ represents hydrogen, $C_1$–$C_5$ alkyl or $C_1$–$C_5$ alkanoyl); $R^3$ and $R^{3'}$ independently represent $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino, or $C_1$–$C_3$ alkylamino; $R^4$ represents hydrogen, hydroxy, $C_1$–$C_3$ alkoxy, benzyl, or $C_1$–$C_5$ alkanoyl or halogen; X represents nitrogen or carbon; $R^5$ exists only when X is carbon, and represents $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino} or a pharmaceutically acceptable salt thereof. The present invention also provides a use of said isoquinoline derivative represented by the above-described Formula (I) or the pharmaceutically acceptable salt thereof for the preparation of an agent for improving learning and/or memory. The present invention further provides a method for improving learning and/or memory comprising administering an effective amount of the isoquinoline derivative represented by the above-described Formula (I) or the pharmaceutically acceptable salt thereof.

By the present invention, an agent for improving learning and/or memory was provided, which is useful for therapy of dementia accompanying memory disorder due to a cerebrovascular disease, neurodegenerative disease such as Alzheimer's disease, endocrine disease, nutritional or metabolic disorder, infectious disease, drug addiction or the like.

BEST MODE FOR CARRYING OUT THE INVENTION

Figure 1:
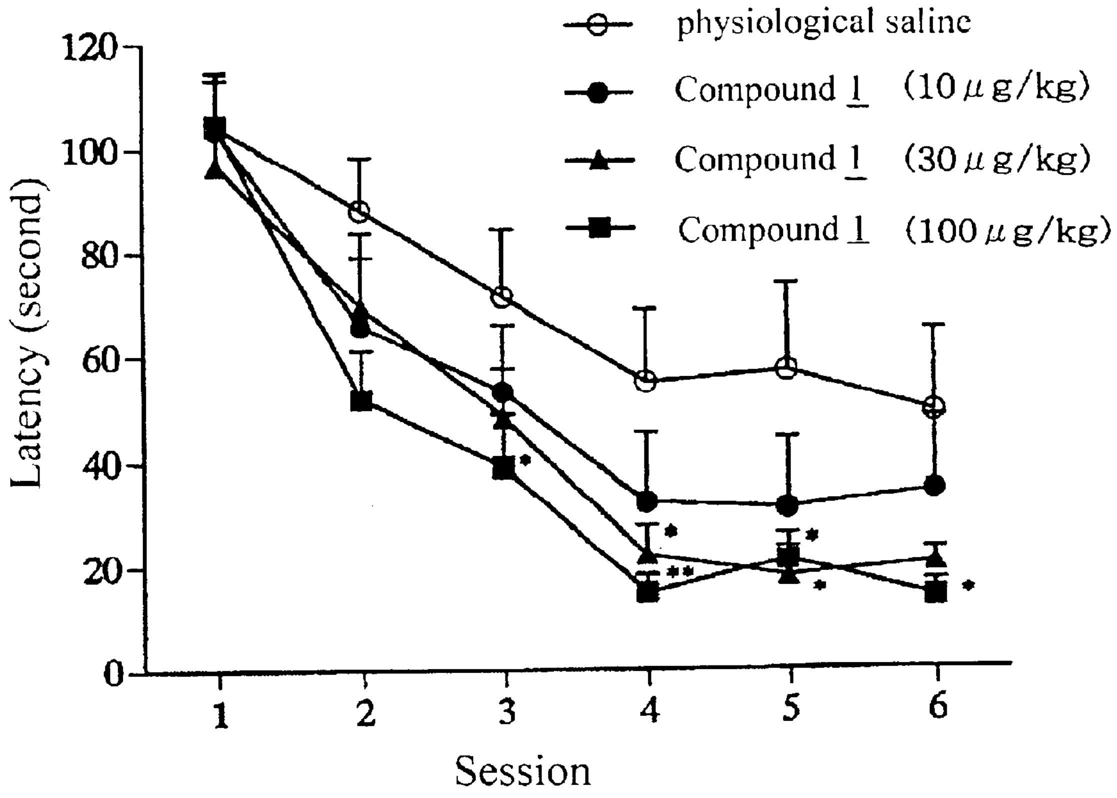
FIG. 1 shows the learning process of the rats to which Compound 1 that is the agent for improving learning and/or memory according to the present invention, in comparison with the learning process of the rats to which saline was administered.

Preferred modes of the agent for improving learning and/or memory comprising the isoquinoline derivative of the Formula (I) or a pharmaceutically acceptable acid addition salt thereof, according to the present invention, are as follows:

$R^1$ is preferably hydrogen, $C_1$–$C_5$ alkyl, $C_4$–$C_7$ cycloalkylalkyl, $C_5$–$C_7$ cycloalkenylalkyl, $C_7$–$C_{14}$ aralkyl, $C_4$–$C_5$ transalkenyl, allyl, furanyl-2-ylalkyl, thienyl-2-ylalkyl, $C_1$–$C_5$ alkanoyl, benzoyl, vinyloxycarbonyl, trichloroethoxycarbonyl, benzyloxycarbonyl or $C_8$–$C_{14}$ arylalkanoyl, and especially preferably hydrogen, methyl, ethyl, cyclopropylmethyl, allyl, phenethyl, furan-2-ylethyl or thiophene-2-ylethyl.

$R^2$ is preferably hydrogen or $OR^6$ (wherein $R^6$ represents hydrogen, $C_1$–$C_5$ alkyl or $C_1$–$C_5$ alkanoyl), especially preferably hydrogen, hydroxy, methoxy or ethoxy.

$R^3$ and $R^{3'}$ independently are preferably $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino, and especially preferably are methyl, hydrogen, chlorine, fluorine, bromine, iodine, hydroxy, methoxy, nitro, amino or dimethylamino.

$R^4$ is preferably hydrogen, hydroxy, $C_1$–$C_3$ alkoxy, benzyl, $C_1$–$C_5$ alkanoyl or halogen, and especially preferably hydrogen, hydroxy or methoxy.

X represents nitrogen or carbon. $R^5$ exists only when X is carbon, and is preferably $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino, and especially preferably methyl, hydrogen, chlorine, fluorine, bromine, iodine, hydroxy, methoxy, nitro, amino or dimethylamino. Needless to say, the compounds of the present invention are not restricted to those mentioned above.

Formula (I) represents relative configuration of the compounds and includes racemic compound and optically active compounds of which absolute structures are represented by the following Formulae (A) and (B). Among these, the optically active compounds represented by the following Formulae (A) are preferred.

(A)

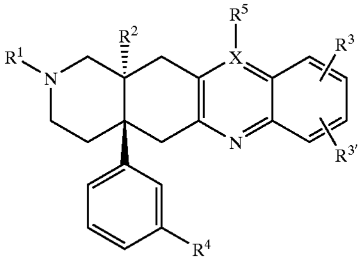

(B)

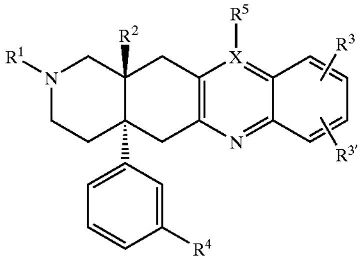

Examples of preferred pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid, hydrobromic acid, phosphoric acid salt, tartaric acid salt, methanesulfonic acid salt and the like are especially preferred, but the pharmaceutically acceptable salts are not restricted to those mentioned above.

The compounds used in the present invention also include the novel compounds represented by Formula (II) below.

(II)

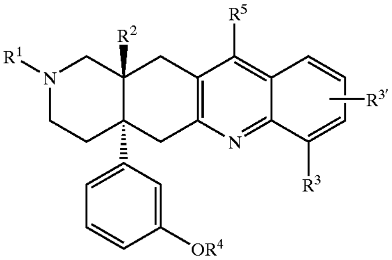

{(A) wherein $R^1$ represents hydrogen, $C_1$–$C_5$ alkyl, $C_4$–$C_7$ cycloalkylalkyl, $C_5$–$C_7$ cycloalkenylalkyl, $C_7$–$C_{14}$ aralkyl, $C_4$–$C_5$ transalkenyl, allyl, furanyl-2-ylalkyl, thienyl-2-ylalkyl, $C_1$–$C_5$ alkanoyl, benzoyl, vinyloxycarbonyl, trichloroethoxycarbonyl, benzyloxycarbonyl or $C_8$–$C_{14}$ arylalkanoyl; $R^2$ represents hydrogen or $OR^6$ (wherein $R^6$ represents hydrogen, $C_1$–$C_5$ alkyl or $C_1$–$C_5$ alkanoyl); $R^3$ and $R^{3'}$ independently represent $C_1$–$C_5$ alkyl, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino; $R^4$ represents hydrogen or $C_1$–$C_3$ alkyl; $R^5$ represents $C_1$–$C_5$ alkyl, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino; or (B) wherein $R^1$ represents hydrogen, thienyl-2-ylalkyl, $C_1$–$C_5$ alkanoyl, benzoyl, vinyloxycarbonyl, trichloroethoxycarbonyl, benzyloxycarbonyl or $C_8$–$C_{14}$ arylalkanoyl; $R^2$ represents hydrogen or $OR^6$ (wherein $R^6$ represents hydrogen, $C_1$–$C_5$ alkyl or $C_1$–$C_5$ alkanoyl); $R^3$ and $R^{3'}$ independently represent $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino; $R^4$ represents hydrogen or $C_1$–$C_3$ alkyl; and $R^5$ represents $C_1$–$C_5$ alkyl, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino}.

Specific examples of the compounds represented by Formula (II) are shown in Tables 1 to 52.

TABLE 1

| Compound No. | R1 | R2 | R3 | R3' | R4 | R5 |
|---|---|---|---|---|---|---|
| 1 | Me | H | Cl | 5-Cl | H | Me |
| 2 | Me | H | Cl | 5-Cl | H | NH2 |
| 3 | Me | H | Cl | 5-Cl | H | OH |
| 4 | Me | H | Cl | 5-Cl | Me | Me |
| 5 | Me | H | Cl | 5-Cl | Me | NH2 |
| 6 | Me | H | Cl | 5-Cl | Me | OH |
| 7 | Me | H | Cl | 6-Cl | H | Me |
| 8 | Me | H | Cl | 6-Cl | H | NH2 |
| 9 | Me | H | Cl | 6-Cl | H | OH |
| 10 | Me | H | Cl | 6-Cl | Me | Me |
| 11 | Me | H | Cl | 6-Cl | Me | NH2 |
| 12 | Me | H | Cl | 6-Cl | Me | OH |
| 13 | Me | H | Cl | 7-Cl | H | Me |
| 14 | Me | H | Cl | 7-Cl | H | NH2 |
| 15 | Me | H | Cl | 7-Cl | H | OH |
| 16 | Me | H | Cl | 7-Cl | Me | Me |
| 17 | Me | H | Cl | 7-Cl | Me | NH2 |
| 18 | Me | H | Cl | 7-Cl | Me | OH |
| 19 | Me | H | Cl | 5-NH2 | H | Me |
| 20 | Me | H | Cl | 5-NH2 | H | NH2 |
| 21 | Me | H | Cl | 5-NH2 | H | OH |
| 22 | Me | H | Cl | 5-NH2 | Me | Me |
| 23 | Me | H | Cl | 5-NH2 | Me | NH2 |
| 24 | Me | H | Cl | 5-NH2 | Me | OH |
| 25 | Me | H | Cl | 6-NH2 | H | Me |
| 26 | Me | H | Cl | 6-NH2 | H | NH2 |
| 27 | Me | H | Cl | 6-NH2 | H | OH |
| 28 | Me | H | Cl | 6-NH2 | Me | Me |
| 29 | Me | H | Cl | 6-NH2 | Me | NH2 |
| 30 | Me | H | Cl | 6-NH2 | Me | OH |
| 31 | Me | H | Cl | 7-NH2 | H | Me |
| 32 | Me | H | Cl | 7-NH2 | H | NH2 |
| 33 | Me | H | Cl | 7-NH2 | H | OH |
| 34 | Me | H | Cl | 7-NH2 | Me | Me |
| 35 | Me | H | Cl | 7-NH2 | Me | NH2 |
| 36 | Me | H | Cl | 7-NH2 | Me | OH |
| 37 | Me | H | Cl | 5-Me | H | Me |
| 38 | Me | H | Cl | 5-Me | H | NH2 |
| 39 | Me | H | Cl | 5-Me | H | OH |
| 40 | Me | H | Cl | 5-Me | Me | Me |

TABLE 2

| Compound No. | R1 | R2 | R3 | R3' | R4 | R5 |
|---|---|---|---|---|---|---|
| 41 | Me | H | Cl | 5-Me | Me | NH2 |
| 42 | Me | H | Cl | 5-Me | Me | OH |
| 43 | Me | H | Cl | 6-Me | H | Me |
| 44 | Me | H | Cl | 6-Me | H | NH2 |
| 45 | Me | H | Cl | 6-Me | H | OH |
| 46 | Me | H | Cl | 6-Me | Me | Me |

TABLE 2-continued

| Compound No. | R1 | R2 | R3 | R3' | R4 | R5 |
|---|---|---|---|---|---|---|
| 47 | Me | H | Cl | 6-Me | Me | NH2 |
| 48 | Me | H | Cl | 6-Me | Me | OH |
| 49 | Me | H | Cl | 7-Me | H | Me |
| 50 | Me | H | Cl | 7-Me | H | NH2 |
| 51 | Me | H | Cl | 7-Me | H | OH |
| 52 | Me | H | Cl | 7-Me | Me | Me |
| 53 | Me | H | Cl | 7-Me | Me | NH2 |
| 54 | Me | H | Cl | 7-Me | Me | OH |
| 55 | Me | H | NH2 | 5-Cl | H | Me |
| 56 | Me | H | NH2 | 5-Cl | H | NH2 |
| 57 | Me | H | NH2 | 5-Cl | H | OH |
| 58 | Me | H | NH2 | 5-Cl | Me | Me |
| 59 | Me | H | NH2 | 5-Cl | Me | NH2 |
| 60 | Me | H | NH2 | 5-Cl | Me | OH |
| 61 | Me | H | NH2 | 6-Cl | H | Me |
| 62 | Me | H | NH2 | 6-Cl | H | NH2 |
| 63 | Me | H | NH2 | 6-Cl | H | OH |
| 64 | Me | H | NH2 | 6-Cl | Me | Me |
| 65 | Me | H | NH2 | 6-Cl | Me | NH2 |
| 66 | Me | H | NH2 | 6-Cl | Me | OH |
| 67 | Me | H | NH2 | 7-Cl | H | Me |
| 68 | Me | H | NH2 | 7-Cl | H | NH2 |
| 69 | Me | H | NH2 | 7-Cl | H | OH |
| 70 | Me | H | NH2 | 7-Cl | Me | Me |
| 71 | Me | H | NH2 | 7-Cl | Me | NH2 |
| 72 | Me | H | NH2 | 7-Cl | Me | OH |
| 73 | Me | H | NH2 | 5-NH2 | H | Me |
| 74 | Me | H | NH2 | 5-NH2 | H | NH2 |
| 75 | Me | H | NH2 | 5-NH2 | H | OH |
| 76 | Me | H | NH2 | 5-NH2 | Me | Me |
| 77 | Me | H | NH2 | 5-NH2 | Me | NH2 |
| 78 | Me | H | NH2 | 5-NH2 | Me | OH |
| 79 | Me | H | NH2 | 6-NH2 | H | Me |
| 80 | Me | H | NH2 | 6-NH2 | H | NH2 |

TABLE 3

| Compound No. | R1 | R2 | R3 | R3' | R4 | R5 |
|---|---|---|---|---|---|---|
| 81 | Me | H | NH2 | 6-NH2 | H | OH |
| 82 | Me | H | NH2 | 6-NH2 | Me | Me |
| 83 | Me | H | NH2 | 6-NH2 | Me | NH2 |
| 84 | Me | H | NH2 | 6-NH2 | Me | OH |
| 85 | Me | H | NH2 | 7-NH2 | H | Me |
| 86 | Me | H | NH2 | 7-NH2 | H | NH2 |
| 87 | Me | H | NH2 | 7-NH2 | H | OH |
| 88 | Me | H | NH2 | 7-NH2 | Me | Me |
| 89 | Me | H | NH2 | 7-NH2 | Me | NH2 |
| 90 | Me | H | NH2 | 7-NH2 | Me | OH |
| 91 | Me | H | NH2 | 5-Me | H | Me |
| 92 | Me | H | NH2 | 5-Me | H | NH2 |
| 93 | Me | H | NH2 | 5-Me | H | OH |
| 94 | Me | H | NH2 | 5-Me | Me | Me |
| 95 | Me | H | NH2 | 5-Me | Me | NH2 |
| 96 | Me | H | NH2 | 5-Me | Me | OH |
| 97 | Me | H | NH2 | 6-Me | H | Me |
| 98 | Me | H | NH2 | 6-Me | H | NH2 |
| 99 | Me | H | NH2 | 6-Me | H | OH |
| 100 | Me | H | NH2 | 6-Me | Me | Me |
| 101 | Me | H | NH2 | 6-Me | Me | NH2 |
| 102 | Me | H | NH2 | 6-Me | Me | OH |
| 103 | Me | H | NH2 | 7-Me | H | Me |
| 104 | Me | H | NH2 | 7-Me | H | NH2 |
| 105 | Me | H | NH2 | 7-Me | H | OH |
| 106 | Me | H | NH2 | 7-Me | Me | Me |
| 107 | Me | H | NH2 | 7-Me | Me | NH2 |
| 108 | Me | H | NH2 | 7-Me | Me | OH |
| 109 | Me | H | Me | 5-Cl | H | Me |
| 110 | Me | H | Me | 5-Cl | H | NH2 |
| 111 | Me | H | Me | 5-Cl | H | OH |
| 112 | Me | H | Me | 5-Cl | Me | Me |
| 113 | Me | H | Me | 5-Cl | Me | NH2 |
| 114 | Me | H | Me | 5-Cl | Me | OH |
| 115 | Me | H | Me | 6-Cl | H | Me |

TABLE 3-continued

| Compound No. | R1 | R2 | R3 | R3' | R4 | R5 |
|---|---|---|---|---|---|---|
| 116 | Me | H | Me | 6-Cl | H | NH2 |
| 117 | Me | H | Me | 6-Cl | H | OH |
| 118 | Me | H | Me | 6-Cl | Me | Me |
| 119 | Me | H | Me | 6-Cl | Me | NH2 |
| 120 | Me | H | Me | 6-Cl | Me | OH |

TABLE 4

| Compound No. | R1 | R2 | R3 | R3' | R4 | R5 |
|---|---|---|---|---|---|---|
| 121 | Me | H | Me | 7-Cl | H | Me |
| 122 | Me | H | Me | 7-Cl | H | NH2 |
| 123 | Me | H | Me | 7-Cl | H | OH |
| 124 | Me | H | Me | 7-Cl | Me | Me |
| 125 | Me | H | Me | 7-Cl | Me | NH2 |
| 126 | Me | H | Me | 7-Cl | Me | OH |
| 127 | Me | H | Me | 5-NH2 | H | Me |
| 128 | Me | H | Me | 5-NH2 | H | NH2 |
| 129 | Me | H | Me | 5-NH2 | H | OH |
| 130 | Me | H | Me | 5-NH2 | Me | Me |
| 131 | Me | H | Me | 5-NH2 | Me | NH2 |
| 132 | Me | H | Me | 5-NH2 | Me | OH |
| 133 | Me | H | Me | 6-NH2 | H | Me |
| 134 | Me | H | Me | 6-NH2 | H | NH2 |
| 135 | Me | H | Me | 6-NH2 | H | OH |
| 136 | Me | H | Me | 6-NH2 | Me | Me |
| 137 | Me | H | Me | 6-NH2 | Me | NH2 |
| 138 | Me | H | Me | 6-NH2 | Me | OH |
| 139 | Me | H | Me | 7-NH2 | H | Me |
| 140 | Me | H | Me | 7-NH2 | H | NH2 |
| 141 | Me | H | Me | 7-NH2 | H | OH |
| 142 | Me | H | Me | 7-NH2 | Me | Me |
| 143 | Me | H | Me | 7-NH2 | Me | NH2 |
| 144 | Me | H | Me | 7-NH2 | Me | OH |
| 145 | Me | H | Me | 5-Me | H | Me |
| 146 | Me | H | Me | 5-Me | H | NH2 |
| 147 | Me | H | Me | 5-Me | H | OH |
| 148 | Me | H | Me | 5-Me | Me | Me |
| 149 | Me | H | Me | 5-Me | Me | NH2 |
| 150 | Me | H | Me | 5-Me | Me | OH |
| 151 | Me | H | Me | 6-Me | H | Me |
| 152 | Me | H | Me | 6-Me | H | NH2 |
| 153 | Me | H | Me | 6-Me | H | OH |
| 154 | Me | H | Me | 6-Me | Me | Me |
| 155 | Me | H | Me | 6-Me | Me | NH2 |
| 156 | Me | H | Me | 6-Me | Me | OH |
| 157 | Me | H | Me | 7-Me | H | Me |
| 158 | Me | H | Me | 7-Me | H | NH2 |
| 159 | Me | H | Me | 7-Me | H | OH |
| 160 | Me | H | Me | 7-Me | Me | Me |

TABLE 5

| Compound No. | R1 | R2 | R3 | R3' | R4 | R5 |
|---|---|---|---|---|---|---|
| 161 | Me | H | Me | 7-Me | Me | NH2 |
| 162 | Me | H | Me | 7-Me | Me | OH |
| 163 | Me | OH | Cl | 5-Cl | H | Me |
| 164 | Me | OH | Cl | 5-Cl | H | NH2 |
| 165 | Me | OH | Cl | 5-Cl | H | OH |
| 166 | Me | OH | Cl | 5-Cl | Me | Me |
| 167 | Me | OH | Cl | 5-Cl | Me | NH2 |
| 168 | Me | OH | Cl | 5-Cl | Me | OH |
| 169 | Me | OH | Cl | 6-Cl | H | Me |
| 170 | Me | OH | Cl | 6-Cl | H | NH2 |
| 171 | Me | OH | Cl | 6-Cl | H | OH |
| 172 | Me | OH | Cl | 6-Cl | Me | Me |
| 173 | Me | OH | Cl | 6-Cl | Me | NH2 |
| 174 | Me | OH | Cl | 6-Cl | Me | OH |
| 175 | Me | OH | Cl | 7-Cl | H | Me |
| 176 | Me | OH | Cl | 7-Cl | H | NH2 |
| 177 | Me | OH | Cl | 7-Cl | H | OH |

TABLE 5-continued

| Compound No. | R1 | R2 | R3 | R3' | R4 | R5 |
|---|---|---|---|---|---|---|
| 178 | Me | OH | Cl | 7-Cl | Me | Me |
| 179 | Me | OH | Cl | 7-Cl | Me | NH2 |
| 180 | Me | OH | Cl | 7-Cl | Me | OH |
| 181 | Me | OH | Cl | 5-NH2 | H | Me |
| 182 | Me | OH | Cl | 5-NH2 | H | NH2 |
| 183 | Me | OH | Cl | 5-NH2 | H | OH |
| 184 | Me | OH | Cl | 5-NH2 | Me | Me |
| 185 | Me | OH | Cl | 5-NH2 | Me | NH2 |
| 186 | Me | OH | Cl | 5-NH2 | Me | OH |
| 187 | Me | OH | Cl | 6-NH2 | H | Me |
| 188 | Me | OH | Cl | 6-NH2 | H | NH2 |
| 189 | Me | OH | Cl | 6-NH2 | H | OH |
| 190 | Me | OH | Cl | 6-NH2 | Me | Me |
| 191 | Me | OH | Cl | 6-NH2 | Me | NH2 |
| 192 | Me | OH | Cl | 6-NH2 | Me | OH |
| 193 | Me | OH | Cl | 7-NH2 | H | Me |
| 194 | Me | OH | Cl | 7-NH2 | H | NH2 |
| 195 | Me | OH | Cl | 7-NH2 | H | OH |
| 196 | Me | OH | Cl | 7-NH2 | Me | Me |
| 197 | Me | OH | Cl | 7-NH2 | Me | NH2 |
| 198 | Me | OH | Cl | 7-NH2 | Me | OH |
| 199 | Me | OH | Cl | 5-Me | H | Me |
| 200 | Me | OH | Cl | 5-Me | H | NH2 |

TABLE 6

| Compound No. | R1 | R2 | R3 | R3' | R4 | R5 |
|---|---|---|---|---|---|---|
| 201 | Me | OH | Cl | 5-Me | H | OH |
| 202 | Me | OH | Cl | 5-Me | Me | Me |
| 203 | Me | OH | Cl | 5-Me | Me | NH2 |
| 204 | Me | OH | Cl | 5-Me | Me | OH |
| 205 | Me | OH | Cl | 6-Me | H | Me |
| 206 | Me | OH | Cl | 6-Me | H | NH2 |
| 207 | Me | OH | Cl | 6-Me | H | OH |
| 208 | Me | OH | Cl | 6-Me | Me | Me |
| 209 | Me | OH | Cl | 6-Me | Me | NH2 |
| 210 | Me | OH | Cl | 6-Me | Me | OH |
| 211 | Me | OH | Cl | 7-Me | H | Me |
| 212 | Me | OH | Cl | 7-Me | H | NH2 |
| 213 | Me | OH | Cl | 7-Me | H | OH |
| 214 | Me | OH | Cl | 7-Me | Me | Me |
| 215 | Me | OH | Cl | 7-Me | Me | NH2 |
| 216 | Me | OH | Cl | 7-Me | Me | OH |
| 217 | Me | OH | NH2 | 5-Cl | H | Me |
| 218 | Me | OH | NH2 | 5-Cl | H | NH2 |
| 219 | Me | OH | NH2 | 5-Cl | H | OH |
| 220 | Me | OH | NH2 | 5-Cl | Me | Me |
| 221 | Me | OH | NH2 | 5-Cl | Me | NH2 |
| 222 | Me | OH | NH2 | 5-Cl | Me | OH |
| 223 | Me | OH | NH2 | 6-Cl | H | Me |
| 224 | Me | OH | NH2 | 6-Cl | H | NH2 |
| 225 | Me | OH | NH2 | 6-Cl | H | OH |
| 226 | Me | OH | NH2 | 6-Cl | Me | Me |
| 227 | Me | OH | NH2 | 6-Cl | Me | NH2 |
| 228 | Me | OH | NH2 | 6-Cl | Me | OH |
| 229 | Me | OH | NH2 | 7-Cl | H | Me |
| 230 | Me | OH | NH2 | 7-Cl | H | NH2 |
| 231 | Me | OH | NH2 | 7-Cl | H | OH |
| 232 | Me | OH | NH2 | 7-Cl | Me | Me |
| 233 | Me | OH | NH2 | 7-Cl | Me | NH2 |
| 234 | Me | OH | NH2 | 7-Cl | Me | OH |
| 235 | Me | OH | NH2 | 5-NH2 | H | Me |
| 236 | Me | OH | NH2 | 5-NH2 | H | NH2 |
| 237 | Me | OH | NH2 | 5-NH2 | H | OH |
| 238 | Me | OH | NH2 | 5-NH2 | Me | Me |
| 239 | Me | OH | NH2 | 5-NH2 | Me | NH2 |
| 240 | Me | OH | NH2 | 5-NH2 | Me | OH |

TABLE 7

| Compound No. | R1 | R2 | R3 | R3' | R4 | R5 |
|---|---|---|---|---|---|---|
| 241 | Me | OH | NH2 | 6-NH2 | H | Me |
| 242 | Me | OH | NH2 | 6-NH2 | H | NH2 |
| 243 | Me | OH | NH2 | 6-NH2 | H | OH |
| 244 | Me | OH | NH2 | 6-NH2 | Me | Me |
| 245 | Me | OH | NH2 | 6-NH2 | Me | NH2 |
| 246 | Me | OH | NH2 | 6-NH2 | Me | OH |
| 247 | Me | OH | NH2 | 7-NH2 | H | Me |
| 248 | Me | OH | NH2 | 7-NH2 | H | NH2 |
| 249 | Me | OH | NH2 | 7-NH2 | H | OH |
| 250 | Me | OH | NH2 | 7-NH2 | Me | Me |
| 251 | Me | OH | NH2 | 7-NH2 | Me | NH2 |
| 252 | Me | OH | NH2 | 7-NH2 | Me | OH |
| 253 | Me | OH | NH2 | 5-Me | H | Me |
| 254 | Me | OH | NH2 | 5-Me | H | NH2 |
| 255 | Me | OH | NH2 | 5-Me | H | OH |
| 256 | Me | OH | NH2 | 5-Me | Me | Me |
| 257 | Me | OH | NH2 | 5-Me | Me | NH2 |
| 258 | Me | OH | NH2 | 5-Me | Me | OH |
| 259 | Me | OH | NH2 | 6-Me | H | Me |
| 260 | Me | OH | NH2 | 6-Me | H | NH2 |
| 261 | Me | OH | NH2 | 6-Me | H | OH |
| 262 | Me | OH | NH2 | 6-Me | Me | Me |
| 263 | Me | OH | NH2 | 6-Me | Me | NH2 |
| 264 | Me | OH | NH2 | 6-Me | Me | OH |
| 265 | Me | OH | NH2 | 7-Me | H | Me |
| 266 | Me | OH | NH2 | 7-Me | H | NH2 |
| 267 | Me | OH | NH2 | 7-Me | H | OH |
| 268 | Me | OH | NH2 | 7-Me | Me | Me |
| 269 | Me | OH | NH2 | 7-Me | Me | NH2 |
| 270 | Me | OH | NH2 | 7-Me | Me | OH |
| 271 | Me | OH | Me | 5-Cl | H | Me |
| 272 | Me | OH | Me | 5-Cl | H | NH2 |
| 273 | Me | OH | Me | 5-Cl | H | OH |
| 274 | Me | OH | Me | 5-Cl | Me | Me |
| 275 | Me | OH | Me | 5-Cl | Me | NH2 |
| 276 | Me | OH | Me | 5-Cl | Me | OH |
| 277 | Me | OH | Me | 6-Cl | H | Me |
| 278 | Me | OH | Me | 6-Cl | H | NH2 |
| 279 | Me | OH | Me | 6-Cl | H | OH |
| 280 | Me | OH | Me | 6-Cl | Me | Me |

TABLE 8

| Compound No. | R1 | R2 | R3 | R3' | R4 | R5 |
|---|---|---|---|---|---|---|
| 281 | Me | OH | Me | 6-Cl | Me | NH2 |
| 282 | Me | OH | Me | 6-Cl | Me | OH |
| 283 | Me | OH | Me | 7-Cl | H | Me |
| 284 | Me | OH | Me | 7-Cl | H | NH2 |
| 285 | Me | OH | Me | 7-Cl | H | OH |
| 286 | Me | OH | Me | 7-Cl | Me | Me |
| 287 | Me | OH | Me | 7-Cl | Me | NH2 |
| 288 | Me | OH | Me | 7-Cl | Me | OH |
| 289 | Me | OH | Me | 5-NH2 | H | Me |
| 290 | Me | OH | Me | 5-NH2 | H | NH2 |
| 291 | Me | OH | Me | 5-NH2 | H | OH |
| 292 | Me | OH | Me | 5-NH2 | Me | Me |
| 293 | Me | OH | Me | 5-NH2 | Me | NH2 |
| 294 | Me | OH | Me | 5-NH2 | Me | OH |
| 295 | Me | OH | Me | 6-NH2 | H | Me |
| 296 | Me | OH | Me | 6-NH2 | H | NH2 |
| 297 | Me | OH | Me | 6-NH2 | H | OH |
| 298 | Me | OH | Me | 6-NH2 | Me | Me |
| 299 | Me | OH | Me | 6-NH2 | Me | NH2 |
| 300 | Me | OH | Me | 6-NH2 | Me | OH |
| 301 | Me | OH | Me | 7-NH2 | H | Me |
| 302 | Me | OH | Me | 7-NH2 | H | NH2 |
| 303 | Me | OH | Me | 7-NH2 | H | OH |
| 304 | Me | OH | Me | 7-NH2 | Me | Me |
| 305 | Me | OH | Me | 7-NH2 | Me | NH2 |
| 306 | Me | OH | Me | 7-NH2 | Me | OH |
| 307 | Me | OH | Me | 5-Me | H | Me |
| 308 | Me | OH | Me | 5-Me | H | NH2 |
| 309 | Me | OH | Me | 5-Me | H | OH |

TABLE 8-continued

| Compound No. | R1 | R2 | R3 | R3' | R4 | R5 |
|---|---|---|---|---|---|---|
| 310 | Me | OH | Me | 5-Me | Me | Me |
| 311 | Me | OH | Me | 5-Me | Me | NH2 |
| 312 | Me | OH | Me | 5-Me | Me | OH |
| 313 | Me | OH | Me | 6-Me | H | Me |
| 314 | Me | OH | Me | 6-Me | H | NH2 |
| 315 | Me | OH | Me | 6-Me | H | OH |
| 316 | Me | OH | Me | 6-Me | Me | Me |
| 317 | Me | OH | Me | 6-Me | Me | NH2 |
| 318 | Me | OH | Me | 6-Me | Me | OH |
| 319 | Me | OH | Me | 7-Me | H | Me |
| 320 | Me | OH | Me | 7-Me | H | NH2 |

TABLE 9

| Compound No. | R1 | R2 | R3 | R3' | R4 | R5 |
|---|---|---|---|---|---|---|
| 321 | Me | OH | Me | 7-Me | H | OH |
| 322 | Me | OH | Me | 7-Me | Me | Me |
| 323 | Me | OH | Me | 7-Me | Me | NH2 |
| 324 | Me | OH | Me | 7-Me | Me | OH |
| 325 | Me | OMe | Cl | 5-Cl | H | Me |
| 326 | Me | OMe | Cl | 5-Cl | H | NH2 |
| 327 | Me | OMe | Cl | 5-Cl | H | OH |
| 328 | Me | OMe | Cl | 5-Cl | Me | Me |
| 329 | Me | OMe | Cl | 5-Cl | Me | NH2 |
| 330 | Me | OMe | Cl | 5-Cl | Me | OH |
| 331 | Me | OMe | Cl | 6-Cl | H | Me |
| 332 | Me | OMe | Cl | 6-Cl | H | NH2 |
| 333 | Me | OMe | Cl | 6-Cl | H | OH |
| 334 | Me | OMe | Cl | 6-Cl | Me | Me |
| 335 | Me | OMe | Cl | 6-Cl | Me | NH2 |
| 336 | Me | OMe | Cl | 6-Cl | Me | OH |
| 337 | Me | OMe | Cl | 7-Cl | H | Me |
| 338 | Me | OMe | Cl | 7-Cl | H | NH2 |
| 339 | Me | OMe | Cl | 7-Cl | H | OH |
| 340 | Me | OMe | Cl | 7-Cl | Me | Me |
| 341 | Me | OMe | Cl | 7-Cl | Me | NH2 |
| 342 | Me | OMe | Cl | 7-Cl | Me | OH |
| 343 | Me | OMe | Cl | 5-NH2 | H | Me |
| 344 | Me | OMe | Cl | 5-NH2 | H | NH2 |
| 345 | Me | OMe | Cl | 5-NH2 | H | OH |
| 346 | Me | OMe | Cl | 5-NH2 | Me | Me |
| 347 | Me | OMe | Cl | 5-NH2 | Me | NH2 |
| 348 | Me | OMe | Cl | 5-NH2 | Me | OH |
| 349 | Me | OMe | Cl | 6-NH2 | H | Me |
| 350 | Me | OMe | Cl | 6-NH2 | H | NH2 |
| 351 | Me | OMe | Cl | 6-NH2 | H | OH |
| 352 | Me | OMe | Cl | 6-NH2 | Me | Me |
| 353 | Me | OMe | Cl | 6-NH2 | Me | NH2 |
| 354 | Me | OMe | Cl | 6-NH2 | Me | OH |
| 355 | Me | OMe | Cl | 7-NH2 | H | Me |
| 356 | Me | OMe | Cl | 7-NH2 | H | NH2 |
| 357 | Me | OMe | Cl | 7-NH2 | H | OH |
| 358 | Me | OMe | Cl | 7-NH2 | Me | Me |
| 359 | Me | OMe | Cl | 7-NH2 | Me | NH2 |
| 360 | Me | OMe | Cl | 7-NH2 | Me | OH |

TABLE 10

| Compound No. | R1 | R2 | R3 | R3' | R4 | R5 |
|---|---|---|---|---|---|---|
| 361 | Me | OMe | Cl | 5-Me | H | Me |
| 362 | Me | OMe | Cl | 5-Me | H | NH2 |
| 363 | Me | OMe | Cl | 5-Me | H | OH |
| 364 | Me | OMe | Cl | 5-Me | Me | Me |
| 365 | Me | OMe | Cl | 5-Me | Me | NH2 |
| 366 | Me | OMe | Cl | 5-Me | Me | OH |
| 367 | Me | OMe | Cl | 6-Me | H | Me |
| 368 | Me | OMe | Cl | 6-Me | H | NH2 |
| 369 | Me | OMe | Cl | 6-Me | H | OH |
| 370 | Me | OMe | Cl | 6-Me | Me | Me |
| 371 | Me | OMe | Cl | 6-Me | Me | NH2 |

TABLE 10-continued

| Compound No. | R1 | R2 | R3 | R3' | R4 | R5 |
|---|---|---|---|---|---|---|
| 372 | Me | OMe | Cl | 6-Me | Me | OH |
| 373 | Me | OMe | Cl | 7-Me | H | Me |
| 374 | Me | OMe | Cl | 7-Me | H | NH2 |
| 375 | Me | OMe | Cl | 7-Me | H | OH |
| 376 | Me | OMe | Cl | 7-Me | Me | Me |
| 377 | Me | OMe | Cl | 7-Me | Me | NH2 |
| 378 | Me | OMe | Cl | 7-Me | Me | OH |
| 379 | Me | OMe | NH2 | 5-Cl | H | Me |
| 380 | Me | OMe | NH2 | 5-Cl | H | NH2 |
| 381 | Me | OMe | NH2 | 5-Cl | H | OH |
| 382 | Me | OMe | NH2 | 5-Cl | Me | Me |
| 383 | Me | OMe | NH2 | 5-Cl | Me | NH2 |
| 384 | Me | OMe | NH2 | 5-Cl | Me | OH |
| 385 | Me | OMe | NH2 | 6-Cl | H | Me |
| 386 | Me | OMe | NH2 | 6-Cl | H | NH2 |
| 387 | Me | OMe | NH2 | 6-Cl | H | OH |
| 388 | Me | OMe | NH2 | 6-Cl | Me | Me |
| 389 | Me | OMe | NH2 | 6-Cl | Me | NH2 |
| 390 | Me | OMe | NH2 | 6-Cl | Me | OH |
| 391 | Me | OMe | NH2 | 7-Cl | H | Me |
| 392 | Me | OMe | NH2 | 7-Cl | H | NH2 |
| 393 | Me | OMe | NH2 | 7-Cl | H | OH |
| 394 | Me | OMe | NH2 | 7-Cl | Me | Me |
| 395 | Me | OMe | NH2 | 7-Cl | Me | NH2 |
| 396 | Me | OMe | NH2 | 7-Cl | Me | OH |
| 397 | Me | OMe | NH2 | 5-NH2 | H | Me |
| 398 | Me | OMe | NH2 | 5-NH2 | H | NH2 |
| 399 | Me | OMe | NH2 | 5-NH2 | H | OH |
| 400 | Me | OMe | NH2 | 5-NH2 | Me | Me |

TABLE 11

| Compound No. | R1 | R2 | R3 | R3' | R4 | R5 |
|---|---|---|---|---|---|---|
| 401 | Me | OMe | NH2 | 5-NH2 | Me | NH2 |
| 402 | Me | OMe | NH2 | 5-NH2 | Me | OH |
| 403 | Me | OMe | NH2 | 6-NH2 | H | Me |
| 404 | Me | OMe | NH2 | 6-NH2 | H | NH2 |
| 405 | Me | OMe | NH2 | 6-NH2 | H | OH |
| 406 | Me | OMe | NH2 | 6-NH2 | Me | Me |
| 407 | Me | OMe | NH2 | 6-NH2 | Me | NH2 |
| 408 | Me | OMe | NH2 | 6-NH2 | Me | OH |
| 409 | Me | OMe | NH2 | 7-NH2 | H | Me |
| 410 | Me | OMe | NH2 | 7-NH2 | H | NH2 |
| 411 | Me | OMe | NH2 | 7-NH2 | H | OH |
| 412 | Me | OMe | NH2 | 7-NH2 | Me | Me |
| 413 | Me | OMe | NH2 | 7-NH2 | Me | NH2 |
| 414 | Me | OMe | NH2 | 7-NH2 | Me | OH |
| 415 | Me | OMe | NH2 | 5-Me | H | Me |
| 416 | Me | OMe | NH2 | 5-Me | H | NH2 |
| 417 | Me | OMe | NH2 | 5-Me | H | OH |
| 418 | Me | OMe | NH2 | 5-Me | Me | Me |
| 419 | Me | OMe | NH2 | 5-Me | Me | NH2 |
| 420 | Me | OMe | NH2 | 5-Me | Me | OH |
| 421 | Me | OMe | NH2 | 6-Me | H | Me |
| 422 | Me | OMe | NH2 | 6-Me | H | NH2 |
| 423 | Me | OMe | NH2 | 6-Me | H | OH |
| 424 | Me | OMe | NH2 | 6-Me | Me | Me |
| 425 | Me | OMe | NH2 | 6-Me | Me | NH2 |
| 426 | Me | OMe | NH2 | 6-Me | Me | OH |
| 427 | Me | OMe | NH2 | 7-Me | H | Me |
| 428 | Me | OMe | NH2 | 7-Me | H | NH2 |
| 429 | Me | OMe | NH2 | 7-Me | H | OH |
| 430 | Me | OMe | NH2 | 7-Me | Me | Me |
| 431 | Me | OMe | NH2 | 7-Me | Me | NH2 |
| 432 | Me | OMe | NH2 | 7-Me | Me | OH |
| 433 | Me | OMe | Me | 5-Cl | H | Me |
| 434 | Me | OMe | Me | 5-Cl | H | NH2 |
| 435 | Me | OMe | Me | 5-Cl | H | OH |
| 436 | Me | OMe | Me | 5-Cl | Me | Me |
| 437 | Me | OMe | Me | 5-Cl | Me | NH2 |
| 438 | Me | OMe | Me | 5-Cl | Me | OH |

TABLE 11-continued

| Compound No. | R1 | R2 | R3 | R3' | R4 | R5 |
|---|---|---|---|---|---|---|
| 439 | Me | OMe | Me | 6-Cl | H | Me |
| 440 | Me | OMe | Me | 6-Cl | H | NH2 |

TABLE 12

| Compound No. | R1 | R2 | R3 | R3' | R4 | R5 |
|---|---|---|---|---|---|---|
| 441 | Me | OMe | Me | 6-Cl | H | OH |
| 442 | Me | OMe | Me | 6-Cl | Me | Me |
| 443 | Me | OMe | Me | 6-Cl | Me | NH2 |
| 444 | Me | OMe | Me | 6-Cl | Me | OH |
| 445 | Me | OMe | Me | 7-Cl | H | Me |
| 446 | Me | OMe | Me | 7-Cl | H | NH2 |
| 447 | Me | OMe | Me | 7-Cl | H | OH |
| 448 | Me | OMe | Me | 7-Cl | Me | Me |
| 449 | Me | OMe | Me | 7-Cl | Me | NH2 |
| 450 | Me | OMe | Me | 7-Cl | Me | OH |
| 451 | Me | OMe | Me | 5-NH2 | H | Me |
| 452 | Me | OMe | Me | 5-NH2 | H | NH2 |
| 453 | Me | OMe | Me | 5-NH2 | H | OH |
| 454 | Me | OMe | Me | 5-NH2 | Me | Me |
| 455 | Me | OMe | Me | 5-NH2 | Me | NH2 |
| 456 | Me | OMe | Me | 5-NH2 | Me | OH |
| 457 | Me | OMe | Me | 6-NH2 | H | Me |
| 458 | Me | OMe | Me | 6-NH2 | H | NH2 |
| 459 | Me | OMe | Me | 6-NH2 | H | OH |
| 460 | Me | OMe | Me | 6-NH2 | Me | Me |
| 461 | Me | OMe | Me | 6-NH2 | Me | NH2 |
| 462 | Me | OMe | Me | 6-NH2 | Me | OH |
| 463 | Me | OMe | Me | 7-NH2 | H | Me |
| 464 | Me | OMe | Me | 7-NH2 | H | NH2 |
| 465 | Me | OMe | Me | 7-NH2 | H | OH |
| 466 | Me | OMe | Me | 7-NH2 | Me | Me |
| 467 | Me | OMe | Me | 7-NH2 | Me | NH2 |
| 468 | Me | OMe | Me | 7-NH2 | Me | OH |
| 469 | Me | OMe | Me | 5-Me | H | Me |
| 470 | Me | OMe | Me | 5-Me | H | NH2 |
| 471 | Me | OMe | Me | 5-Me | H | OH |
| 472 | Me | OMe | Me | 5-Me | Me | Me |
| 473 | Me | OMe | Me | 5-Me | Me | NH2 |
| 474 | Me | OMe | Me | 5-Me | Me | OH |
| 475 | Me | OMe | Me | 6-Me | H | Me |
| 476 | Me | OMe | Me | 6-Me | H | NH2 |
| 477 | Me | OMe | Me | 6-Me | H | OH |
| 478 | Me | OMe | Me | 6-Me | Me | Me |
| 479 | Me | OMe | Me | 6-Me | Me | NH2 |
| 480 | Me | OMe | Me | 6-Me | Me | OH |

TABLE 13

| Compound No. | R1 | R2 | R3 | R3' | R4 | R5 |
|---|---|---|---|---|---|---|
| 481 | Me | OMe | Me | 7-Me | H | Me |
| 482 | Me | OMe | Me | 7-Me | H | NH2 |
| 483 | Me | OMe | Me | 7-Me | H | OH |
| 484 | Me | OMe | Me | 7-Me | Me | Me |
| 485 | Me | OMe | Me | 7-Me | Me | NH2 |
| 486 | Me | OMe | Me | 7-Me | Me | OH |
| 487 | CH2CH2Ph | H | Cl | 5-Cl | H | Me |
| 488 | CH2CH2Ph | H | Cl | 5-Cl | H | NH2 |
| 489 | CH2CH2Ph | H | Cl | 5-Cl | H | OH |
| 490 | CH2CH2Ph | H | Cl | 5-Cl | Me | Me |
| 491 | CH2CH2Ph | H | Cl | 5-Cl | Me | NH2 |
| 492 | CH2CH2Ph | H | Cl | 5-Cl | Me | OH |
| 493 | CH2CH2Ph | H | Cl | 6-Cl | H | Me |
| 494 | CH2CH2Ph | H | Cl | 6-Cl | H | NH2 |
| 495 | CH2CH2Ph | H | Cl | 6-Cl | H | OH |
| 496 | CH2CH2Ph | H | Cl | 6-Cl | Me | Me |
| 497 | CH2CH2Ph | H | Cl | 6-Cl | Me | NH2 |
| 498 | CH2CH2Ph | H | Cl | 6-Cl | Me | OH |
| 499 | CH2CH2Ph | H | Cl | 7-Cl | H | Me |
| 500 | CH2CH2Ph | H | Cl | 7-Cl | H | NH2 |

TABLE 13-continued

| Compound No. | R1 | R2 | R3 | R3' | R4 | R5 |
|---|---|---|---|---|---|---|
| 501 | CH2CH2Ph | H | Cl | 7-Cl | H | OH |
| 502 | CH2CH2Ph | H | Cl | 7-Cl | Me | Me |
| 503 | CH2CH2Ph | H | Cl | 7-Cl | Me | NH2 |
| 504 | CH2CH2Ph | H | Cl | 7-Cl | Me | OH |
| 505 | CH2CH2Ph | H | Cl | 5-NH2 | H | Me |
| 506 | CH2CH2Ph | H | Cl | 5-NH2 | H | NH2 |
| 507 | CH2CH2Ph | H | Cl | 5-NH2 | H | OH |
| 508 | CH2CH2Ph | H | Cl | 5-NH2 | Me | Me |
| 509 | CH2CH2Ph | H | Cl | 5-NH2 | Me | NH2 |
| 510 | CH2CH2Ph | H | Cl | 5-NH2 | Me | OH |
| 511 | CH2CH2Ph | H | Cl | 6-NH2 | H | Me |
| 512 | CH2CH2Ph | H | Cl | 6-NH2 | H | NH2 |
| 513 | CH2CH2Ph | H | Cl | 6-NH2 | H | OH |
| 514 | CH2CH2Ph | H | Cl | 6-NH2 | Me | Me |
| 515 | CH2CH2Ph | H | Cl | 6-NH2 | Me | NH2 |
| 516 | CH2CH2Ph | H | Cl | 6-NH2 | Me | OH |
| 517 | CH2CH2Ph | H | Cl | 7-NH2 | H | Me |
| 518 | CH2CH2Ph | H | Cl | 7-NH2 | H | NH2 |
| 519 | CH2CH2Ph | H | Cl | 7-NH2 | H | OH |
| 520 | CH2CH2Ph | H | Cl | 7-NH2 | Me | Me |

TABLE 14

| Compound No. | R1 | R2 | R3 | R3' | R4 | R5 |
|---|---|---|---|---|---|---|
| 521 | CH2CH2Ph | H | Cl | 7-NH2 | Me | NH2 |
| 522 | CH2CH2Ph | H | Cl | 7-NH2 | Me | OH |
| 523 | CH2CH2Ph | H | Cl | 5-Me | H | Me |
| 524 | CH2CH2Ph | H | Cl | 5-Me | H | NH2 |
| 525 | CH2CH2Ph | H | Cl | 5-Me | H | OH |
| 526 | CH2CH2Ph | H | Cl | 5-Me | Me | Me |
| 527 | CH2CH2Ph | H | Cl | 5-Me | Me | NH2 |
| 528 | CH2CH2Ph | H | Cl | 5-Me | Me | OH |
| 529 | CH2CH2Ph | H | Cl | 6-Me | H | Me |
| 530 | CH2CH2Ph | H | Cl | 6-Me | H | NH2 |
| 531 | CH2CH2Ph | H | Cl | 6-Me | H | OH |
| 532 | CH2CH2Ph | H | Cl | 6-Me | Me | Me |
| 533 | CH2CH2Ph | H | Cl | 6-Me | Me | NH2 |
| 534 | CH2CH2Ph | H | Cl | 6-Me | Me | OH |
| 535 | CH2CH2Ph | H | Cl | 7-Me | H | Me |
| 536 | CH2CH2Ph | H | Cl | 7-Me | H | NH2 |
| 537 | CH2CH2Ph | H | Cl | 7-Me | H | OH |
| 538 | CH2CH2Ph | H | Cl | 7-Me | Me | Me |
| 539 | CH2CH2Ph | H | Cl | 7-Me | Me | NH2 |
| 540 | CH2CH2Ph | H | Cl | 7-Me | Me | OH |
| 541 | CH2CH2Ph | H | NH2 | 5-Cl | H | Me |
| 542 | CH2CH2Ph | H | NH2 | 5-Cl | H | NH2 |
| 543 | CH2CH2Ph | H | NH2 | 5-Cl | H | OH |
| 544 | CH2CH2Ph | H | NH2 | 5-Cl | Me | Me |
| 545 | CH2CH2Ph | H | NH2 | 5-Cl | Me | NH2 |
| 546 | CH2CH2Ph | H | NH2 | 5-Cl | Me | OH |
| 547 | CH2CH2Ph | H | NH2 | 6-Cl | H | Me |
| 548 | CH2CH2Ph | H | NH2 | 6-Cl | H | NH2 |
| 549 | CH2CH2Ph | H | NH2 | 6-Cl | H | OH |
| 550 | CH2CH2Ph | H | NH2 | 6-Cl | Me | Me |
| 551 | CH2CH2Ph | H | NH2 | 6-Cl | Me | NH2 |
| 552 | CH2CH2Ph | H | NH2 | 6-Cl | Me | OH |
| 553 | CH2CH2Ph | H | NH2 | 7-Cl | H | Me |
| 554 | CH2CH2Ph | H | NH2 | 7-Cl | H | NH2 |
| 555 | CH2CH2Ph | H | NH2 | 7-Cl | H | OH |
| 556 | CH2CH2Ph | H | NH2 | 7-Cl | Me | Me |
| 557 | CH2CH2Ph | H | NH2 | 7-Cl | Me | NH2 |
| 558 | CH2CH2Ph | H | NH2 | 7-Cl | Me | OH |
| 559 | CH2CH2Ph | H | NH2 | 5-NH2 | H | Me |
| 560 | CH2CH2Ph | H | NH2 | 5-NH2 | H | NH2 |

TABLE 15

| Compound No. | R1 | R2 | R3 | R3' | R4 | R5 |
|---|---|---|---|---|---|---|
| 561 | CH2CH2Ph | H | NH2 | 5-NH2 | H | OH |
| 562 | CH2CH2Ph | H | NH2 | 5-NH2 | Me | Me |

TABLE 15-continued

| Compound No. | R1 | R2 | R3 | R3' | R4 | R5 |
|---|---|---|---|---|---|---|
| 563 | CH2CH2Ph | H | NH2 | 5-NH2 | Me | NH2 |
| 564 | CH2CH2Ph | H | NH2 | 5-NH2 | Me | OH |
| 565 | CH2CH2Ph | H | NH2 | 6-NH2 | H | Me |
| 566 | CH2CH2Ph | H | NH2 | 6-NH2 | H | NH2 |
| 567 | CH2CH2Ph | H | NH2 | 6-NH2 | H | OH |
| 568 | CH2CH2Ph | H | NH2 | 6-NH2 | Me | Me |
| 569 | CH2CH2Ph | H | NH2 | 6-NH2 | Me | NH2 |
| 570 | CH2CH2Ph | H | NH2 | 6-NH2 | Me | OH |
| 571 | CH2CH2Ph | H | NH2 | 7-NH2 | H | Me |
| 572 | CH2CH2Ph | H | NH2 | 7-NH2 | H | NH2 |
| 573 | CH2CH2Ph | H | NH2 | 7-NH2 | H | OH |
| 574 | CH2CH2Ph | H | NH2 | 7-NH2 | Me | Me |
| 575 | CH2CH2Ph | H | NH2 | 7-NH2 | Me | NH2 |
| 576 | CH2CH2Ph | H | NH2 | 7-NH2 | Me | OH |
| 577 | CH2CH2Ph | H | NH2 | 5-Me | H | Me |
| 578 | CH2CH2Ph | H | NH2 | 5-Me | H | NH2 |
| 579 | CH2CH2Ph | H | NH2 | 5-Me | H | OH |
| 580 | CH2CH2Ph | H | NH2 | 5-Me | Me | Me |
| 581 | CH2CH2Ph | H | NH2 | 5-Me | Me | NH2 |
| 582 | CH2CH2Ph | H | NH2 | 5-Me | Me | OH |
| 583 | CH2CH2Ph | H | NH2 | 6-Me | H | Me |
| 584 | CH2CH2Ph | H | NH2 | 6-Me | H | NH2 |
| 585 | CH2CH2Ph | H | NH2 | 6-Me | H | OH |
| 586 | CH2CH2Ph | H | NH2 | 6-Me | Me | Me |
| 587 | CH2CH2Ph | H | NH2 | 6-Me | Me | NH2 |
| 588 | CH2CH2Ph | H | NH2 | 6-Me | Me | OH |
| 589 | CH2CH2Ph | H | NH2 | 7-Me | H | Me |
| 590 | CH2CH2Ph | H | NH2 | 7-Me | H | NH2 |
| 591 | CH2CH2Ph | H | NH2 | 7-Me | H | OH |
| 592 | CH2CH2Ph | H | NH2 | 7-Me | Me | Me |
| 593 | CH2CH2Ph | H | NH2 | 7-Me | Me | NH2 |
| 594 | CH2CH2Ph | H | NH2 | 7-Me | Me | OH |
| 595 | CH2CH2Ph | H | Me | 5-Cl | H | Me |
| 596 | CH2CH2Ph | H | Me | 5-Cl | H | NH2 |
| 597 | CH2CH2Ph | H | Me | 5-Cl | H | OH |
| 598 | CH2CH2Ph | H | Me | 5-Cl | Me | Me |
| 599 | CH2CH2Ph | H | Me | 5-Cl | Me | NH2 |
| 600 | CH2CH2Ph | H | Me | 5-Cl | Me | OH |

TABLE 16

| Compound No. | R1 | R2 | R3 | R3' | R4 | R5 |
|---|---|---|---|---|---|---|
| 601 | CH2CH2Ph | H | Me | 6-Cl | H | Me |
| 602 | CH2CH2Ph | H | Me | 6-Cl | H | NH2 |
| 603 | CH2CH2Ph | H | Me | 6-Cl | H | OH |
| 604 | CH2CH2Ph | H | Me | 6-Cl | Me | Me |
| 605 | CH2CH2Ph | H | Me | 6-Cl | Me | NH2 |
| 606 | CH2CH2Ph | H | Me | 6-Cl | Me | OH |
| 607 | CH2CH2Ph | H | Me | 7-Cl | H | Me |
| 608 | CH2CH2Ph | H | Me | 7-Cl | H | NH2 |
| 609 | CH2CH2Ph | H | Me | 7-Cl | H | OH |
| 610 | CH2CH2Ph | H | Me | 7-Cl | Me | Me |
| 611 | CH2CH2Ph | H | Me | 7-Cl | Me | NH2 |
| 612 | CH2CH2Ph | H | Me | 7-Cl | Me | OH |
| 613 | CH2CH2Ph | H | Me | 5-NH2 | H | Me |
| 614 | CH2CH2Ph | H | Me | 5-NH2 | H | NH2 |
| 615 | CH2CH2Ph | H | Me | 5-NH2 | H | OH |
| 616 | CH2CH2Ph | H | Me | 5-NH2 | Me | Me |
| 617 | CH2CH2Ph | H | Me | 5-NH2 | Me | NH2 |
| 618 | CH2CH2Ph | H | Me | 5-NH2 | Me | OH |
| 619 | CH2CH2Ph | H | Me | 6-NH2 | H | Me |
| 620 | CH2CH2Ph | H | Me | 6-NH2 | H | NH2 |
| 621 | CH2CH2Ph | H | Me | 6-NH2 | H | OH |
| 622 | CH2CH2Ph | H | Me | 6-NH2 | Me | Me |
| 623 | CH2CH2Ph | H | Me | 6-NH2 | Me | NH2 |
| 624 | CH2CH2Ph | H | Me | 6-NH2 | Me | OH |
| 625 | CH2CH2Ph | H | Me | 7-NH2 | H | Me |
| 626 | CH2CH2Ph | H | Me | 7-NH2 | H | NH2 |
| 627 | CH2CH2Ph | H | Me | 7-NH2 | H | OH |
| 628 | CH2CH2Ph | H | Me | 7-NH2 | Me | Me |
| 629 | CH2CH2Ph | H | Me | 7-NH2 | Me | NH2 |
| 630 | CH2CH2Ph | H | Me | 7-NH2 | Me | OH |
| 631 | CH2CH2Ph | H | Me | 5-Me | H | Me |

TABLE 16-continued

| Compound No. | R1 | R2 | R3 | R3' | R4 | R5 |
|---|---|---|---|---|---|---|
| 632 | CH2CH2Ph | H | Me | 5-Me | H | NH2 |
| 633 | CH2CH2Ph | H | Me | 5-Me | H | OH |
| 634 | CH2CH2Ph | H | Me | 5-Me | Me | Me |
| 635 | CH2CH2Ph | H | Me | 5-Me | Me | NH2 |
| 636 | CH2CH2Ph | H | Me | 5-Me | Me | OH |
| 637 | CH2CH2Ph | H | Me | 6-Me | H | Me |
| 638 | CH2CH2Ph | H | Me | 6-Me | H | NH2 |
| 639 | CH2CH2Ph | H | Me | 6-Me | H | OH |
| 640 | CH2CH2Ph | H | Me | 6-Me | Me | Me |

TABLE 17

| Compound No. | R1 | R2 | R3 | R3' | R4 | R5 |
|---|---|---|---|---|---|---|
| 641 | CH2CH2Ph | H | Me | 6-Me | Me | NH2 |
| 642 | CH2CH2Ph | H | Me | 6-Me | Me | OH |
| 643 | CH2CH2Ph | H | Me | 7-Me | H | Me |
| 644 | CH2CH2Ph | H | Me | 7-Me | H | NH2 |
| 645 | CH2CH2Ph | H | Me | 7-Me | H | OH |
| 646 | CH2CH2Ph | H | Me | 7-Me | Me | Me |
| 647 | CH2CH2Ph | H | Me | 7-Me | Me | NH2 |
| 648 | CH2CH2Ph | H | Me | 7-Me | Me | OH |
| 649 | CH2CH2Ph | OH | Cl | 5-Cl | H | Me |
| 650 | CH2CH2Ph | OH | Cl | 5-Cl | H | NH2 |
| 651 | CH2CH2Ph | OH | Cl | 5-Cl | H | OH |
| 652 | CH2CH2Ph | OH | Cl | 5-Cl | Me | Me |
| 653 | CH2CH2Ph | OH | Cl | 5-Cl | Me | NH2 |
| 654 | CH2CH2Ph | OH | Cl | 5-Cl | Me | OH |
| 655 | CH2CH2Ph | OH | Cl | 6-Cl | H | Me |
| 656 | CH2CH2Ph | OH | Cl | 6-Cl | H | NH2 |
| 657 | CH2CH2Ph | OH | Cl | 6-Cl | H | OH |
| 658 | CH2CH2Ph | OH | Cl | 6-Cl | Me | Me |
| 659 | CH2CH2Ph | OH | Cl | 6-Cl | Me | NH2 |
| 660 | CH2CH2Ph | OH | Cl | 6-Cl | Me | OH |
| 661 | CH2CH2Ph | OH | Cl | 7-Cl | H | Me |
| 662 | CH2CH2Ph | OH | Cl | 7-Cl | H | NH2 |
| 663 | CH2CH2Ph | OH | Cl | 7-Cl | H | OH |
| 664 | CH2CH2Ph | OH | Cl | 7-Cl | Me | Me |
| 665 | CH2CH2Ph | OH | Cl | 7-Cl | Me | NH2 |
| 666 | CH2CH2Ph | OH | Cl | 7-Cl | Me | OH |
| 667 | CH2CH2Ph | OH | Cl | 5-NH2 | H | Me |
| 668 | CH2CH2Ph | OH | Cl | 5-NH2 | H | NH2 |
| 669 | CH2CH2Ph | OH | Cl | 5-NH2 | H | OH |
| 670 | CH2CH2Ph | OH | Cl | 5-NH2 | Me | Me |
| 671 | CH2CH2Ph | OH | Cl | 5-NH2 | Me | NH2 |
| 672 | CH2CH2Ph | OH | Cl | 5-NH2 | Me | OH |
| 673 | CH2CH2Ph | OH | Cl | 6-NH2 | H | Me |
| 674 | CH2CH2Ph | OH | Cl | 6-NH2 | H | NH2 |
| 675 | CH2CH2Ph | OH | Cl | 6-NH2 | H | OH |
| 676 | CH2CH2Ph | OH | Cl | 6-NH2 | Me | Me |
| 677 | CH2CH2Ph | OH | Cl | 6-NH2 | Me | NH2 |
| 678 | CH2CH2Ph | OH | Cl | 6-NH2 | Me | OH |
| 679 | CH2CH2Ph | OH | Cl | 7-NH2 | H | Me |
| 680 | CH2CH2Ph | OH | Cl | 7-NH2 | H | NH2 |

TABLE 18

| Compound No. | R1 | R2 | R3 | R3' | R4 | R5 |
|---|---|---|---|---|---|---|
| 681 | CH2CH2Ph | OH | Cl | 7-NH2 | H | OH |
| 682 | CH2CH2Ph | OH | Cl | 7-NH2 | Me | Me |
| 683 | CH2CH2Ph | OH | Cl | 7-NH2 | Me | NH2 |
| 684 | CH2CH2Ph | OH | Cl | 7-NH2 | Me | OH |
| 685 | CH2CH2Ph | OH | Cl | 5-Me | H | Me |
| 686 | CH2CH2Ph | OH | Cl | 5-Me | H | NH2 |
| 687 | CH2CH2Ph | OH | Cl | 5-Me | H | OH |
| 688 | CH2CH2Ph | OH | Cl | 5-Me | Me | Me |
| 689 | CH2CH2Ph | OH | Cl | 5-Me | Me | NH2 |
| 690 | CH2CH2Ph | OH | Cl | 5-Me | Me | OH |
| 691 | CH2CH2Ph | OH | Cl | 6-Me | H | Me |
| 692 | CH2CH2Ph | OH | Cl | 6-Me | H | NH2 |
| 693 | CH2CH2Ph | OH | Cl | 6-Me | H | OH |

TABLE 18-continued

| Compound No. | R1 | R2 | R3 | R3' | R4 | R5 |
|---|---|---|---|---|---|---|
| 694 | CH2CH2Ph | OH | Cl | 6-Me | Me | Me |
| 695 | CH2CH2Ph | OH | Cl | 6-Me | Me | NH2 |
| 696 | CH2CH2Ph | OH | Cl | 6-Me | Me | OH |
| 697 | CH2CH2Ph | OH | Cl | 7-Me | H | Me |
| 698 | CH2CH2Ph | OH | Cl | 7-Me | H | NH2 |
| 699 | CH2CH2Ph | OH | Cl | 7-Me | H | OH |
| 700 | CH2CH2Ph | OH | Cl | 7-Me | Me | Me |
| 701 | CH2CH2Ph | OH | Cl | 7-Me | Me | NH2 |
| 702 | CH2CH2Ph | OH | Cl | 7-Me | Me | OH |
| 703 | CH2CH2Ph | OH | NH2 | 5-Cl | H | Me |
| 704 | CH2CH2Ph | OH | NH2 | 5-Cl | H | NH2 |
| 705 | CH2CH2Ph | OH | NH2 | 5-Cl | H | OH |
| 706 | CH2CH2Ph | OH | NH2 | 5-Cl | Me | Me |
| 707 | CH2CH2Ph | OH | NH2 | 5-Cl | Me | NH2 |
| 708 | CH2CH2Ph | OH | NH2 | 5-Cl | Me | OH |
| 709 | CH2CH2Ph | OH | NH2 | 6-Cl | H | Me |
| 710 | CH2CH2Ph | OH | NH2 | 6-Cl | H | NH2 |
| 711 | CH2CH2Ph | OH | NH2 | 6-Cl | H | OH |
| 712 | CH2CH2Ph | OH | NH2 | 6-Cl | Me | Me |
| 713 | CH2CH2Ph | OH | NH2 | 6-Cl | Me | NH2 |
| 714 | CH2CH2Ph | OH | NH2 | 6-Cl | Me | OH |
| 715 | CH2CH2Ph | OH | NH2 | 7-Cl | H | Me |
| 716 | CH2CH2Ph | OH | NH2 | 7-Cl | H | NH2 |
| 717 | CH2CH2Ph | OH | NH2 | 7-Cl | H | OH |
| 718 | CH2CH2Ph | OH | NH2 | 7-Cl | Me | Me |
| 719 | CH2CH2Ph | OH | NH2 | 7-Cl | Me | NH2 |
| 720 | CH2CH2Ph | OH | NH2 | 7-Cl | Me | OH |

TABLE 19

| Compound No. | R1 | R2 | R3 | R3' | R4 | R5 |
|---|---|---|---|---|---|---|
| 721 | CH2CH2Ph | OH | NH2 | 5-NH2 | H | Me |
| 722 | CH2CH2Ph | OH | NH2 | 5-NH2 | H | NH2 |
| 723 | CH2CH2Ph | OH | NH2 | 5-NH2 | H | OH |
| 724 | CH2CH2Ph | OH | NH2 | 5-NH2 | Me | Me |
| 725 | CH2CH2Ph | OH | NH2 | 5-NH2 | Me | NH2 |
| 726 | CH2CH2Ph | OH | NH2 | 5-NH2 | Me | OH |
| 727 | CH2CH2Ph | OH | NH2 | 6-NH2 | H | Me |
| 728 | CH2CH2Ph | OH | NH2 | 6-NH2 | H | NH2 |
| 729 | CH2CH2Ph | OH | NH2 | 6-NH2 | H | OH |
| 730 | CH2CH2Ph | OH | NH2 | 6-NH2 | Me | Me |
| 731 | CH2CH2Ph | OH | NH2 | 6-NH2 | Me | NH2 |
| 732 | CH2CH2Ph | OH | NH2 | 6-NH2 | Me | OH |
| 733 | CH2CH2Ph | OH | NH2 | 7-NH2 | H | Me |
| 734 | CH2CH2Ph | OH | NH2 | 7-NH2 | H | NH2 |
| 735 | CH2CH2Ph | OH | NH2 | 7-NH2 | H | OH |
| 736 | CH2CH2Ph | OH | NH2 | 7-NH2 | Me | Me |
| 737 | CH2CH2Ph | OH | NH2 | 7-NH2 | Me | NH2 |
| 738 | CH2CH2Ph | OH | NH2 | 7-NH2 | Me | OH |
| 739 | CH2CH2Ph | OH | NH2 | 5-Me | H | Me |
| 740 | CH2CH2Ph | OH | NH2 | 5-Me | H | NH2 |
| 741 | CH2CH2Ph | OH | NH2 | 5-Me | H | OH |
| 742 | CH2CH2Ph | OH | NH2 | 5-Me | Me | Me |
| 743 | CH2CH2Ph | OH | NH2 | 5-Me | Me | NH2 |
| 744 | CH2CH2Ph | OH | NH2 | 5-Me | Me | OH |
| 745 | CH2CH2Ph | OH | NH2 | 6-Me | H | Me |
| 746 | CH2CH2Ph | OH | NH2 | 6-Me | H | NH2 |
| 747 | CH2CH2Ph | OH | NH2 | 6-Me | H | OH |
| 748 | CH2CH2Ph | OH | NH2 | 6-Me | Me | Me |
| 749 | CH2CH2Ph | OH | NH2 | 6-Me | Me | NH2 |
| 750 | CH2CH2Ph | OH | NH2 | 6-Me | Me | OH |
| 751 | CH2CH2Ph | OH | NH2 | 7-Me | H | Me |
| 752 | CH2CH2Ph | OH | NH2 | 7-Me | H | NH2 |
| 753 | CH2CH2Ph | OH | NH2 | 7-Me | H | OH |
| 754 | CH2CH2Ph | OH | NH2 | 7-Me | Me | Me |
| 755 | CH2CH2Ph | OH | NH2 | 7-Me | Me | NH2 |
| 756 | CH2CH2Ph | OH | NH2 | 7-Me | Me | OH |
| 757 | CH2CH2Ph | OH | Me | 5-Cl | H | Me |
| 758 | CH2CH2Ph | OH | Me | 5-Cl | H | NH2 |
| 759 | CH2CH2Ph | OH | Me | 5-Cl | H | OH |
| 760 | CH2CH2Ph | OH | Me | 5-Cl | Me | Me |

TABLE 20

| Compound No. | R1 | R2 | R3 | R3' | R4 | R5 |
|---|---|---|---|---|---|---|
| 761 | CH2CH2Ph | OH | Me | 5-Cl | Me | NH2 |
| 762 | CH2CH2Ph | OH | Me | 5-Cl | Me | OH |
| 763 | CH2CH2Ph | OH | Me | 6-Cl | H | Me |
| 764 | CH2CH2Ph | OH | Me | 6-Cl | H | NH2 |
| 765 | CH2CH2Ph | OH | Me | 6-Cl | H | OH |
| 766 | CH2CH2Ph | OH | Me | 6-Cl | Me | Me |
| 767 | CH2CH2Ph | OH | Me | 6-Cl | Me | NH2 |
| 768 | CH2CH2Ph | OH | Me | 6-Cl | Me | OH |
| 769 | CH2CH2Ph | OH | Me | 7-Cl | H | Me |
| 770 | CH2CH2Ph | OH | Me | 7-Cl | H | NH2 |
| 771 | CH2CH2Ph | OH | Me | 7-Cl | H | OH |
| 772 | CH2CH2Ph | OH | Me | 7-Cl | Me | Me |
| 773 | CH2CH2Ph | OH | Me | 7-Cl | Me | NH2 |
| 774 | CH2CH2Ph | OH | Me | 7-Cl | Me | OH |
| 775 | CH2CH2Ph | OH | Me | 5-NH2 | H | Me |
| 776 | CH2CH2Ph | OH | Me | 5-NH2 | H | NH2 |
| 777 | CH2CH2Ph | OH | Me | 5-NH2 | H | OH |
| 778 | CH2CH2Ph | OH | Me | 5-NH2 | Me | Me |
| 779 | CH2CH2Ph | OH | Me | 5-NH2 | Me | NH2 |
| 780 | CH2CH2Ph | OH | Me | 5-NH2 | Me | OH |
| 781 | CH2CH2Ph | OH | Me | 6-NH2 | H | Me |
| 782 | CH2CH2Ph | OH | Me | 6-NH2 | H | NH2 |
| 783 | CH2CH2Ph | OH | Me | 6-NH2 | H | OH |
| 784 | CH2CH2Ph | OH | Me | 6-NH2 | Me | Me |
| 785 | CH2CH2Ph | OH | Me | 6-NH2 | Me | NH2 |
| 786 | CH2CH2Ph | OH | Me | 6-NH2 | Me | OH |
| 787 | CH2CH2Ph | OH | Me | 7-NH2 | H | Me |
| 788 | CH2CH2Ph | OH | Me | 7-NH2 | H | NH2 |
| 789 | CH2CH2Ph | OH | Me | 7-NH2 | H | OH |
| 790 | CH2CH2Ph | OH | Me | 7-NH2 | Me | Me |
| 791 | CH2CH2Ph | OH | Me | 7-NH2 | Me | NH2 |
| 792 | CH2CH2Ph | OH | Me | 7-NH2 | Me | OH |
| 793 | CH2CH2Ph | OH | Me | 5-Me | H | Me |
| 794 | CH2CH2Ph | OH | Me | 5-Me | H | NH2 |
| 795 | CH2CH2Ph | OH | Me | 5-Me | H | OH |
| 796 | CH2CH2Ph | OH | Me | 5-Me | Me | Me |
| 797 | CH2CH2Ph | OH | Me | 5-Me | Me | NH2 |
| 798 | CH2CH2Ph | OH | Me | 5-Me | Me | OH |
| 799 | CH2CH2Ph | OH | Me | 6-Me | H | Me |
| 800 | CH2CH2Ph | OH | Me | 6-Me | H | NH2 |

TABLE 21

| Compound No. | R1 | R2 | R3 | R3' | R4 | R5 |
|---|---|---|---|---|---|---|
| 801 | CH2CH2Ph | OH | Me | 6-Me | H | OH |
| 802 | CH2CH2Ph | OH | Me | 6-Me | Me | Me |
| 803 | CH2CH2Ph | OH | Me | 6-Me | Me | NH2 |
| 804 | CH2CH2Ph | OH | Me | 6-Me | Me | OH |
| 805 | CH2CH2Ph | OH | Me | 7-Me | H | Me |
| 806 | CH2CH2Ph | OH | Me | 7-Me | H | NH2 |
| 807 | CH2CH2Ph | OH | Me | 7-Me | H | OH |
| 808 | CH2CH2Ph | OH | Me | 7-Me | Me | Me |
| 809 | CH2CH2Ph | OH | Me | 7-Me | Me | NH2 |
| 810 | CH2CH2Ph | OH | Me | 7-Me | Me | OH |
| 811 | CH2CH2Ph | OMe | Cl | 5-Cl | H | Me |
| 812 | CH2CH2Ph | OMe | Cl | 5-Cl | H | NH2 |
| 813 | CH2CH2Ph | OMe | Cl | 5-Cl | H | OH |
| 814 | CH2CH2Ph | OMe | Cl | 5-Cl | Me | Me |
| 815 | CH2CH2Ph | OMe | Cl | 5-Cl | Me | NH2 |
| 816 | CH2CH2Ph | OMe | Cl | 5-Cl | Me | OH |
| 817 | CH2CH2Ph | OMe | Cl | 6-Cl | H | Me |
| 818 | CH2CH2Ph | OMe | Cl | 6-Cl | H | NH2 |
| 819 | CH2CH2Ph | OMe | Cl | 6-Cl | H | OH |
| 820 | CH2CH2Ph | OMe | Cl | 6-Cl | Me | Me |
| 821 | CH2CH2Ph | OMe | Cl | 6-Cl | Me | NH2 |
| 822 | CH2CH2Ph | OMe | Cl | 6-Cl | Me | OH |
| 823 | CH2CH2Ph | OMe | Cl | 7-Cl | H | Me |
| 824 | CH2CH2Ph | OMe | Cl | 7-Cl | H | NH2 |
| 825 | CH2CH2Ph | OMe | Cl | 7-Cl | H | OH |
| 826 | CH2CH2Ph | OMe | Cl | 7-Cl | Me | Me |
| 827 | CH2CH2Ph | OMe | Cl | 7-Cl | Me | NH2 |
| 828 | CH2CH2Ph | OMe | Cl | 7-Cl | Me | OH |
| 829 | CH2CH2Ph | OMe | Cl | 5-NH2 | H | Me |

TABLE 21-continued

| Compound No. | R1 | R2 | R3 | R3' | R4 | R5 |
|---|---|---|---|---|---|---|
| 830 | CH2CH2Ph | OMe | Cl | 5-NH2 | H | NH2 |
| 831 | CH2CH2Ph | OMe | Cl | 5-NH2 | H | OH |
| 832 | CH2CH2Ph | OMe | Cl | 5-NH2 | Me | Me |
| 833 | CH2CH2Ph | OMe | Cl | 5-NH2 | Me | NH2 |
| 834 | CH2CH2Ph | OMe | Cl | 5-NH2 | Me | OH |
| 835 | CH2CH2Ph | OMe | Cl | 6-NH2 | H | Me |
| 836 | CH2CH2Ph | OMe | Cl | 6-NH2 | H | NH2 |
| 837 | CH2CH2Ph | OMe | Cl | 6-NH2 | H | OH |
| 838 | CH2CH2Ph | OMe | Cl | 6-NH2 | Me | Me |
| 839 | CH2CH2Ph | OMe | Cl | 6-NH2 | Me | NH2 |
| 840 | CH2CH2Ph | OMe | Cl | 6-NH2 | Me | OH |

TABLE 22

| Compound No. | R1 | R2 | R3 | R3' | R4 | R5 |
|---|---|---|---|---|---|---|
| 841 | CH2CH2Ph | OMe | Cl | 7-NH2 | H | Me |
| 842 | CH2CH2Ph | OMe | Cl | 7-NH2 | H | NH2 |
| 843 | CH2CH2Ph | OMe | Cl | 7-NH2 | H | OH |
| 844 | CH2CH2Ph | OMe | Cl | 7-NH2 | Me | Me |
| 845 | CH2CH2Ph | OMe | Cl | 7-NH2 | Me | NH2 |
| 846 | CH2CH2Ph | OMe | Cl | 7-NH2 | Me | OH |
| 847 | CH2CH2Ph | OMe | Cl | 5-Me | H | Me |
| 848 | CH2CH2Ph | OMe | Cl | 5-Me | H | NH2 |
| 849 | CH2CH2Ph | OMe | Cl | 5-Me | H | OH |
| 850 | CH2CH2Ph | OMe | Cl | 5-Me | Me | Me |
| 851 | CH2CH2Ph | OMe | Cl | 5-Me | Me | NH2 |
| 852 | CH2CH2Ph | OMe | Cl | 5-Me | Me | OH |
| 853 | CH2CH2Ph | OMe | Cl | 6-Me | H | Me |
| 854 | CH2CH2Ph | OMe | Cl | 6-Me | H | NH2 |
| 855 | CH2CH2Ph | OMe | Cl | 6-Me | H | OH |
| 856 | CH2CH2Ph | OMe | Cl | 6-Me | Me | Me |
| 857 | CH2CH2Ph | OMe | Cl | 6-Me | Me | NH2 |
| 858 | CH2CH2Ph | OMe | Cl | 6-Me | Me | OH |
| 859 | CH2CH2Ph | OMe | Cl | 7-Me | H | Me |
| 860 | CH2CH2Ph | OMe | Cl | 7-Me | H | NH2 |
| 861 | CH2CH2Ph | OMe | Cl | 7-Me | H | OH |
| 862 | CH2CH2Ph | OMe | Cl | 7-Me | Me | Me |
| 863 | CH2CH2Ph | OMe | Cl | 7-Me | Me | NH2 |
| 864 | CH2CH2Ph | OMe | Cl | 7-Me | Me | OH |
| 865 | CH2CH2Ph | OMe | NH2 | 5-Cl | H | Me |
| 866 | CH2CH2Ph | OMe | NH2 | 5-Cl | H | NH2 |
| 867 | CH2CH2Ph | OMe | NH2 | 5-Cl | H | OH |
| 868 | CH2CH2Ph | OMe | NH2 | 5-Cl | Me | Me |
| 869 | CH2CH2Ph | OMe | NH2 | 5-Cl | Me | NH2 |
| 870 | CH2CH2Ph | OMe | NH2 | 5-Cl | Me | OH |
| 871 | CH2CH2Ph | OMe | NH2 | 6-Cl | H | Me |
| 872 | CH2CH2Ph | OMe | NH2 | 6-Cl | H | NH2 |
| 873 | CH2CH2Ph | OMe | NH2 | 6-Cl | H | OH |
| 874 | CH2CH2Ph | OMe | NH2 | 6-Cl | Me | Me |
| 875 | CH2CH2Ph | OMe | NH2 | 6-Cl | Me | NH2 |
| 876 | CH2CH2Ph | OMe | NH2 | 6-Cl | Me | OH |
| 877 | CH2CH2Ph | OMe | NH2 | 7-Cl | H | Me |
| 878 | CH2CH2Ph | OMe | NH2 | 7-Cl | H | NH2 |
| 879 | CH2CH2Ph | OMe | NH2 | 7-Cl | H | OH |
| 880 | CH2CH2Ph | OMe | NH2 | 7-Cl | Me | Me |

TABLE 23

| Compound No. | R1 | R2 | R3 | R3' | R4 | R5 |
|---|---|---|---|---|---|---|
| 881 | CH2CH2Ph | OMe | NH2 | 7-Cl | Me | NH2 |
| 882 | CH2CH2Ph | OMe | NH2 | 7-Cl | Me | OH |
| 883 | CH2CH2Ph | OMe | NH2 | 5-NH2 | H | Me |
| 884 | CH2CH2Ph | OMe | NH2 | 5-NH2 | H | NH2 |
| 885 | CH2CH2Ph | OMe | NH2 | 5-NH2 | H | OH |
| 886 | CH2CH2Ph | OMe | NH2 | 5-NH2 | Me | Me |
| 887 | CH2CH2Ph | OMe | NH2 | 5-NH2 | Me | NH2 |
| 888 | CH2CH2Ph | OMe | NH2 | 5-NH2 | Me | OH |
| 889 | CH2CH2Ph | OMe | NH2 | 6-NH2 | H | Me |
| 890 | CH2CH2Ph | OMe | NH2 | 6-NH2 | H | NH2 |
| 891 | CH2CH2Ph | OMe | NH2 | 6-NH2 | H | OH |

TABLE 23-continued

| Compound No. | R1 | R2 | R3 | R3' | R4 | R5 |
|---|---|---|---|---|---|---|
| 892 | CH2CH2Ph | OMe | NH2 | 6-NH2 | Me | Me |
| 893 | CH2CH2Ph | OMe | NH2 | 6-NH2 | Me | NH2 |
| 894 | CH2CH2Ph | OMe | NH2 | 6-NH2 | Me | OH |
| 895 | CH2CH2Ph | OMe | NH2 | 7-NH2 | H | Me |
| 896 | CH2CH2Ph | OMe | NH2 | 7-NH2 | H | NH2 |
| 897 | CH2CH2Ph | OMe | NH2 | 7-NH2 | H | OH |
| 898 | CH2CH2Ph | OMe | NH2 | 7-NH2 | Me | Me |
| 899 | CH2CH2Ph | OMe | NH2 | 7-NH2 | Me | NH2 |
| 900 | CH2CH2Ph | OMe | NH2 | 7-NH2 | Me | OH |
| 901 | CH2CH2Ph | OMe | NH2 | 5-Me | H | Me |
| 902 | CH2CH2Ph | OMe | NH2 | 5-Me | H | NH2 |
| 903 | CH2CH2Ph | OMe | NH2 | 5-Me | H | OH |
| 904 | CH2CH2Ph | OMe | NH2 | 5-Me | Me | Me |
| 905 | CH2CH2Ph | OMe | NH2 | 5-Me | Me | NH2 |
| 906 | CH2CH2Ph | OMe | NH2 | 5-Me | Me | OH |
| 907 | CH2CH2Ph | OMe | NH2 | 6-Me | H | Me |
| 908 | CH2CH2Ph | OMe | NH2 | 6-Me | H | NH2 |
| 909 | CH2CH2Ph | OMe | NH2 | 6-Me | H | OH |
| 910 | CH2CH2Ph | OMe | NH2 | 6-Me | Me | Me |
| 911 | CH2CH2Ph | OMe | NH2 | 6-Me | Me | NH2 |
| 912 | CH2CH2Ph | OMe | NH2 | 6-Me | Me | OH |
| 913 | CH2CH2Ph | OMe | NH2 | 7-Me | H | Me |
| 914 | CH2CH2Ph | OMe | NH2 | 7-Me | H | NH2 |
| 915 | CH2CH2Ph | OMe | NH2 | 7-Me | H | OH |
| 916 | CH2CH2Ph | OMe | NH2 | 7-Me | Me | Me |
| 917 | CH2CH2Ph | OMe | NH2 | 7-Me | Me | NH2 |
| 918 | CH2CH2Ph | OMe | NH2 | 7-Me | Me | OH |
| 919 | CH2CH2Ph | OMe | Me | 5-Cl | H | Me |
| 920 | CH2CH2Ph | OMe | Me | 5-Cl | H | NH2 |

TABLE 24

| Compound No. | R1 | R2 | R3 | R3' | R4 | R5 |
|---|---|---|---|---|---|---|
| 921 | CH2CH2Ph | OMe | Me | 5-Cl | H | OH |
| 922 | CH2CH2Ph | OMe | Me | 5-Cl | Me | Me |
| 923 | CH2CH2Ph | OMe | Me | 5-Cl | Me | NH2 |
| 924 | CH2CH2Ph | OMe | Me | 5-Cl | Me | OH |
| 925 | CH2CH2Ph | OMe | Me | 6-Cl | H | Me |
| 926 | CH2CH2Ph | OMe | Me | 6-Cl | H | NH2 |
| 927 | CH2CH2Ph | OMe | Me | 6-Cl | H | OH |
| 928 | CH2CH2Ph | OMe | Me | 6-Cl | Me | Me |
| 929 | CH2CH2Ph | OMe | Me | 6-Cl | Me | NH2 |
| 930 | CH2CH2Ph | OMe | Me | 6-Cl | Me | OH |
| 931 | CH2CH2Ph | OMe | Me | 7-Cl | H | Me |
| 932 | CH2CH2Ph | OMe | Me | 7-Cl | H | NH2 |
| 933 | CH2CH2Ph | OMe | Me | 7-Cl | H | OH |
| 934 | CH2CH2Ph | OMe | Me | 7-Cl | Me | Me |
| 935 | CH2CH2Ph | OMe | Me | 7-Cl | Me | NH2 |
| 936 | CH2CH2Ph | OMe | Me | 7-Cl | Me | OH |
| 937 | CH2CH2Ph | OMe | Me | 5-NH2 | H | Me |
| 938 | CH2CH2Ph | OMe | Me | 5-NH2 | H | NH2 |
| 939 | CH2CH2Ph | OMe | Me | 5-NH2 | H | OH |
| 940 | CH2CH2Ph | OMe | Me | 5-NH2 | Me | Me |
| 941 | CH2CH2Ph | OMe | Me | 5-NH2 | Me | NH2 |
| 942 | CH2CH2Ph | OMe | Me | 5-NH2 | Me | OH |
| 943 | CH2CH2Ph | OMe | Me | 6-NH2 | H | Me |
| 944 | CH2CH2Ph | OMe | Me | 6-NH2 | H | NH2 |
| 945 | CH2CH2Ph | OMe | Me | 6-NH2 | H | OH |
| 946 | CH2CH2Ph | OMe | Me | 6-NH2 | Me | Me |
| 947 | CH2CH2Ph | OMe | Me | 6-NH2 | Me | NH2 |
| 948 | CH2CH2Ph | OMe | Me | 6-NH2 | Me | OH |
| 949 | CH2CH2Ph | OMe | Me | 7-NH2 | H | Me |
| 950 | CH2CH2Ph | OMe | Me | 7-NH2 | H | NH2 |
| 951 | CH2CH2Ph | OMe | Me | 7-NH2 | H | OH |
| 952 | CH2CH2Ph | OMe | Me | 7-NH2 | Me | Me |
| 953 | CH2CH2Ph | OMe | Me | 7-NH2 | Me | NH2 |
| 954 | CH2CH2Ph | OMe | Me | 7-NH2 | Me | OH |
| 955 | CH2CH2Ph | OMe | Me | 5-Me | H | Me |
| 956 | CH2CH2Ph | OMe | Me | 5-Me | H | NH2 |
| 957 | CH2CH2Ph | OMe | Me | 5-Me | H | OH |
| 958 | CH2CH2Ph | OMe | Me | 5-Me | Me | Me |

TABLE 24-continued

| Compound No. | R1 | R2 | R3 | R3' | R4 | R5 |
|---|---|---|---|---|---|---|
| 959 | CH2CH2Ph | OMe | Me | 5-Me | Me | NH2 |
| 960 | CH2CH2Ph | OMe | Me | 5-Me | Me | OH |

TABLE 25

| Compound No. | R1 | R2 | R3 | R3' | R4 | R5 |
|---|---|---|---|---|---|---|
| 961 | CH2CH2Ph | OMe | Me | 6-Me | H | Me |
| 962 | CH2CH2Ph | OMe | Me | 6-Me | H | NH2 |
| 963 | CH2CH2Ph | OMe | Me | 6-Me | H | OH |
| 964 | CH2CH2Ph | OMe | Me | 6-Me | Me | Me |
| 965 | CH2CH2Ph | OMe | Me | 6-Me | Me | NH2 |
| 966 | CH2CH2Ph | OMe | Me | 6-Me | Me | OH |
| 967 | CH2CH2Ph | OMe | Me | 7-Me | H | Me |
| 968 | CH2CH2Ph | OMe | Me | 7-Me | H | NH2 |
| 969 | CH2CH2Ph | OMe | Me | 7-Me | H | OH |
| 970 | CH2CH2Ph | OMe | Me | 7-Me | Me | Me |
| 971 | CH2CH2Ph | OMe | Me | 7-Me | Me | NH2 |
| 972 | CH2CH2Ph | OMe | Me | 7-Me | Me | OH |
| 973 | H | H | Cl | 5-H | H | Me |
| 974 | H | H | Cl | 5-H | H | NH2 |
| 975 | H | H | Cl | 5-H | H | OH |
| 976 | H | H | Cl | 5-H | Me | Me |
| 977 | H | H | Cl | 5-H | Me | NH2 |
| 978 | H | H | Cl | 5-H | Me | OH |
| 979 | H | H | Cl | 6-H | H | Me |
| 980 | H | H | Cl | 6-H | H | NH2 |
| 981 | H | H | Cl | 6-H | H | OH |
| 982 | H | H | Cl | 6-H | Me | Me |
| 983 | H | H | Cl | 6-H | Me | NH2 |
| 984 | H | H | Cl | 6-H | Me | OH |
| 985 | H | H | Cl | 7-H | H | Me |
| 986 | H | H | Cl | 7-H | H | NH2 |
| 987 | H | H | Cl | 7-H | H | OH |
| 988 | H | H | Cl | 7-H | Me | Me |
| 989 | H | H | Cl | 7-H | Me | NH2 |
| 990 | H | H | Cl | 7-H | Me | OH |
| 991 | H | H | Cl | 5-Cl | H | Me |
| 992 | H | H | Cl | 5-Cl | H | NH2 |
| 993 | H | H | Cl | 5-Cl | H | OH |
| 994 | H | H | Cl | 5-Cl | Me | Me |
| 995 | H | H | Cl | 5-Cl | Me | NH2 |
| 996 | H | H | Cl | 5-Cl | Me | OH |
| 997 | H | H | Cl | 6-Cl | H | Me |
| 998 | H | H | Cl | 6-Cl | H | NH2 |
| 999 | H | H | Cl | 6-Cl | H | OH |
| 1000 | H | H | Cl | 6-Cl | Me | Me |

TABLE 26

| Compound No. | R1 | R2 | R3 | R3' | R4 | R5 |
|---|---|---|---|---|---|---|
| 1001 | H | H | Cl | 6-Cl | Me | NH2 |
| 1002 | H | H | Cl | 6-Cl | Me | OH |
| 1003 | H | H | Cl | 7-Cl | H | Me |
| 1004 | H | H | Cl | 7-Cl | H | NH2 |
| 1005 | H | H | Cl | 7-Cl | H | OH |
| 1006 | H | H | Cl | 7-Cl | Me | Me |
| 1007 | H | H | Cl | 7-Cl | Me | NH2 |
| 1008 | H | H | Cl | 7-Cl | Me | OH |
| 1009 | H | H | Cl | 5-NH2 | H | Me |
| 1010 | H | H | Cl | 5-NH2 | H | NH2 |
| 1011 | H | H | Cl | 5-NH2 | H | OH |
| 1012 | H | H | Cl | 5-NH2 | Me | Me |
| 1013 | H | H | Cl | 5-NH2 | Me | NH2 |
| 1014 | H | H | Cl | 5-NH2 | Me | OH |
| 1015 | H | H | Cl | 6-NH2 | H | Me |
| 1016 | H | H | Cl | 6-NH2 | H | NH2 |
| 1017 | H | H | Cl | 6-NH2 | H | OH |
| 1018 | H | H | Cl | 6-NH2 | Me | Me |
| 1019 | H | H | Cl | 6-NH2 | Me | NH2 |
| 1020 | H | H | Cl | 6-NH2 | Me | OH |

TABLE 26-continued

| Compound No. | R1 | R2 | R3 | R3' | R4 | R5 |
|---|---|---|---|---|---|---|
| 1021 | H | H | Cl | 7-NH2 | H | Me |
| 1022 | H | H | Cl | 7-NH2 | H | NH2 |
| 1023 | H | H | Cl | 7-NH2 | H | OH |
| 1024 | H | H | Cl | 7-NH2 | Me | Me |
| 1025 | H | H | Cl | 7-NH2 | Me | NH2 |
| 1026 | H | H | Cl | 7-NH2 | Me | OH |
| 1027 | H | H | Cl | 5-Me | H | Me |
| 1028 | H | H | Cl | 5-Me | H | NH2 |
| 1029 | H | H | Cl | 5-Me | H | OH |
| 1030 | H | H | Cl | 5-Me | Me | Me |
| 1031 | H | H | Cl | 5-Me | Me | NH2 |
| 1032 | H | H | Cl | 5-Me | Me | OH |
| 1033 | H | H | Cl | 6-Me | H | Me |
| 1034 | H | H | Cl | 6-Me | H | NH2 |
| 1035 | H | H | Cl | 6-Me | H | OH |
| 1036 | H | H | Cl | 6-Me | Me | Me |
| 1037 | H | H | Cl | 6-Me | Me | NH2 |
| 1038 | H | H | Cl | 6-Me | Me | OH |
| 1039 | H | H | Cl | 7-Me | H | Me |
| 1040 | H | H | Cl | 7-Me | H | NH2 |

TABLE 27

| Compound No. | R1 | R2 | R3 | R3' | R4 | R5 |
|---|---|---|---|---|---|---|
| 1041 | H | H | Cl | 7-Me | H | OH |
| 1042 | H | H | Cl | 7-Me | Me | Me |
| 1043 | H | H | Cl | 7-Me | Me | NH2 |
| 1044 | H | H | Cl | 7-Me | Me | OH |
| 1045 | H | H | NH2 | 5-H | H | Me |
| 1046 | H | H | NH2 | 5-H | H | NH2 |
| 1047 | H | H | NH2 | 5-H | H | OH |
| 1048 | H | H | NH2 | 5-H | Me | Me |
| 1049 | H | H | NH2 | 5-H | Me | NH2 |
| 1050 | H | H | NH2 | 5-H | Me | OH |
| 1051 | H | H | NH2 | 6-H | H | Me |
| 1052 | H | H | NH2 | 6-H | H | NH2 |
| 1053 | H | H | NH2 | 6-H | H | OH |
| 1054 | H | H | NH2 | 6-H | Me | Me |
| 1055 | H | H | NH2 | 6-H | Me | NH2 |
| 1056 | H | H | NH2 | 6-H | Me | OH |
| 1057 | H | H | NH2 | 7-H | H | Me |
| 1058 | H | H | NH2 | 7-H | H | NH2 |
| 1059 | H | H | NH2 | 7-H | H | OH |
| 1060 | H | H | NH2 | 7-H | Me | Me |
| 1061 | H | H | NH2 | 7-H | Me | NH2 |
| 1062 | H | H | NH2 | 7-H | Me | OH |
| 1063 | H | H | NH2 | 5-Cl | H | Me |
| 1064 | H | H | NH2 | 5-Cl | H | NH2 |
| 1065 | H | H | NH2 | 5-Cl | H | OH |
| 1066 | H | H | NH2 | 5-Cl | Me | Me |
| 1067 | H | H | NH2 | 5-Cl | Me | NH2 |
| 1068 | H | H | NH2 | 5-Cl | Me | OH |
| 1069 | H | H | NH2 | 6-Cl | H | Me |
| 1070 | H | H | NH2 | 6-Cl | H | NH2 |
| 1071 | H | H | NH2 | 6-Cl | H | OH |
| 1072 | H | H | NH2 | 6-Cl | Me | Me |
| 1073 | H | H | NH2 | 6-Cl | Me | NH2 |
| 1074 | H | H | NH2 | 6-Cl | Me | OH |
| 1075 | H | H | NH2 | 7-Cl | H | Me |
| 1076 | H | H | NH2 | 7-Cl | H | NH2 |
| 1077 | H | H | NH2 | 7-Cl | H | OH |
| 1078 | H | H | NH2 | 7-Cl | Me | Me |
| 1079 | H | H | NH2 | 7-Cl | Me | NH2 |
| 1080 | H | H | NH2 | 7-Cl | Me | OH |

TABLE 28

| Compound No. | R1 | R2 | R3 | R3' | R4 | R5 |
|---|---|---|---|---|---|---|
| 1081 | H | H | NH2 | 5-NH2 | H | Me |
| 1082 | H | H | NH2 | 5-NH2 | H | NH2 |

TABLE 28-continued

| Compound No. | R1 | R2 | R3 | R3' | R4 | R5 |
|---|---|---|---|---|---|---|
| 1083 | H | H | NH2 | 5-NH2 | H | OH |
| 1084 | H | H | NH2 | 5-NH2 | Me | Me |
| 1085 | H | H | NH2 | 5-NH2 | Me | NH2 |
| 1086 | H | H | NH2 | 5-NH2 | Me | OH |
| 1087 | H | H | NH2 | 6-NH2 | H | Me |
| 1088 | H | H | NH2 | 6-NH2 | H | NH2 |
| 1089 | H | H | NH2 | 6-NH2 | H | OH |
| 1090 | H | H | NH2 | 6-NH2 | Me | Me |
| 1091 | H | H | NH2 | 6-NH2 | Me | NH2 |
| 1092 | H | H | NH2 | 6-NH2 | Me | OH |
| 1093 | H | H | NH2 | 7-NH2 | H | Me |
| 1094 | H | H | NH2 | 7-NH2 | H | NH2 |
| 1095 | H | H | NH2 | 7-NH2 | H | OH |
| 1096 | H | H | NH2 | 7-NH2 | Me | Me |
| 1097 | H | H | NH2 | 7-NH2 | Me | NH2 |
| 1098 | H | H | NH2 | 7-NH2 | Me | OH |
| 1099 | H | H | NH2 | 5-Me | H | Me |
| 1100 | H | H | NH2 | 5-Me | H | NH2 |
| 1101 | H | H | NH2 | 5-Me | H | OH |
| 1102 | H | H | NH2 | 5-Me | Me | Me |
| 1103 | H | H | NH2 | 5-Me | Me | NH2 |
| 1104 | H | H | NH2 | 5-Me | Me | OH |
| 1105 | H | H | NH2 | 6-Me | H | Me |
| 1106 | H | H | NH2 | 6-Me | H | NH2 |
| 1107 | H | H | NH2 | 6-Me | H | OH |
| 1108 | H | H | NH2 | 6-Me | Me | Me |
| 1109 | H | H | NH2 | 6-Me | Me | NH2 |
| 1110 | H | H | NH2 | 6-Me | Me | OH |
| 1111 | H | H | NH2 | 7-Me | H | Me |
| 1112 | H | H | NH2 | 7-Me | H | NH2 |
| 1113 | H | H | NH2 | 7-Me | H | OH |
| 1114 | H | H | NH2 | 7-Me | Me | Me |
| 1115 | H | H | NH2 | 7-Me | Me | NH2 |
| 1116 | H | H | NH2 | 7-Me | Me | OH |
| 1117 | H | H | Me | 5-H | H | Me |
| 1118 | H | H | Me | 5-H | H | NH2 |
| 1119 | H | H | Me | 5-H | H | OH |
| 1120 | H | H | Me | 5-H | Me | Me |

TABLE 29

| Compound No. | R1 | R2 | R3 | R3' | R4 | R5 |
|---|---|---|---|---|---|---|
| 1121 | H | H | Me | 5-H | Me | NH2 |
| 1122 | H | H | Me | 5-H | Me | OH |
| 1123 | H | H | Me | 6-H | H | Me |
| 1124 | H | H | Me | 6-H | H | NH2 |
| 1125 | H | H | Me | 6-H | H | OH |
| 1126 | H | H | Me | 6-H | Me | Me |
| 1127 | H | H | Me | 6-H | Me | NH2 |
| 1128 | H | H | Me | 6-H | Me | OH |
| 1129 | H | H | Me | 7-H | H | Me |
| 1130 | H | H | Me | 7-H | H | NH2 |
| 1131 | H | H | Me | 7-H | H | OH |
| 1132 | H | H | Me | 7-H | Me | Me |
| 1133 | H | H | Me | 7-H | Me | NH2 |
| 1134 | H | H | Me | 7-H | Me | OH |
| 1135 | H | H | Me | 5-Cl | H | Me |
| 1136 | H | H | Me | 5-Cl | H | NH2 |
| 1137 | H | H | Me | 5-Cl | H | OH |
| 1138 | H | H | Me | 5-Cl | Me | Me |
| 1139 | H | H | Me | 5-Cl | Me | NH2 |
| 1140 | H | H | Me | 5-Cl | Me | OH |
| 1141 | H | H | Me | 6-Cl | H | Me |
| 1142 | H | H | Me | 6-Cl | H | NH2 |
| 1143 | H | H | Me | 6-Cl | H | OH |
| 1144 | H | H | Me | 6-Cl | Me | Me |
| 1145 | H | H | Me | 6-Cl | Me | NH2 |
| 1146 | H | H | Me | 6-Cl | Me | OH |
| 1147 | H | H | Me | 7-Cl | H | Me |
| 1148 | H | H | Me | 7-Cl | H | NH2 |
| 1149 | H | H | Me | 7-Cl | H | OH |
| 1150 | H | H | Me | 7-Cl | Me | Me |
| 1151 | H | H | Me | 7-Cl | Me | NH2 |

TABLE 29-continued

| Compound No. | R1 | R2 | R3 | R3' | R4 | R5 |
|---|---|---|---|---|---|---|
| 1152 | H | H | Me | 7-Cl | Me | OH |
| 1153 | H | H | Me | 5-NH2 | H | Me |
| 1154 | H | H | Me | 5-NH2 | H | NH2 |
| 1155 | H | H | Me | 5-NH2 | H | OH |
| 1156 | H | H | Me | 5-NH2 | Me | Me |
| 1157 | H | H | Me | 5-NH2 | Me | NH2 |
| 1158 | H | H | Me | 5-NH2 | Me | OH |
| 1159 | H | H | Me | 6-NH2 | H | Me |
| 1160 | H | H | Me | 6-NH2 | H | NH2 |

TABLE 30

| Compound No. | R1 | R2 | R3 | R3' | R4 | R5 |
|---|---|---|---|---|---|---|
| 1161 | H | H | Me | 6-NH2 | H | OH |
| 1162 | H | H | Me | 6-NH2 | Me | Me |
| 1163 | H | H | Me | 6-NH2 | Me | NH2 |
| 1164 | H | H | Me | 6-NH2 | Me | OH |
| 1165 | H | H | Me | 7-NH2 | H | Me |
| 1166 | H | H | Me | 7-NH2 | H | NH2 |
| 1167 | H | H | Me | 7-NH2 | H | OH |
| 1168 | H | H | Me | 7-NH2 | Me | Me |
| 1169 | H | H | Me | 7-NH2 | Me | NH2 |
| 1170 | H | H | Me | 7-NH2 | Me | OH |
| 1171 | H | H | Me | 5-Me | H | Me |
| 1172 | H | H | Me | 5-Me | H | NH2 |
| 1173 | H | H | Me | 5-Me | H | OH |
| 1174 | H | H | Me | 5-Me | Me | Me |
| 1175 | H | H | Me | 5-Me | Me | NH2 |
| 1176 | H | H | Me | 5-Me | Me | OH |
| 1177 | H | H | Me | 6-Me | H | Me |
| 1178 | H | H | Me | 6-Me | H | NH2 |
| 1179 | H | H | Me | 6-Me | H | OH |
| 1180 | H | H | Me | 6-Me | Me | Me |
| 1181 | H | H | Me | 6-Me | Me | NH2 |
| 1182 | H | H | Me | 6-Me | Me | OH |
| 1183 | H | H | Me | 7-Me | H | Me |
| 1184 | H | H | Me | 7-Me | H | NH2 |
| 1185 | H | H | Me | 7-Me | H | OH |
| 1186 | H | H | Me | 7-Me | Me | Me |
| 1187 | H | H | Me | 7-Me | Me | NH2 |
| 1188 | H | H | Me | 7-Me | Me | OH |
| 1189 | H | H | H | 5-Cl | H | Me |
| 1190 | H | H | H | 5-Cl | H | NH2 |
| 1191 | H | H | H | 5-Cl | H | OH |
| 1192 | H | H | H | 5-Cl | Me | Me |
| 1193 | H | H | H | 5-Cl | Me | NH2 |
| 1194 | H | H | H | 5-Cl | Me | OH |
| 1195 | H | H | H | 6-Cl | H | Me |
| 1196 | H | H | H | 6-Cl | H | NH2 |
| 1197 | H | H | H | 6-Cl | H | OH |
| 1198 | H | H | H | 6-Cl | Me | Me |
| 1199 | H | H | H | 6-Cl | Me | NH2 |
| 1200 | H | H | H | 6-Cl | Me | OH |

TABLE 31

| Compound No. | R1 | R2 | R3 | R3' | R4 | R5 |
|---|---|---|---|---|---|---|
| 1201 | H | H | H | 7-Cl | H | Me |
| 1202 | H | H | H | 7-Cl | H | NH2 |
| 1203 | H | H | H | 7-Cl | H | OH |
| 1204 | H | H | H | 7-Cl | Me | Me |
| 1205 | H | H | H | 7-Cl | Me | NH2 |
| 1206 | H | H | H | 7-Cl | Me | OH |
| 1207 | H | H | H | 5-NH2 | H | Me |
| 1208 | H | H | H | 5-NH2 | H | NH2 |
| 1209 | H | H | H | 5-NH2 | H | OH |
| 1210 | H | H | H | 5-NH2 | Me | Me |
| 1211 | H | H | H | 5-NH2 | Me | NH2 |
| 1212 | H | H | H | 5-NH2 | Me | OH |
| 1213 | H | H | H | 6-NH2 | H | Me |

TABLE 31-continued

| Compound No. | R1 | R2 | R3 | R3' | R4 | R5 |
|---|---|---|---|---|---|---|
| 1214 | H | H | H | 6-NH2 | H | NH2 |
| 1215 | H | H | H | 6-NH2 | H | OH |
| 1216 | H | H | H | 6-NH2 | Me | Me |
| 1217 | H | H | H | 6-NH2 | Me | NH2 |
| 1218 | H | H | H | 6-NH2 | Me | OH |
| 1219 | H | H | H | 7-NH2 | H | Me |
| 1220 | H | H | H | 7-NH2 | H | NH2 |
| 1221 | H | H | H | 7-NH2 | H | OH |
| 1222 | H | H | H | 7-NH2 | Me | Me |
| 1223 | H | H | H | 7-NH2 | Me | NH2 |
| 1224 | H | H | H | 7-NH2 | Me | OH |
| 1225 | H | H | H | 5-Me | H | Me |
| 1226 | H | H | H | 5-Me | H | NH2 |
| 1227 | H | H | H | 5-Me | H | OH |
| 1228 | H | H | H | 5-Me | Me | Me |
| 1229 | H | H | H | 5-Me | Me | NH2 |
| 1230 | H | H | H | 5-Me | Me | OH |
| 1231 | H | H | H | 6-Me | H | Me |
| 1232 | H | H | H | 6-Me | H | NH2 |
| 1233 | H | H | H | 6-Me | H | OH |
| 1234 | H | H | H | 6-Me | Me | Me |
| 1235 | H | H | H | 6-Me | Me | NH2 |
| 1236 | H | H | H | 6-Me | Me | OH |
| 1237 | H | H | H | 7-Me | H | Me |
| 1238 | H | H | H | 7-Me | H | NH2 |
| 1239 | H | H | H | 7-Me | H | OH |
| 1240 | H | H | H | 7-Me | Me | Me |

TABLE 32

| Compound No. | R1 | R2 | R3 | R3' | R4 | R5 |
|---|---|---|---|---|---|---|
| 1241 | H | H | H | 7-Me | Me | NH2 |
| 1242 | H | H | H | 7-Me | Me | OH |
| 1243 | H | OMe | Cl | 5-H | H | Me |
| 1244 | H | OMe | Cl | 5-H | H | NH2 |
| 1245 | H | OMe | Cl | 5-H | H | OH |
| 1246 | H | OMe | Cl | 5-H | Me | Me |
| 1247 | H | OMe | Cl | 5-H | Me | NH2 |
| 1248 | H | OMe | Cl | 5-H | Me | OH |
| 1249 | H | OMe | Cl | 6-H | H | Me |
| 1250 | H | OMe | Cl | 6-H | H | NH2 |
| 1251 | H | OMe | Cl | 6-H | H | OH |
| 1252 | H | OMe | Cl | 6-H | Me | Me |
| 1253 | H | OMe | Cl | 6-H | Me | NH2 |
| 1254 | H | OMe | Cl | 6-H | Me | OH |
| 1255 | H | OMe | Cl | 7-H | H | Me |
| 1256 | H | OMe | Cl | 7-H | H | NH2 |
| 1257 | H | OMe | Cl | 7-H | H | OH |
| 1258 | H | OMe | Cl | 7-H | Me | Me |
| 1259 | H | OMe | Cl | 7-H | Me | NH2 |
| 1260 | H | OMe | Cl | 7-H | Me | OH |
| 1261 | H | OMe | Cl | 5-Cl | H | Me |
| 1262 | H | OMe | Cl | 5-Cl | H | NH2 |
| 1263 | H | OMe | Cl | 5-Cl | H | OH |
| 1264 | H | OMe | Cl | 5-Cl | Me | Me |
| 1265 | H | OMe | Cl | 5-Cl | Me | NH2 |
| 1266 | H | OMe | Cl | 5-Cl | Me | OH |
| 1267 | H | OMe | Cl | 6-Cl | H | Me |
| 1268 | H | OMe | Cl | 6-Cl | H | NH2 |
| 1269 | H | OMe | Cl | 6-Cl | H | OH |
| 1270 | H | OMe | Cl | 6-Cl | Me | Me |
| 1271 | H | OMe | Cl | 6-Cl | Me | NH2 |
| 1272 | H | OMe | Cl | 6-Cl | Me | OH |
| 1273 | H | OMe | Cl | 7-Cl | H | Me |
| 1274 | H | OMe | Cl | 7-Cl | H | NH2 |
| 1275 | H | OMe | Cl | 7-Cl | H | OH |
| 1276 | H | OMe | Cl | 7-Cl | Me | Me |
| 1277 | H | OMe | Cl | 7-Cl | Me | NH2 |
| 1278 | H | OMe | Cl | 7-Cl | Me | OH |
| 1279 | H | OMe | Cl | 5-NH2 | H | Me |
| 1280 | H | OMe | Cl | 5-NH2 | H | NH2 |

TABLE 33

| Compound No. | R1 | R2 | R3 | R3' | R4 | R5 |
|---|---|---|---|---|---|---|
| 1281 | H | OMe | Cl | 5-NH2 | H | OH |
| 1282 | H | OMe | Cl | 5-NH2 | Me | Me |
| 1283 | H | OMe | Cl | 5-NH2 | Me | NH2 |
| 1284 | H | OMe | Cl | 5-NH2 | Me | OH |
| 1285 | H | OMe | Cl | 6-NH2 | H | Me |
| 1286 | H | OMe | Cl | 6-NH2 | H | NH2 |
| 1287 | H | OMe | Cl | 6-NH2 | H | OH |
| 1288 | H | OMe | Cl | 6-NH2 | Me | Me |
| 1289 | H | OMe | Cl | 6-NH2 | Me | NH2 |
| 1290 | H | OMe | Cl | 6-NH2 | Me | OH |
| 1291 | H | OMe | Cl | 7-NH2 | H | Me |
| 1292 | H | OMe | Cl | 7-NH2 | H | NH2 |
| 1293 | H | OMe | Cl | 7-NH2 | H | OH |
| 1294 | H | OMe | Cl | 7-NH2 | Me | Me |
| 1295 | H | OMe | Cl | 7-NH2 | Me | NH2 |
| 1296 | H | OMe | Cl | 7-NH2 | Me | OH |
| 1297 | H | OMe | Cl | 5-Me | H | Me |
| 1298 | H | OMe | Cl | 5-Me | H | NH2 |
| 1299 | H | OMe | Cl | 5-Me | H | OH |
| 1300 | H | OMe | Cl | 5-Me | Me | Me |
| 1301 | H | OMe | Cl | 5-Me | Me | NH2 |
| 1302 | H | OMe | Cl | 5-Me | Me | OH |
| 1303 | H | OMe | Cl | 6-Me | H | Me |
| 1304 | H | OMe | Cl | 6-Me | H | NH2 |
| 1305 | H | OMe | Cl | 6-Me | H | OH |
| 1306 | H | OMe | Cl | 6-Me | Me | Me |
| 1307 | H | OMe | Cl | 6-Me | Me | NH2 |
| 1308 | H | OMe | Cl | 6-Me | Me | OH |
| 1309 | H | OMe | Cl | 7-Me | H | Me |
| 1310 | H | OMe | Cl | 7-Me | H | NH2 |
| 1311 | H | OMe | Cl | 7-Me | H | OH |
| 1312 | H | OMe | Cl | 7-Me | Me | Me |
| 1313 | H | OMe | Cl | 7-Me | Me | NH2 |
| 1314 | H | OMe | Cl | 7-Me | Me | OH |
| 1315 | H | OMe | NH2 | 5-H | H | Me |
| 1316 | H | OMe | NH2 | 5-H | H | NH2 |
| 1317 | H | OMe | NH2 | 5-H | H | OH |
| 1318 | H | OMe | NH2 | 5-H | Me | Me |
| 1319 | H | OMe | NH2 | 5-H | Me | NH2 |
| 1320 | H | OMe | NH2 | 5-H | Me | OH |

TABLE 34

| Compound No. | R1 | R2 | R3 | R3' | R4 | R5 |
|---|---|---|---|---|---|---|
| 1321 | H | OMe | NH2 | 6-H | H | Me |
| 1322 | H | OMe | NH2 | 6-H | H | NH2 |
| 1323 | H | OMe | NH2 | 6-H | H | OH |
| 1324 | H | OMe | NH2 | 6-H | Me | Me |
| 1325 | H | OMe | NH2 | 6-H | Me | NH2 |
| 1326 | H | OMe | NH2 | 6-H | Me | OH |
| 1327 | H | OMe | NH2 | 7-H | H | Me |
| 1328 | H | OMe | NH2 | 7-H | H | NH2 |
| 1329 | H | OMe | NH2 | 7-H | H | OH |
| 1330 | H | OMe | NH2 | 7-H | Me | Me |
| 1331 | H | OMe | NH2 | 7-H | Me | NH2 |
| 1332 | H | OMe | NH2 | 7-H | Me | OH |
| 1333 | H | OMe | NH2 | 5-Cl | H | Me |
| 1334 | H | OMe | NH2 | 5-Cl | H | NH2 |
| 1335 | H | OMe | NH2 | 5-Cl | H | OH |
| 1336 | H | OMe | NH2 | 5-Cl | Me | Me |
| 1337 | H | OMe | NH2 | 5-Cl | Me | NH2 |
| 1338 | H | OMe | NH2 | 5-Cl | Me | OH |
| 1339 | H | OMe | NH2 | 6-Cl | H | Me |
| 1340 | H | OMe | NH2 | 6-Cl | H | NH2 |
| 1341 | H | OMe | NH2 | 6-Cl | H | OH |
| 1342 | H | OMe | NH2 | 6-Cl | Me | Me |
| 1343 | H | OMe | NH2 | 6-Cl | Me | NH2 |
| 1344 | H | OMe | NH2 | 6-Cl | Me | OH |
| 1345 | H | OMe | NH2 | 7-Cl | H | Me |
| 1346 | H | OMe | NH2 | 7-Cl | H | NH2 |
| 1347 | H | OMe | NH2 | 7-Cl | H | OH |
| 1348 | H | OMe | NH2 | 7-Cl | Me | Me |
| 1349 | H | OMe | NH2 | 7-Cl | Me | NH2 |

TABLE 34-continued

| Compound No. | R1 | R2 | R3 | R3' | R4 | R5 |
|---|---|---|---|---|---|---|
| 1350 | H | OMe | NH2 | 7-Cl | Me | OH |
| 1351 | H | OMe | NH2 | 5-NH2 | H | Me |
| 1352 | H | OMe | NH2 | 5-NH2 | H | NH2 |
| 1353 | H | OMe | NH2 | 5-NH2 | H | OH |
| 1354 | H | OMe | NH2 | 5-NH2 | Me | Me |
| 1355 | H | OMe | NH2 | 5-NH2 | Me | NH2 |
| 1356 | H | OMe | NH2 | 5-NH2 | Me | OH |
| 1357 | H | OMe | NH2 | 6-NH2 | H | Me |
| 1358 | H | OMe | NH2 | 6-NH2 | H | NH2 |
| 1359 | H | OMe | NH2 | 6-NH2 | H | OH |
| 1360 | H | OMe | NH2 | 6-NH2 | Me | Me |

TABLE 35

| Compound No. | R1 | R2 | R3 | R3' | R4 | R5 |
|---|---|---|---|---|---|---|
| 1361 | H | OMe | NH2 | 6-NH2 | Me | NH2 |
| 1362 | H | OMe | NH2 | 6-NH2 | Me | OH |
| 1363 | H | OMe | NH2 | 7-NH2 | H | Me |
| 1364 | H | OMe | NH2 | 7-NH2 | H | NH2 |
| 1365 | H | OMe | NH2 | 7-NH2 | H | OH |
| 1366 | H | OMe | NH2 | 7-NH2 | Me | Me |
| 1367 | H | OMe | NH2 | 7-NH2 | Me | NH2 |
| 1368 | H | OMe | NH2 | 7-NH2 | Me | OH |
| 1369 | H | OMe | NH2 | 5-Me | H | Me |
| 1370 | H | OMe | NH2 | 5-Me | H | NH2 |
| 1371 | H | OMe | NH2 | 5-Me | H | OH |
| 1372 | H | OMe | NH2 | 5-Me | Me | Me |
| 1373 | H | OMe | NH2 | 5-Me | Me | NH2 |
| 1374 | H | OMe | NH2 | 5-Me | Me | OH |
| 1375 | H | OMe | NH2 | 6-Me | H | Me |
| 1376 | H | OMe | NH2 | 6-Me | H | NH2 |
| 1377 | H | OMe | NH2 | 6-Me | H | OH |
| 1378 | H | OMe | NH2 | 6-Me | Me | Me |
| 1379 | H | OMe | NH2 | 6-Me | Me | NH2 |
| 1380 | H | OMe | NH2 | 6-Me | Me | OH |
| 1381 | H | OMe | NH2 | 7-Me | H | Me |
| 1382 | H | OMe | NH2 | 7-Me | H | NH2 |
| 1383 | H | OMe | NH2 | 7-Me | H | OH |
| 1384 | H | OMe | NH2 | 7-Me | Me | Me |
| 1385 | H | OMe | NH2 | 7-Me | Me | NH2 |
| 1386 | H | OMe | NH2 | 7-Me | Me | OH |
| 1387 | H | OMe | Me | 5-H | H | Me |
| 1388 | H | OMe | Me | 5-H | H | NH2 |
| 1389 | H | OMe | Me | 5-H | H | OH |
| 1390 | H | OMe | Me | 5-H | Me | Me |
| 1391 | H | OMe | Me | 5-H | Me | NH2 |
| 1392 | H | OMe | Me | 5-H | Me | OH |
| 1393 | H | OMe | Me | 6-H | H | Me |
| 1394 | H | OMe | Me | 6-H | H | NH2 |
| 1395 | H | OMe | Me | 6-H | H | OH |
| 1396 | H | OMe | Me | 6-H | Me | Me |
| 1397 | H | OMe | Me | 6-H | Me | NH2 |
| 1398 | H | OMe | Me | 6-H | Me | OH |
| 1399 | H | OMe | Me | 7-H | H | Me |
| 1400 | H | OMe | Me | 7-H | H | NH2 |

TABLE 36

| Compound No. | R1 | R2 | R3 | R3' | R4 | R5 |
|---|---|---|---|---|---|---|
| 1401 | H | OMe | Me | 7-H | H | OH |
| 1402 | H | OMe | Me | 7-H | Me | Me |
| 1403 | H | OMe | Me | 7-H | Me | NH2 |
| 1404 | H | OMe | Me | 7-H | Me | OH |
| 1405 | H | OMe | Me | 5-Cl | H | Me |
| 1406 | H | OMe | Me | 5-Cl | H | NH2 |
| 1407 | H | OMe | Me | 5-Cl | H | OH |
| 1408 | H | OMe | Me | 5-Cl | Me | Me |
| 1409 | H | OMe | Me | 5-Cl | Me | NH2 |
| 1410 | H | OMe | Me | 5-Cl | Me | OH |
| 1411 | H | OMe | Me | 6-Cl | H | Me |

TABLE 36-continued

| Compound No. | R1 | R2 | R3 | R3' | R4 | R5 |
|---|---|---|---|---|---|---|
| 1412 | H | OMe | Me | 6-Cl | H | NH2 |
| 1413 | H | OMe | Me | 6-Cl | H | OH |
| 1414 | H | OMe | Me | 6-Cl | Me | Me |
| 1415 | H | OMe | Me | 6-Cl | Me | NH2 |
| 1416 | H | OMe | Me | 6-Cl | Me | OH |
| 1417 | H | OMe | Me | 7-Cl | H | Me |
| 1418 | H | OMe | Me | 7-Cl | H | NH2 |
| 1419 | H | OMe | Me | 7-Cl | H | OH |
| 1420 | H | OMe | Me | 7-Cl | Me | Me |
| 1421 | H | OMe | Me | 7-Cl | Me | NH2 |
| 1422 | H | OMe | Me | 7-Cl | Me | OH |
| 1423 | H | OMe | Me | 5-NH2 | H | Me |
| 1424 | H | OMe | Me | 5-NH2 | H | NH2 |
| 1425 | H | OMe | Me | 5-NH2 | H | OH |
| 1426 | H | OMe | Me | 5-NH2 | Me | Me |
| 1427 | H | OMe | Me | 5-NH2 | Me | NH2 |
| 1428 | H | OMe | Me | 5-NH2 | Me | OH |
| 1429 | H | OMe | Me | 6-NH2 | H | Me |
| 1430 | H | OMe | Me | 6-NH2 | H | NH2 |
| 1431 | H | OMe | Me | 6-NH2 | H | OH |
| 1432 | H | OMe | Me | 6-NH2 | Me | Me |
| 1433 | H | OMe | Me | 6-NH2 | Me | NH2 |
| 1434 | H | OMe | Me | 6-NH2 | Me | OH |
| 1435 | H | OMe | Me | 7-NH2 | H | Me |
| 1436 | H | OMe | Me | 7-NH2 | H | NH2 |
| 1437 | H | OMe | Me | 7-NH2 | H | OH |
| 1438 | H | OMe | Me | 7-NH2 | Me | Me |
| 1439 | H | OMe | Me | 7-NH2 | Me | NH2 |
| 1440 | H | OMe | Me | 7-NH2 | Me | OH |

TABLE 37

| Compound No. | R1 | R2 | R3 | R3' | R4 | R5 |
|---|---|---|---|---|---|---|
| 1441 | H | OMe | Me | 5-Me | H | Me |
| 1442 | H | OMe | Me | 5-Me | H | NH2 |
| 1443 | H | OMe | Me | 5-Me | H | OH |
| 1444 | H | OMe | Me | 5-Me | Me | Me |
| 1445 | H | OMe | Me | 5-Me | Me | NH2 |
| 1446 | H | OMe | Me | 5-Me | Me | OH |
| 1447 | H | OMe | Me | 6-Me | H | Me |
| 1448 | H | OMe | Me | 6-Me | H | NH2 |
| 1449 | H | OMe | Me | 6-Me | H | OH |
| 1450 | H | OMe | Me | 6-Me | Me | Me |
| 1451 | H | OMe | Me | 6-Me | Me | NH2 |
| 1452 | H | OMe | Me | 6-Me | Me | OH |
| 1453 | H | OMe | Me | 7-Me | H | Me |
| 1454 | H | OMe | Me | 7-Me | H | NH2 |
| 1455 | H | OMe | Me | 7-Me | H | OH |
| 1456 | H | OMe | Me | 7-Me | Me | Me |
| 1457 | H | OMe | Me | 7-Me | Me | NH2 |
| 1458 | H | OMe | Me | 7-Me | Me | OH |
| 1459 | H | OMe | H | 5-Cl | H | Me |
| 1460 | H | OMe | H | 5-Cl | H | NH2 |
| 1461 | H | OMe | H | 5-Cl | H | OH |
| 1462 | H | OMe | H | 5-Cl | Me | Me |
| 1463 | H | OMe | H | 5-Cl | Me | NH2 |
| 1464 | H | OMe | H | 5-Cl | Me | OH |
| 1465 | H | OMe | H | 6-Cl | H | Me |
| 1466 | H | OMe | H | 6-Cl | H | NH2 |
| 1467 | H | OMe | H | 6-Cl | H | OH |
| 1468 | H | OMe | H | 6-Cl | Me | Me |
| 1469 | H | OMe | H | 6-Cl | Me | NH2 |
| 1470 | H | OMe | H | 6-Cl | Me | OH |
| 1471 | H | OMe | H | 7-Cl | H | Me |
| 1472 | H | OMe | H | 7-Cl | H | NH2 |
| 1473 | H | OMe | H | 7-Cl | H | OH |
| 1474 | H | OMe | H | 7-Cl | Me | Me |
| 1475 | H | OMe | H | 7-Cl | Me | NH2 |
| 1476 | H | OMe | H | 7-Cl | Me | OH |
| 1477 | H | OMe | H | 5-NH2 | H | Me |
| 1478 | H | OMe | H | 5-NH2 | H | NH2 |

TABLE 37-continued

| Compound No. | R1 | R2 | R3 | R3' | R4 | R5 |
|---|---|---|---|---|---|---|
| 1479 | H | OMe | H | 5-NH2 | H | OH |
| 1480 | H | OMe | H | 5-NH2 | Me | Me |

TABLE 38

| Compound No. | R1 | R2 | R3 | R3' | R4 | R5 |
|---|---|---|---|---|---|---|
| 1481 | H | OMe | H | 5-NH2 | Me | NH2 |
| 1482 | H | OMe | H | 5-NH2 | Me | OH |
| 1483 | H | OMe | H | 6-NH2 | H | Me |
| 1484 | H | OMe | H | 6-NH2 | H | NH2 |
| 1485 | H | OMe | H | 6-NH2 | H | OH |
| 1486 | H | OMe | H | 6-NH2 | Me | Me |
| 1487 | H | OMe | H | 6-NH2 | Me | NH2 |
| 1488 | H | OMe | H | 6-NH2 | Me | OH |
| 1489 | H | OMe | H | 7-NH2 | H | Me |
| 1490 | H | OMe | H | 7-NH2 | H | NH2 |
| 1491 | H | OMe | H | 7-NH2 | H | OH |
| 1492 | H | OMe | H | 7-NH2 | Me | Me |
| 1493 | H | OMe | H | 7-NH2 | Me | NH2 |
| 1494 | H | OMe | H | 7-NH2 | Me | OH |
| 1495 | H | OMe | H | 5-Me | H | Me |
| 1496 | H | OMe | H | 5-Me | H | NH2 |
| 1497 | H | OMe | H | 5-Me | H | OH |
| 1498 | H | OMe | H | 5-Me | Me | Me |
| 1499 | H | OMe | H | 5-Me | Me | NH2 |
| 1500 | H | OMe | H | 5-Me | Me | OH |
| 1501 | H | OMe | H | 6-Me | H | Me |
| 1502 | H | OMe | H | 6-Me | H | NH2 |
| 1503 | H | OMe | H | 6-Me | H | OH |
| 1504 | H | OMe | H | 6-Me | Me | Me |
| 1505 | H | OMe | H | 6-Me | Me | NH2 |
| 1506 | H | OMe | H | 6-Me | Me | OH |
| 1507 | H | OMe | H | 7-Me | H | Me |
| 1508 | H | OMe | H | 7-Me | H | NH2 |
| 1509 | H | OMe | H | 7-Me | H | OH |
| 1510 | H | OMe | H | 7-Me | Me | Me |
| 1511 | H | OMe | H | 7-Me | Me | NH2 |
| 1512 | H | OMe | H | 7-Me | Me | OH |
| 1513 | 2-thienylethyl | H | Cl | 5-H | H | Me |
| 1514 | 2-thienylethyl | H | Cl | 5-H | H | NH2 |
| 1515 | 2-thienylethyl | H | Cl | 5-H | H | OH |
| 1516 | 2-thienylethyl | H | Cl | 5-H | Me | Me |
| 1517 | 2-thienylethyl | H | Cl | 5-H | Me | NH2 |
| 1518 | 2-thienylethyl | H | Cl | 5-H | Me | OH |
| 1519 | 2-thienylethyl | H | Cl | 6-H | H | Me |
| 1520 | 2-thienylethyl | H | Cl | 6-H | H | NH2 |

TABLE 39

| Compound No. | R1 | R2 | R3 | R3' | R4 | R5 |
|---|---|---|---|---|---|---|
| 1521 | 2-thienylethyl | H | Cl | 6-H | H | OH |
| 1522 | 2-thienylethyl | H | Cl | 6-H | Me | Me |
| 1523 | 2-thienylethyl | H | Cl | 6-H | Me | NH2 |
| 1524 | 2-thienylethyl | H | Cl | 6-H | Me | OH |
| 1525 | 2-thienylethyl | H | Cl | 7-H | H | Me |
| 1526 | 2-thienylethyl | H | Cl | 7-H | H | NH2 |
| 1527 | 2-thienylethyl | H | Cl | 7-H | H | OH |
| 1528 | 2-thienylethyl | H | Cl | 7-H | Me | Me |
| 1529 | 2-thienylethyl | H | Cl | 7-H | Me | NH2 |
| 1530 | 2-thienylethyl | H | Cl | 7-H | Me | OH |
| 1531 | 2-thienylethyl | H | Cl | 5-Cl | H | Me |
| 1532 | 2-thienylethyl | H | Cl | 5-Cl | H | NH2 |
| 1533 | 2-thienylethyl | H | Cl | 5-Cl | H | OH |
| 1534 | 2-thienylethyl | H | Cl | 5-Cl | Me | Me |
| 1535 | 2-thienylethyl | H | Cl | 5-Cl | Me | NH2 |
| 1536 | 2-thienylethyl | H | Cl | 5-Cl | Me | OH |
| 1537 | 2-thienylethyl | H | Cl | 6-Cl | H | Me |
| 1538 | 2-thienylethyl | H | Cl | 6-Cl | H | NH2 |
| 1539 | 2-thienylethyl | H | Cl | 6-Cl | H | OH |
| 1540 | 2-thienylethyl | H | Cl | 6-Cl | Me | Me |

TABLE 39-continued

| Compound No. | R1 | R2 | R3 | R3' | R4 | R5 |
|---|---|---|---|---|---|---|
| 1541 | 2-thienylethyl | H | Cl | 6-Cl | Me | NH2 |
| 1542 | 2-thienylethyl | H | Cl | 6-Cl | Me | OH |
| 1543 | 2-thienylethyl | H | Cl | 7-Cl | H | Me |
| 1544 | 2-thienylethyl | H | Cl | 7-Cl | H | NH2 |
| 1545 | 2-thienylethyl | H | Cl | 7-Cl | H | OH |
| 1546 | 2-thienylethyl | H | Cl | 7-Cl | Me | Me |
| 1547 | 2-thienylethyl | H | Cl | 7-Cl | Me | NH2 |
| 1548 | 2-thienylethyl | H | Cl | 7-Cl | Me | OH |
| 1549 | 2-thienylethyl | H | Cl | 5-NH2 | H | Me |
| 1550 | 2-thienylethyl | H | Cl | 5-NH2 | H | NH2 |
| 1551 | 2-thienylethyl | H | Cl | 5-NH2 | H | OH |
| 1552 | 2-thienylethyl | H | Cl | 5-NH2 | Me | Me |
| 1553 | 2-thienylethyl | H | Cl | 5-NH2 | Me | NH2 |
| 1554 | 2-thienylethyl | H | Cl | 5-NH2 | Me | OH |
| 1555 | 2-thienylethyl | H | Cl | 6-NH2 | H | Me |
| 1556 | 2-thienylethyl | H | Cl | 6-NH2 | H | NH2 |
| 1557 | 2-thienylethyl | H | Cl | 6-NH2 | H | OH |
| 1558 | 2-thienylethyl | H | Cl | 6-NH2 | Me | Me |
| 1559 | 2-thienylethyl | H | Cl | 6-NH2 | Me | NH2 |
| 1560 | 2-thienylethyl | H | Cl | 6-NH2 | Me | OH |

TABLE 40

| Compound No. | R1 | R2 | R3 | R3' | R4 | R5 |
|---|---|---|---|---|---|---|
| 1561 | 2-thienylethyl | H | Cl | 7-NH2 | H | Me |
| 1562 | 2-thienylethyl | H | Cl | 7-NH2 | H | NH2 |
| 1563 | 2-thienylethyl | H | Cl | 7-NH2 | H | OH |
| 1564 | 2-thienylethyl | H | Cl | 7-NH2 | Me | Me |
| 1565 | 2-thienylethyl | H | Cl | 7-NH2 | Me | NH2 |
| 1566 | 2-thienylethyl | H | Cl | 7-NH2 | Me | OH |
| 1567 | 2-thienylethyl | H | Cl | 5-Me | H | Me |
| 1568 | 2-thienylethyl | H | Cl | 5-Me | H | NH2 |
| 1569 | 2-thienylethyl | H | Cl | 5-Me | H | OH |
| 1570 | 2-thienylethyl | H | Cl | 5-Me | Me | Me |
| 1571 | 2-thienylethyl | H | Cl | 5-Me | Me | NH2 |
| 1572 | 2-thienylethyl | H | Cl | 5-Me | Me | OH |
| 1573 | 2-thienylethyl | H | Cl | 6-Me | H | Me |
| 1574 | 2-thienylethyl | H | Cl | 6-Me | H | NH2 |
| 1575 | 2-thienylethyl | H | Cl | 6-Me | H | OH |
| 1576 | 2-thienylethyl | H | Cl | 6-Me | Me | Me |
| 1577 | 2-thienylethyl | H | Cl | 6-Me | Me | NH2 |
| 1578 | 2-thienylethyl | H | Cl | 6-Me | Me | OH |
| 1579 | 2-thienylethyl | H | Cl | 7-Me | H | Me |
| 1580 | 2-thienylethyl | H | Cl | 7-Me | H | NH2 |
| 1581 | 2-thienylethyl | H | Cl | 7-Me | H | OH |
| 1582 | 2-thienylethyl | H | Cl | 7-Me | Me | Me |
| 1583 | 2-thienylethyl | H | Cl | 7-Me | Me | NH2 |
| 1584 | 2-thienylethyl | H | Cl | 7-Me | Me | OH |
| 1585 | 2-thienylethyl | H | NH2 | 5-H | H | Me |
| 1586 | 2-thienylethyl | H | NH2 | 5-H | H | NH2 |
| 1587 | 2-thienylethyl | H | NH2 | 5-H | H | OH |
| 1588 | 2-thienylethyl | H | NH2 | 5-H | Me | Me |
| 1589 | 2-thienylethyl | H | NH2 | 5-H | Me | NH2 |
| 1590 | 2-thienylethyl | H | NH2 | 5-H | Me | OH |
| 1591 | 2-thienylethyl | H | NH2 | 6-H | H | Me |
| 1592 | 2-thienylethyl | H | NH2 | 6-H | H | NH2 |
| 1593 | 2-thienylethyl | H | NH2 | 6-H | H | OH |
| 1594 | 2-thienylethyl | H | NH2 | 6-H | Me | Me |
| 1595 | 2-thienylethyl | H | NH2 | 6-H | Me | NH2 |
| 1596 | 2-thienylethyl | H | NH2 | 6-H | Me | OH |
| 1597 | 2-thienylethyl | H | NH2 | 7-H | H | Me |
| 1598 | 2-thienylethyl | H | NH2 | 7-H | H | NH2 |
| 1599 | 2-thienylethyl | H | NH2 | 7-H | H | OH |
| 1600 | 2-thienylethyl | H | NH2 | 7-H | Me | Me |

TABLE 41

| Compound No. | R1 | R2 | R3 | R3' | R4 | R5 |
|---|---|---|---|---|---|---|
| 1601 | 2-thienylethyl | H | NH2 | 7-H | Me | NH2 |
| 1602 | 2-thienylethyl | H | NH2 | 7-H | Me | OH |

TABLE 41-continued

| Compound No. | R1 | R2 | R3 | R3' | R4 | R5 |
|---|---|---|---|---|---|---|
| 1603 | 2-thienylethyl | H | NH2 | 5-Cl | H | Me |
| 1604 | 2-thienylethyl | H | NH2 | 5-Cl | H | NH2 |
| 1605 | 2-thienylethyl | H | NH2 | 5-Cl | H | OH |
| 1606 | 2-thienylethyl | H | NH2 | 5-Cl | Me | Me |
| 1607 | 2-thienylethyl | H | NH2 | 5-Cl | Me | NH2 |
| 1608 | 2-thienylethyl | H | NH2 | 5-Cl | Me | OH |
| 1609 | 2-thienylethyl | H | NH2 | 6-Cl | H | Me |
| 1610 | 2-thienylethyl | H | NH2 | 6-Cl | H | NH2 |
| 1611 | 2-thienylethyl | H | NH2 | 6-Cl | H | OH |
| 1612 | 2-thienylethyl | H | NH2 | 6-Cl | Me | Me |
| 1613 | 2-thienylethyl | H | NH2 | 6-Cl | Me | NH2 |
| 1614 | 2-thienylethyl | H | NH2 | 6-Cl | Me | OH |
| 1615 | 2-thienylethyl | H | NH2 | 7-Cl | H | Me |
| 1616 | 2-thienylethyl | H | NH2 | 7-Cl | H | NH2 |
| 1617 | 2-thienylethyl | H | NH2 | 7-Cl | H | OH |
| 1618 | 2-thienylethyl | H | NH2 | 7-Cl | Me | Me |
| 1619 | 2-thienylethyl | H | NH2 | 7-Cl | Me | NH2 |
| 1620 | 2-thienylethyl | H | NH2 | 7-Cl | Me | OH |
| 1621 | 2-thienylethyl | H | NH2 | 5-NH2 | H | Me |
| 1622 | 2-thienylethyl | H | NH2 | 5-NH2 | H | NH2 |
| 1623 | 2-thienylethyl | H | NH2 | 5-NH2 | H | OH |
| 1624 | 2-thienylethyl | H | NH2 | 5-NH2 | Me | Me |
| 1625 | 2-thienylethyl | H | NH2 | 5-NH2 | Me | NH2 |
| 1626 | 2-thienylethyl | H | NH2 | 5-NH2 | Me | OH |
| 1627 | 2-thienylethyl | H | NH2 | 6-NH2 | H | Me |
| 1628 | 2-thienylethyl | H | NH2 | 6-NH2 | H | NH2 |
| 1629 | 2-thienylethyl | H | NH2 | 6-NH2 | H | OH |
| 1630 | 2-thienylethyl | H | NH2 | 6-NH2 | Me | Me |
| 1631 | 2-thienylethyl | H | NH2 | 6-NH2 | Me | NH2 |
| 1632 | 2-thienylethyl | H | NH2 | 6-NH2 | Me | OH |
| 1633 | 2-thienylethyl | H | NH2 | 7-NH2 | H | Me |
| 1634 | 2-thienylethyl | H | NH2 | 7-NH2 | H | NH2 |
| 1635 | 2-thienylethyl | H | NH2 | 7-NH2 | H | OH |
| 1636 | 2-thienylethyl | H | NH2 | 7-NH2 | Me | Me |
| 1637 | 2-thienylethyl | H | NH2 | 7-NH2 | Me | NH2 |
| 1638 | 2-thienylethyl | H | NH2 | 7-NH2 | Me | OH |
| 1639 | 2-thienylethyl | H | NH2 | 5-Me | H | Me |
| 1640 | 2-thienylethyl | H | NH2 | 5-Me | H | NH2 |

TABLE 42

| Compound No. | R1 | R2 | R3 | R3' | R4 | R5 |
|---|---|---|---|---|---|---|
| 1641 | 2-thienylethyl | H | NH2 | 5-Me | H | OH |
| 1642 | 2-thienylethyl | H | NH2 | 5-Me | Me | Me |
| 1643 | 2-thienylethyl | H | NH2 | 5-Me | Me | NH2 |
| 1644 | 2-thienylethyl | H | NH2 | 5-Me | Me | OH |
| 1645 | 2-thienylethyl | H | NH2 | 6-Me | H | Me |
| 1646 | 2-thienylethyl | H | NH2 | 6-Me | H | NH2 |
| 1647 | 2-thienylethyl | H | NH2 | 6-Me | H | OH |
| 1648 | 2-thienylethyl | H | NH2 | 6-Me | Me | Me |
| 1649 | 2-thienylethyl | H | NH2 | 6-Me | Me | NH2 |
| 1650 | 2-thienylethyl | H | NH2 | 6-Me | Me | OH |
| 1651 | 2-thienylethyl | H | NH2 | 7-Me | H | Me |
| 1652 | 2-thienylethyl | H | NH2 | 7-Me | H | NH2 |
| 1653 | 2-thienylethyl | H | NH2 | 7-Me | H | OH |
| 1654 | 2-thienylethyl | H | NH2 | 7-Me | Me | Me |
| 1655 | 2-thienylethyl | H | NH2 | 7-Me | Me | NH2 |
| 1656 | 2-thienylethyl | H | NH2 | 7-Me | Me | OH |
| 1657 | 2-thienylethyl | H | Me | 5-H | H | Me |
| 1658 | 2-thienylethyl | H | Me | 5-H | H | NH2 |
| 1659 | 2-thienylethyl | H | Me | 5-H | H | OH |
| 1660 | 2-thienylethyl | H | Me | 5-H | Me | Me |
| 1661 | 2-thienylethyl | H | Me | 5-H | Me | NH2 |
| 1662 | 2-thienylethyl | H | Me | 5-H | Me | OH |
| 1663 | 2-thienylethyl | H | Me | 6-H | H | Me |
| 1664 | 2-thienylethyl | H | Me | 6-H | H | NH2 |
| 1665 | 2-thienylethyl | H | Me | 6-H | H | OH |
| 1666 | 2-thienylethyl | H | Me | 6-H | Me | Me |
| 1667 | 2-thienylethyl | H | Me | 6-H | Me | NH2 |
| 1668 | 2-thienylethyl | H | Me | 6-H | Me | OH |
| 1669 | 2-thienylethyl | H | Me | 7-H | H | Me |
| 1670 | 2-thienylethyl | H | Me | 7-H | H | NH2 |
| 1671 | 2-thienylethyl | H | Me | 7-H | H | OH |

TABLE 42-continued

| Compound No. | R1 | R2 | R3 | R3' | R4 | R5 |
|---|---|---|---|---|---|---|
| 1672 | 2-thienylethyl | H | Me | 7-H | Me | Me |
| 1673 | 2-thienylethyl | H | Me | 7-H | Me | NH2 |
| 1674 | 2-thienylethyl | H | Me | 7-H | Me | OH |
| 1675 | 2-thienylethyl | H | Me | 5-Cl | H | Me |
| 1676 | 2-thienylethyl | H | Me | 5-Cl | H | NH2 |
| 1677 | 2-thienylethyl | H | Me | 5-Cl | H | OH |
| 1678 | 2-thienylethyl | H | Me | 5-Cl | Me | Me |
| 1679 | 2-thienylethyl | H | Me | 5-Cl | Me | NH2 |
| 1680 | 2-thienylethyl | H | Me | 5-Cl | Me | OH |

TABLE 43

| Compound No. | R1 | R2 | R3 | R3' | R4 | R5 |
|---|---|---|---|---|---|---|
| 1681 | 2-thienylethyl | H | Me | 6-Cl | H | Me |
| 1682 | 2-thienylethyl | H | Me | 6-Cl | H | NH2 |
| 1683 | 2-thienylethyl | H | Me | 6-Cl | H | OH |
| 1684 | 2-thienylethyl | H | Me | 6-Cl | Me | Me |
| 1685 | 2-thienylethyl | H | Me | 6-Cl | Me | NH2 |
| 1686 | 2-thienylethyl | H | Me | 6-Cl | Me | OH |
| 1687 | 2-thienylethyl | H | Me | 7-Cl | H | Me |
| 1688 | 2-thienylethyl | H | Me | 7-Cl | H | NH2 |
| 1689 | 2-thienylethyl | H | Me | 7-Cl | H | OH |
| 1690 | 2-thienylethyl | H | Me | 7-Cl | Me | Me |
| 1691 | 2-thienylethyl | H | Me | 7-Cl | Me | NH2 |
| 1692 | 2-thienylethyl | H | Me | 7-Cl | Me | OH |
| 1693 | 2-thienylethyl | H | Me | 5-NH2 | H | Me |
| 1694 | 2-thienylethyl | H | Me | 5-NH2 | H | NH2 |
| 1695 | 2-thienylethyl | H | Me | 5-NH2 | H | OH |
| 1696 | 2-thienylethyl | H | Me | 5-NH2 | Me | Me |
| 1697 | 2-thienylethyl | H | Me | 5-NH2 | Me | NH2 |
| 1698 | 2-thienylethyl | H | Me | 5-NH2 | Me | OH |
| 1699 | 2-thienylethyl | H | Me | 6-NH2 | H | Me |
| 1700 | 2-thienylethyl | H | Me | 6-NH2 | H | NH2 |
| 1701 | 2-thienylethyl | H | Me | 6-NH2 | H | OH |
| 1702 | 2-thienylethyl | H | Me | 6-NH2 | Me | Me |
| 1703 | 2-thienylethyl | H | Me | 6-NH2 | Me | NH2 |
| 1704 | 2-thienylethyl | H | Me | 6-NH2 | Me | OH |
| 1705 | 2-thienylethyl | H | Me | 7-NH2 | H | Me |
| 1706 | 2-thienylethyl | H | Me | 7-NH2 | H | NH2 |
| 1707 | 2-thienylethyl | H | Me | 7-NH2 | H | OH |
| 1708 | 2-thienylethyl | H | Me | 7-NH2 | Me | Me |
| 1709 | 2-thienylethyl | H | Me | 7-NH2 | Me | NH2 |
| 1710 | 2-thienylethyl | H | Me | 7-NH2 | Me | OH |
| 1711 | 2-thienylethyl | H | Me | 5-Me | H | Me |
| 1712 | 2-thienylethyl | H | Me | 5-Me | H | NH2 |
| 1713 | 2-thienylethyl | H | Me | 5-Me | H | OH |
| 1714 | 2-thienylethyl | H | Me | 5-Me | Me | Me |
| 1715 | 2-thienylethyl | H | Me | 5-Me | Me | NH2 |
| 1716 | 2-thienylethyl | H | Me | 5-Me | Me | OH |
| 1717 | 2-thienylethyl | H | Me | 6-Me | H | Me |
| 1718 | 2-thienylethyl | H | Me | 6-Me | H | NH2 |
| 1719 | 2-thienylethyl | H | Me | 6-Me | H | OH |
| 1720 | 2-thienylethyl | H | Me | 6-Me | Me | Me |

TABLE 44

| Compound No. | R1 | R2 | R3 | R3' | R4 | R5 |
|---|---|---|---|---|---|---|
| 1721 | 2-thienylethyl | H | Me | 6-Me | Me | NH2 |
| 1722 | 2-thienylethyl | H | Me | 6-Me | Me | OH |
| 1723 | 2-thienylethyl | H | Me | 7-Me | H | Me |
| 1724 | 2-thienylethyl | H | Me | 7-Me | H | NH2 |
| 1725 | 2-thienylethyl | H | Me | 7-Me | H | OH |
| 1726 | 2-thienylethyl | H | Me | 7-Me | Me | Me |
| 1727 | 2-thienylethyl | H | Me | 7-Me | Me | NH2 |
| 1728 | 2-thienylethyl | H | Me | 7-Me | Me | OH |
| 1729 | 2-thienylethyl | H | H | 5-Cl | H | Me |
| 1730 | 2-thienylethyl | H | H | 5-Cl | H | NH2 |
| 1731 | 2-thienylethyl | H | H | 5-Cl | H | OH |
| 1732 | 2-thienylethyl | H | H | 5-Cl | Me | Me |
| 1733 | 2-thienylethyl | H | H | 5-Cl | Me | NH2 |

TABLE 44-continued

| Compound No. | R1 | R2 | R3 | R3' | R4 | R5 |
|---|---|---|---|---|---|---|
| 1734 | 2-thienylethyl | H | H | 5-Cl | Me | OH |
| 1735 | 2-thienylethyl | H | H | 6-Cl | H | Me |
| 1736 | 2-thienylethyl | H | H | 6-Cl | H | NH2 |
| 1737 | 2-thienylethyl | H | H | 6-Cl | H | OH |
| 1738 | 2-thienylethyl | H | H | 6-Cl | Me | Me |
| 1739 | 2-thienylethyl | H | H | 6-Cl | Me | NH2 |
| 1740 | 2-thienylethyl | H | H | 6-Cl | Me | OH |
| 1741 | 2-thienylethyl | H | H | 7-Cl | H | Me |
| 1742 | 2-thienylethyl | H | H | 7-Cl | H | NH2 |
| 1743 | 2-thienylethyl | H | H | 7-Cl | H | OH |
| 1744 | 2-thienylethyl | H | H | 7-Cl | Me | Me |
| 1745 | 2-thienylethyl | H | H | 7-Cl | Me | NH2 |
| 1746 | 2-thienylethyl | H | H | 7-Cl | Me | OH |
| 1747 | 2-thienylethyl | H | H | 5-NH2 | H | Me |
| 1748 | 2-thienylethyl | H | H | 5-NH2 | H | NH2 |
| 1749 | 2-thienylethyl | H | H | 5-NH2 | H | OH |
| 1750 | 2-thienylethyl | H | H | 5-NH2 | Me | Me |
| 1751 | 2-thienylethyl | H | H | 5-NH2 | Me | NH2 |
| 1752 | 2-thienylethyl | H | H | 5-NH2 | Me | OH |
| 1753 | 2-thienylethyl | H | H | 6-NH2 | H | Me |
| 1754 | 2-thienylethyl | H | H | 6-NH2 | H | NH2 |
| 1755 | 2-thienylethyl | H | H | 6-NH2 | H | OH |
| 1756 | 2-thienylethyl | H | H | 6-NH2 | Me | Me |
| 1757 | 2-thienylethyl | H | H | 6-NH2 | Me | NH2 |
| 1758 | 2-thienylethyl | H | H | 6-NH2 | Me | OH |
| 1759 | 2-thienylethyl | H | H | 7-NH2 | H | Me |
| 1760 | 2-thienylethyl | H | H | 7-NH2 | H | NH2 |

TABLE 45

| Compound No. | R1 | R2 | R3 | R3' | R4 | R5 |
|---|---|---|---|---|---|---|
| 1761 | 2-thienylethyl | H | H | 7-NH2 | H | OH |
| 1762 | 2-thienylethyl | H | H | 7-NH2 | Me | Me |
| 1763 | 2-thienylethyl | H | H | 7-NH2 | Me | NH2 |
| 1764 | 2-thienylethyl | H | H | 7-NH2 | Me | OH |
| 1765 | 2-thienylethyl | H | H | 5-Me | H | Me |
| 1766 | 2-thienylethyl | H | H | 5-Me | H | NH2 |
| 1767 | 2-thienylethyl | H | H | 5-Me | H | OH |
| 1768 | 2-thienylethyl | H | H | 5-Me | Me | Me |
| 1769 | 2-thienylethyl | H | H | 5-Me | Me | NH2 |
| 1770 | 2-thienylethyl | H | H | 5-Me | Me | OH |
| 1771 | 2-thienylethyl | H | H | 6-Me | H | Me |
| 1772 | 2-thienylethyl | H | H | 6-Me | H | NH2 |
| 1773 | 2-thienylethyl | H | H | 6-Me | H | OH |
| 1774 | 2-thienylethyl | H | H | 6-Me | Me | Me |
| 1775 | 2-thienylethyl | H | H | 6-Me | Me | NH2 |
| 1776 | 2-thienylethyl | H | H | 6-Me | Me | OH |
| 1777 | 2-thienylethyl | H | H | 7-Me | H | Me |
| 1778 | 2-thienylethyl | H | H | 7-Me | H | NH2 |
| 1779 | 2-thienylethyl | H | H | 7-Me | H | OH |
| 1780 | 2-thienylethyl | H | H | 7-Me | Me | Me |
| 1781 | 2-thienylethyl | H | H | 7-Me | Me | NH2 |
| 1782 | 2-thienylethyl | H | H | 7-Me | Me | OH |
| 1783 | 2-thienylethyl | OMe | Cl | 5-H | H | Me |
| 1784 | 2-thienylethyl | OMe | Cl | 5-H | H | NH2 |
| 1785 | 2-thienylethyl | OMe | Cl | 5-H | H | OH |
| 1786 | 2-thienylethyl | OMe | Cl | 5-H | Me | Me |
| 1787 | 2-thienylethyl | OMe | Cl | 5-H | Me | NH2 |
| 1788 | 2-thienylethyl | OMe | Cl | 5-H | Me | OH |
| 1789 | 2-thienylethyl | OMe | Cl | 6-H | H | Me |
| 1790 | 2-thienylethyl | OMe | Cl | 6-H | H | NH2 |
| 1791 | 2-thienylethyl | OMe | Cl | 6-H | H | OH |
| 1792 | 2-thienylethyl | OMe | Cl | 6-H | Me | Me |
| 1793 | 2-thienylethyl | OMe | Cl | 6-H | Me | NH2 |
| 1794 | 2-thienylethyl | OMe | Cl | 6-H | Me | OH |
| 1795 | 2-thienylethyl | OMe | Cl | 7-H | H | Me |
| 1796 | 2-thienylethyl | OMe | Cl | 7-H | H | NH2 |
| 1797 | 2-thienylethyl | OMe | Cl | 7-H | H | OH |
| 1798 | 2-thienylethyl | OMe | Cl | 7-H | Me | Me |
| 1799 | 2-thienylethyl | OMe | Cl | 7-H | Me | NH2 |
| 1800 | 2-thienylethyl | OMe | Cl | 7-H | Me | OH |

TABLE 46

| Compound No. | R1 | R2 | R3 | R3' | R4 | R5 |
|---|---|---|---|---|---|---|
| 1801 | 2-thienylethyl | OMe | Cl | 5-Cl | H | Me |
| 1802 | 2-thienylethyl | OMe | Cl | 5-Cl | H | NH2 |
| 1803 | 2-thienylethyl | OMe | Cl | 5-Cl | H | OH |
| 1804 | 2-thienylethyl | OMe | Cl | 5-Cl | Me | Me |
| 1805 | 2-thienylethyl | OMe | Cl | 5-Cl | Me | NH2 |
| 1806 | 2-thienylethyl | OMe | Cl | 5-Cl | Me | OH |
| 1807 | 2-thienylethyl | OMe | Cl | 6-Cl | H | Me |
| 1808 | 2-thienylethyl | OMe | Cl | 6-Cl | H | NH2 |
| 1809 | 2-thienylethyl | OMe | Cl | 6-Cl | H | OH |
| 1810 | 2-thienylethyl | OMe | Cl | 6-Cl | Me | Me |
| 1811 | 2-thienylethyl | OMe | Cl | 6-Cl | Me | NH2 |
| 1812 | 2-thienylethyl | OMe | Cl | 6-Cl | Me | OH |
| 1813 | 2-thienylethyl | OMe | Cl | 7-Cl | H | Me |
| 1814 | 2-thienylethyl | OMe | Cl | 7-Cl | H | NH2 |
| 1815 | 2-thienylethyl | OMe | Cl | 7-Cl | H | OH |
| 1816 | 2-thienylethyl | OMe | Cl | 7-Cl | Me | Me |
| 1817 | 2-thienylethyl | OMe | Cl | 7-Cl | Me | NH2 |
| 1818 | 2-thienylethyl | OMe | Cl | 7-Cl | Me | OH |
| 1819 | 2-thienylethyl | OMe | Cl | 5-NH2 | H | Me |
| 1820 | 2-thienylethyl | OMe | Cl | 5-NH2 | H | NH2 |
| 1821 | 2-thienylethyl | OMe | Cl | 5-NH2 | H | OH |
| 1822 | 2-thienylethyl | OMe | Cl | 5-NH2 | Me | Me |
| 1823 | 2-thienylethyl | OMe | Cl | 5-NH2 | Me | NH2 |
| 1824 | 2-thienylethyl | OMe | Cl | 5-NH2 | Me | OH |
| 1825 | 2-thienylethyl | OMe | Cl | 6-NH2 | H | Me |
| 1826 | 2-thienylethyl | OMe | Cl | 6-NH2 | H | NH2 |
| 1827 | 2-thienylethyl | OMe | Cl | 6-NH2 | H | OH |
| 1828 | 2-thienylethyl | OMe | Cl | 6-NH2 | Me | Me |
| 1829 | 2-thienylethyl | OMe | Cl | 6-NH2 | Me | NH2 |
| 1830 | 2-thienylethyl | OMe | Cl | 6-NH2 | Me | OH |
| 1831 | 2-thienylethyl | OMe | Cl | 7-NH2 | H | Me |
| 1832 | 2-thienylethyl | OMe | Cl | 7-NH2 | H | NH2 |
| 1833 | 2-thienylethyl | OMe | Cl | 7-NH2 | H | OH |
| 1834 | 2-thienylethyl | OMe | Cl | 7-NH2 | Me | Me |
| 1835 | 2-thienylethyl | OMe | Cl | 7-NH2 | Me | NH2 |
| 1836 | 2-thienylethyl | OMe | Cl | 7-NH2 | Me | OH |
| 1837 | 2-thienylethyl | OMe | Cl | 5-Me | H | Me |
| 1838 | 2-thienylethyl | OMe | Cl | 5-Me | H | NH2 |
| 1839 | 2-thienylethyl | OMe | Cl | 5-Me | H | OH |
| 1840 | 2-thienylethyl | OMe | Cl | 5-Me | Me | Me |

TABLE 47

| Compound No. | R1 | R2 | R3 | R3' | R4 | R5 |
|---|---|---|---|---|---|---|
| 1841 | 2-thienylethyl | OMe | Cl | 5-Me | Me | NH2 |
| 1842 | 2-thienylethyl | OMe | Cl | 5-Me | Me | OH |
| 1843 | 2-thienylethyl | OMe | Cl | 6-Me | H | Me |
| 1844 | 2-thienylethyl | OMe | Cl | 6-Me | H | NH2 |
| 1845 | 2-thienylethyl | OMe | Cl | 6-Me | H | OH |
| 1846 | 2-thienylethyl | OMe | Cl | 6-Me | Me | Me |
| 1847 | 2-thienylethyl | OMe | Cl | 6-Me | Me | NH2 |
| 1848 | 2-thienylethyl | OMe | Cl | 6-Me | Me | OH |
| 1849 | 2-thienylethyl | OMe | Cl | 7-Me | H | Me |
| 1850 | 2-thienylethyl | OMe | Cl | 7-Me | H | NH2 |
| 1851 | 2-thienylethyl | OMe | Cl | 7-Me | H | OH |
| 1852 | 2-thienylethyl | OMe | Cl | 7-Me | Me | Me |
| 1853 | 2-thienylethyl | OMe | Cl | 7-Me | Me | NH2 |
| 1854 | 2-thienylethyl | OMe | Cl | 7-Me | Me | OH |
| 1855 | 2-thienylethyl | OMe | NH2 | 5-H | H | Me |
| 1856 | 2-thienylethyl | OMe | NH2 | 5-H | H | NH2 |
| 1857 | 2-thienylethyl | OMe | NH2 | 5-H | H | OH |
| 1858 | 2-thienylethyl | OMe | NH2 | 5-H | Me | Me |
| 1859 | 2-thienylethyl | OMe | NH2 | 5-H | Me | NH2 |
| 1860 | 2-thienylethyl | OMe | NH2 | 5-H | Me | OH |
| 1861 | 2-thienylethyl | OMe | NH2 | 6-H | H | Me |
| 1862 | 2-thienylethyl | OMe | NH2 | 6-H | H | NH2 |
| 1863 | 2-thienylethyl | OMe | NH2 | 6-H | H | OH |
| 1864 | 2-thienylethyl | OMe | NH2 | 6-H | Me | Me |
| 1865 | 2-thienylethyl | OMe | NH2 | 6-H | Me | NH2 |
| 1866 | 2-thienylethyl | OMe | NH2 | 6-H | Me | OH |
| 1867 | 2-thienylethyl | OMe | NH2 | 7-H | H | Me |
| 1868 | 2-thienylethyl | OMe | NH2 | 7-H | H | NH2 |
| 1869 | 2-thienylethyl | OMe | NH2 | 7-H | H | OH |

TABLE 47-continued

| Compound No. | R1 | R2 | R3 | R3' | R4 | R5 |
|---|---|---|---|---|---|---|
| 1870 | 2-thienylethyl | OMe | NH2 | 7-H | Me | Me |
| 1871 | 2-thienylethyl | OMe | NH2 | 7-H | Me | NH2 |
| 1872 | 2-thienylethyl | OMe | NH2 | 7-H | Me | OH |
| 1873 | 2-thienylethyl | OMe | NH2 | 5-Cl | H | Me |
| 1874 | 2-thienylethyl | OMe | NH2 | 5-Cl | H | NH2 |
| 1875 | 2-thienylethyl | OMe | NH2 | 5-Cl | H | OH |
| 1876 | 2-thienylethyl | OMe | NH2 | 5-Cl | Me | Me |
| 1877 | 2-thienylethyl | OMe | NH2 | 5-Cl | Me | NH2 |
| 1878 | 2-thienylethyl | OMe | NH2 | 5-Cl | Me | OH |
| 1879 | 2-thienylethyl | OMe | NH2 | 6-Cl | H | Me |
| 1880 | 2-thienylethyl | OMe | NH2 | 6-Cl | H | NH2 |

TABLE 48

| Compound No. | R1 | R2 | R3 | R3' | R4 | R5 |
|---|---|---|---|---|---|---|
| 1881 | 2-thienylethyl | OMe | NH2 | 6-Cl | H | OH |
| 1882 | 2-thienylethyl | OMe | NH2 | 6-Cl | Me | Me |
| 1883 | 2-thienylethyl | OMe | NH2 | 6-Cl | Me | NH2 |
| 1884 | 2-thienylethyl | OMe | NH2 | 6-Cl | Me | OH |
| 1885 | 2-thienylethyl | OMe | NH2 | 7-Cl | H | Me |
| 1886 | 2-thienylethyl | OMe | NH2 | 7-Cl | H | NH2 |
| 1887 | 2-thienylethyl | OMe | NH2 | 7-Cl | H | OH |
| 1888 | 2-thienylethyl | OMe | NH2 | 7-Cl | Me | Me |
| 1889 | 2-thienylethyl | OMe | NH2 | 7-Cl | Me | NH2 |
| 1890 | 2-thienylethyl | OMe | NH2 | 7-Cl | Me | OH |
| 1891 | 2-thienylethyl | OMe | NH2 | 5-NH2 | H | Me |
| 1892 | 2-thienylethyl | OMe | NH2 | 5-NH2 | H | NH2 |
| 1893 | 2-thienylethyl | OMe | NH2 | 5-NH2 | H | OH |
| 1894 | 2-thienylethyl | OMe | NH2 | 5-NH2 | Me | Me |
| 1895 | 2-thienylethyl | OMe | NH2 | 5-NH2 | Me | NH2 |
| 1896 | 2-thienylethyl | OMe | NH2 | 5-NH2 | Me | OH |
| 1897 | 2-thienylethyl | OMe | NH2 | 6-NH2 | H | Me |
| 1898 | 2-thienylethyl | OMe | NH2 | 6-NH2 | H | NH2 |
| 1899 | 2-thienylethyl | OMe | NH2 | 6-NH2 | H | OH |
| 1900 | 2-thienylethyl | OMe | NH2 | 6-NH2 | Me | Me |
| 1901 | 2-thienylethyl | OMe | NH2 | 6-NH2 | Me | NH2 |
| 1902 | 2-thienylethyl | OMe | NH2 | 6-NH2 | Me | OH |
| 1903 | 2-thienylethyl | OMe | NH2 | 7-NH2 | H | Me |
| 1904 | 2-thienylethyl | OMe | NH2 | 7-NH2 | H | NH2 |
| 1905 | 2-thienylethyl | OMe | NH2 | 7-NH2 | H | OH |
| 1906 | 2-thienylethyl | OMe | NH2 | 7-NH2 | Me | Me |
| 1907 | 2-thienylethyl | OMe | NH2 | 7-NH2 | Me | NH2 |
| 1908 | 2-thienylethyl | OMe | NH2 | 7-NH2 | Me | OH |
| 1909 | 2-thienylethyl | OMe | NH2 | 5-Me | H | Me |
| 1910 | 2-thienylethyl | OMe | NH2 | 5-Me | H | NH2 |
| 1911 | 2-thienylethyl | OMe | NH2 | 5-Me | H | OH |
| 1912 | 2-thienylethyl | OMe | NH2 | 5-Me | Me | Me |
| 1913 | 2-thienylethyl | OMe | NH2 | 5-Me | Me | NH2 |
| 1914 | 2-thienylethyl | OMe | NH2 | 5-Me | Me | OH |
| 1915 | 2-thienylethyl | OMe | NH2 | 6-Me | H | Me |
| 1916 | 2-thienylethyl | OMe | NH2 | 6-Me | H | NH2 |
| 1917 | 2-thienylethyl | OMe | NH2 | 6-Me | H | OH |
| 1918 | 2-thienylethyl | OMe | NH2 | 6-Me | Me | Me |
| 1919 | 2-thienylethyl | OMe | NH2 | 6-Me | Me | NH2 |
| 1920 | 2-thienylethyl | OMe | NH2 | 6-Me | Me | OH |

TABLE 49

| Compound No. | R1 | R2 | R3 | R3' | R4 | R5 |
|---|---|---|---|---|---|---|
| 1921 | 2-thienylethyl | OMe | NH2 | 7-Me | H | Me |
| 1922 | 2-thienylethyl | OMe | NH2 | 7-Me | H | NH2 |
| 1923 | 2-thienylethyl | OMe | NH2 | 7-Me | H | OH |
| 1924 | 2-thienylethyl | OMe | NH2 | 7-Me | Me | Me |
| 1925 | 2-thienylethyl | OMe | NH2 | 7-Me | Me | NH2 |
| 1926 | 2-thienylethyl | OMe | NH2 | 7-Me | Me | OH |
| 1927 | 2-thienylethyl | OMe | Me | 5-H | H | Me |
| 1928 | 2-thienylethyl | OMe | Me | 5-H | H | NH2 |
| 1929 | 2-thienylethyl | OMe | Me | 5-H | H | OH |
| 1930 | 2-thienylethyl | OMe | Me | 5-H | Me | Me |
| 1931 | 2-thienylethyl | OMe | Me | 5-H | Me | NH2 |

TABLE 49-continued

| Compound No. | R1 | R2 | R3 | R3' | R4 | R5 |
|---|---|---|---|---|---|---|
| 1932 | 2-thienylethyl | OMe | Me | 5-H | Me | OH |
| 1933 | 2-thienylethyl | OMe | Me | 6-H | H | Me |
| 1934 | 2-thienylethyl | OMe | Me | 6-H | H | NH2 |
| 1935 | 2-thienylethyl | OMe | Me | 6-H | H | OH |
| 1936 | 2-thienylethyl | OMe | Me | 6-H | Me | Me |
| 1937 | 2-thienylethyl | OMe | Me | 6-H | Me | NH2 |
| 1938 | 2-thienylethyl | OMe | Me | 6-H | Me | OH |
| 1939 | 2-thienylethyl | OMe | Me | 7-H | H | Me |
| 1940 | 2-thienylethyl | OMe | Me | 7-H | H | NH2 |
| 1941 | 2-thienylethyl | OMe | Me | 7-H | H | OH |
| 1942 | 2-thienylethyl | OMe | Me | 7-H | Me | Me |
| 1943 | 2-thienylethyl | OMe | Me | 7-H | Me | NH2 |
| 1944 | 2-thienylethyl | OMe | Me | 7-H | Me | OH |
| 1945 | 2-thienylethyl | OMe | Me | 5-Cl | H | Me |
| 1946 | 2-thienylethyl | OMe | Me | 5-Cl | H | NH2 |
| 1947 | 2-thienylethyl | OMe | Me | 5-Cl | H | OH |
| 1948 | 2-thienylethyl | OMe | Me | 5-Cl | Me | Me |
| 1949 | 2-thienylethyl | OMe | Me | 5-Cl | Me | NH2 |
| 1950 | 2-thienylethyl | OMe | Me | 5-Cl | Me | OH |
| 1951 | 2-thienylethyl | OMe | Me | 6-Cl | H | Me |
| 1952 | 2-thienylethyl | OMe | Me | 6-Cl | H | NH2 |
| 1953 | 2-thienylethyl | OMe | Me | 6-Cl | H | OH |
| 1954 | 2-thienylethyl | OMe | Me | 6-Cl | Me | Me |
| 1955 | 2-thienylethyl | OMe | Me | 6-Cl | Me | NH2 |
| 1956 | 2-thienylethyl | OMe | Me | 6-Cl | Me | OH |
| 1957 | 2-thienylethyl | OMe | Me | 7-Cl | H | Me |
| 1958 | 2-thienylethyl | OMe | Me | 7-Cl | H | NH2 |
| 1959 | 2-thienylethyl | OMe | Me | 7-Cl | H | OH |
| 1960 | 2-thienylethyl | OMe | Me | 7-Cl | Me | Me |

TABLE 50

| Compound No. | R1 | R2 | R3 | R3' | R4 | R5 |
|---|---|---|---|---|---|---|
| 1961 | 2-thienylethyl | OMe | Me | 7-Cl | Me | NH2 |
| 1962 | 2-thienylethyl | OMe | Me | 7-Cl | Me | OH |
| 1963 | 2-thienylethyl | OMe | Me | 5-NH2 | H | Me |
| 1964 | 2-thienylethyl | OMe | Me | 5-NH2 | H | NH2 |
| 1965 | 2-thienylethyl | OMe | Me | 5-NH2 | H | OH |
| 1966 | 2-thienylethyl | OMe | Me | 5-NH2 | Me | Me |
| 1967 | 2-thienylethyl | OMe | Me | 5-NH2 | Me | NH2 |
| 1968 | 2-thienylethyl | OMe | Me | 5-NH2 | Me | OH |
| 1969 | 2-thienylethyl | OMe | Me | 6-NH2 | H | Me |
| 1970 | 2-thienylethyl | OMe | Me | 6-NH2 | H | NH2 |
| 1971 | 2-thienylethyl | OMe | Me | 6-NH2 | H | OH |
| 1972 | 2-thienylethyl | OMe | Me | 6-NH2 | Me | Me |
| 1973 | 2-thienylethyl | OMe | Me | 6-NH2 | Me | NH2 |
| 1974 | 2-thienylethyl | OMe | Me | 6-NH2 | Me | OH |
| 1975 | 2-thienylethyl | OMe | Me | 7-NH2 | H | Me |
| 1976 | 2-thienylethyl | OMe | Me | 7-NH2 | H | NH2 |
| 1977 | 2-thienylethyl | OMe | Me | 7-NH2 | H | OH |
| 1978 | 2-thienylethyl | OMe | Me | 7-NH2 | Me | Me |
| 1979 | 2-thienylethyl | OMe | Me | 7-NH2 | Me | NH2 |
| 1980 | 2-thienylethyl | OMe | Me | 7-NH2 | Me | OH |
| 1981 | 2-thienylethyl | OMe | Me | 5-Me | H | Me |
| 1982 | 2-thienylethyl | OMe | Me | 5-Me | H | NH2 |
| 1983 | 2-thienylethyl | OMe | Me | 5-Me | H | OH |
| 1984 | 2-thienylethyl | OMe | Me | 5-Me | Me | Me |
| 1985 | 2-thienylethyl | OMe | Me | 5-Me | Me | NH2 |
| 1986 | 2-thienylethyl | OMe | Me | 5-Me | Me | OH |
| 1987 | 2-thienylethyl | OMe | Me | 6-Me | H | Me |
| 1988 | 2-thienylethyl | OMe | Me | 6-Me | H | NH2 |
| 1989 | 2-thienylethyl | OMe | Me | 6-Me | H | OH |
| 1990 | 2-thienylethyl | OMe | Me | 6-Me | Me | Me |
| 1991 | 2-thienylethyl | OMe | Me | 6-Me | Me | NH2 |
| 1992 | 2-thienylethyl | OMe | Me | 6-Me | Me | OH |
| 1993 | 2-thienylethyl | OMe | Me | 7-Me | H | Me |
| 1994 | 2-thienylethyl | OMe | Me | 7-Me | H | NH2 |
| 1995 | 2-thienylethyl | OMe | Me | 7-Me | H | OH |
| 1996 | 2-thienylethyl | OMe | Me | 7-Me | Me | Me |
| 1997 | 2-thienylethyl | OMe | Me | 7-Me | Me | NH2 |
| 1998 | 2-thienylethyl | OMe | Me | 7-Me | Me | OH |

TABLE 50-continued

| Compound No. | R1 | R2 | R3 | R3' | R4 | R5 |
|---|---|---|---|---|---|---|
| 1999 | 2-thienylethyl | OMe | H | 5-Cl | H | Me |
| 2000 | 2-thienylethyl | OMe | H | 5-Cl | H | NH2 |

TABLE 51

| Compound No. | R1 | R2 | R3 | R3' | R4 | R5 |
|---|---|---|---|---|---|---|
| 2001 | 2-thienylethyl | OMe | H | 5-Cl | H | OH |
| 2002 | 2-thienylethyl | OMe | H | 5-Cl | Me | Me |
| 2003 | 2-thienylethyl | OMe | H | 5-Cl | Me | NH2 |
| 2004 | 2-thienylethyl | OMe | H | 5-Cl | Me | OH |
| 2005 | 2-thienylethyl | OMe | H | 6-Cl | H | Me |
| 2006 | 2-thienylethyl | OMe | H | 6-Cl | H | NH2 |
| 2007 | 2-thienylethyl | OMe | H | 6-Cl | H | OH |
| 2008 | 2-thienylethyl | OMe | H | 6-Cl | Me | Me |
| 2009 | 2-thienylethyl | OMe | H | 6-Cl | Me | NH2 |
| 2010 | 2-thienylethyl | OMe | H | 6-Cl | Me | OH |
| 2011 | 2-thienylethyl | OMe | H | 7-Cl | H | Me |
| 2012 | 2-thienylethyl | OMe | H | 7-Cl | H | NH2 |
| 2013 | 2-thienylethyl | OMe | H | 7-Cl | H | OH |
| 2014 | 2-thienylethyl | OMe | H | 7-Cl | Me | Me |
| 2015 | 2-thienylethyl | OMe | H | 7-Cl | Me | NH2 |
| 2016 | 2-thienylethyl | OMe | H | 7-Cl | Me | OH |
| 2017 | 2-thienylethyl | OMe | H | 5-NH2 | H | Me |
| 2018 | 2-thienylethyl | OMe | H | 5-NH2 | H | NH2 |
| 2019 | 2-thienylethyl | OMe | H | 5-NH2 | H | OH |
| 2020 | 2-thienylethyl | OMe | H | 5-NH2 | Me | Me |
| 2021 | 2-thienylethyl | OMe | H | 5-NH2 | Me | NH2 |
| 2022 | 2-thienylethyl | OMe | H | 5-NH2 | Me | OH |
| 2023 | 2-thienylethyl | OMe | H | 6-NH2 | H | Me |
| 2024 | 2-thienylethyl | OMe | H | 6-NH2 | H | NH2 |
| 2025 | 2-thienylethyl | OMe | H | 6-NH2 | H | OH |
| 2026 | 2-thienylethyl | OMe | H | 6-NH2 | Me | Me |
| 2027 | 2-thienylethyl | OMe | H | 6-NH2 | Me | NH2 |
| 2028 | 2-thienylethyl | OMe | H | 6-NH2 | Me | OH |
| 2029 | 2-thienylethyl | OMe | H | 7-NH2 | H | Me |
| 2030 | 2-thienylethyl | OMe | H | 7-NH2 | H | NH2 |
| 2031 | 2-thienylethyl | OMe | H | 7-NH2 | H | OH |
| 2032 | 2-thienylethyl | OMe | H | 7-NH2 | Me | Me |
| 2033 | 2-thienylethyl | OMe | H | 7-NH2 | Me | NH2 |
| 2034 | 2-thienylethyl | OMe | H | 7-NH2 | Me | OH |
| 2035 | 2-thienylethyl | OMe | H | 5-Me | H | Me |
| 2036 | 2-thienylethyl | OMe | H | 5-Me | H | NH2 |
| 2037 | 2-thienylethyl | OMe | H | 5-Me | H | OH |
| 2038 | 2-thienylethyl | OMe | H | 5-Me | Me | Me |
| 2039 | 2-thienylethyl | OMe | H | 5-Me | Me | NH2 |
| 2040 | 2-thienylethyl | OMe | H | 5-Me | Me | OH |

TABLE 52

| Compound No. | R1 | R2 | R3 | R3' | R4 | R5 |
|---|---|---|---|---|---|---|
| 2041 | 2-thienylethyl | OMe | H | 6-Me | H | Me |
| 2042 | 2-thienylethyl | OMe | H | 6-Me | H | NH2 |
| 2043 | 2-thienylethyl | OMe | H | 6-Me | H | OH |
| 2044 | 2-thienylethyl | OMe | H | 6-Me | Me | Me |
| 2045 | 2-thienylethyl | OMe | H | 6-Me | Me | NH2 |
| 2046 | 2-thienylethyl | OMe | H | 6-Me | Me | OH |
| 2047 | 2-thienylethyl | OMe | H | 7-Me | H | Me |
| 2048 | 2-thienylethyl | OMe | H | 7-Me | H | NH2 |
| 2049 | 2-thienylethyl | OMe | H | 7-Me | H | OH |
| 2050 | 2-thienylethyl | OMe | H | 7-Me | Me | Me |
| 2051 | 2-thienylethyl | OMe | H | 7-Me | Me | NH2 |
| 2052 | 2-thienylethyl | OMe | H | 7-Me | Me | OH |

The compounds of Formula (I) can be obtained by, for example, condensing a ketone (III) as a starting material with o-aminobenzaldehyde derivative (IVa), o-aminoacetophenone (IVb) or o-aminobenzonitrile (IVc) in a solvent in the presence of an acid catalyst, in accordance with the method described in Japanese Laid-open Patent Application (Kokai) No. 4-275288 or WO99/02157. In this case, by using an optically active compound as the starting material, an optically active compound can be obtained (Scheme 1).

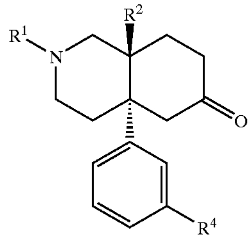

(III)

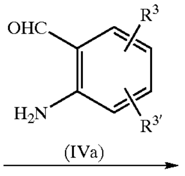

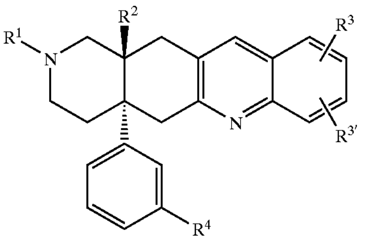

(Ia)

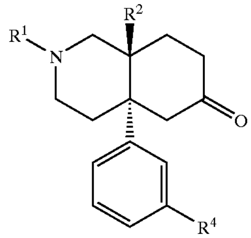

(III)

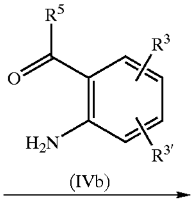

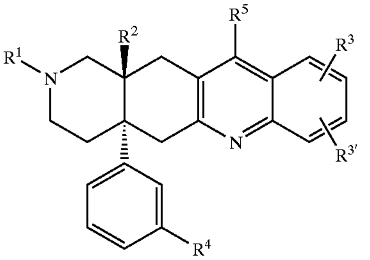

(Ib)

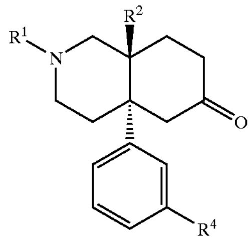

(III)

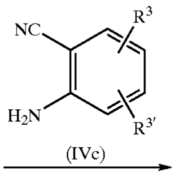

-continued

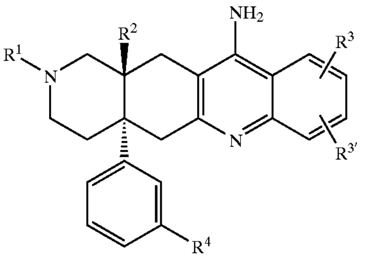

(Ic)

The fact that the isoquinoline derivatives of Formula (I) are effective for therapy and/or prevention of memory disorder may be confirmed by a behavioral pharmacological method using animals as described in Examples. More specifically, the passive avoidance test, the conditioned active avoidance test, or the spacial memory test using a water maize or a radial type maze are often used to develop an anti-dementia drug.

The compounds of the present invention may be used as pharmaceuticals useful for therapy and/or prevention of dementia accompanying learning disability and/or memory disorder. Especially, they may be used for therapy and/or prevention of dementia accompanying memory disorder caused by a cerebrovascular disease, neurodegererantive disease, endocrine disease, nutritional or metabolic disorder, anoxic encephalopathy, tumor, infectious disease, disorder of metabolism of a metal, or drug addiction. Examples of cerebrovascular diseases exhibiting dementia include cerebral infarction, cerebral hemorrhage, multiinfarct dementia, moyamoya disease, intracranial arteriovenous malformation, systemic lupus erythematodes (SLE) and angitis such as temporal arteritis. Examples of neurodegeretative diseases accompanying dementia include Alzheimer's disease, Pick's disease, Parkinson's disease, Huntington's disease, progressive supranuclear palsy, Shy-Drager syndrome, Ramsay Hunt's syndrome and familial basal ganglia calcification. Examples of endocrine diseases include hypothyroidism, hypoparathyroidism syndrome, Cushing's disease, Addison's disease and recurrent hypoglycemic attack. Examples of nutritional or metabolic disorder include Wernicke encephalitis, pellagra encephalopathy, vitamin B12 deficiency, chronic metabolic disorders such as hepatic insufficiency and renal insufficiency, and hyponatremia. Examples of anoxic encephalopathy include carbon monoxide poisoning. Examples of tumors include cerebral tumor and meningitis carcinomatosa. Examples of infectious diseases include cerebral meningitis, encephalitides, cerebral tumor, slow virus disease, AIDS and neurosyphilis. Examples of other diseases which exhibit dementia include normal pressure hydrocephalus, chronic subdural hematoma, brain contusion, myotonic dystrophy and mitochondrial myopathy. The application of the compounds of the present invention is not restricted to these diseases.

The agent for improving learning and/or memory according to the present invention may be used in combination with one or more of other drugs for therapy and/or prevention of diseases exhibiting dementia (e.g., cerebrovascular diseases, neurodegeretative diseases, endocrine diseases, nutritional or metabolic disorder, anoxic encephalopathy, malignant tumors and infectious diseases) and drugs used for problamatic behavior accompanied by dementia (night delirium, night restlessness, depression, sleep disorder and personality change).

Examples of the drugs for prevention and/or therapy of cerebrovascular diseases include cerebral circulation metabolism activators such as ATP, cytochrome c, meclofenoxate hydrochloride, idebenone, propentofylline, γ-aminobutyric acid, γ-amino-β-hydroxybutyric acid, calcium hopantenate, anirasetam, amantadine hydrochloride, lisuride maleate, bifemelane hydrochloride, indeloxazine hydrochloride, dihydroergotoxine mesylate, ifenprodil tartrate, moxisylyte hydrochloride, bencylane fumarate, brovincamine fumarate, ibudilast, vinpocetine, nicergoline, cinepazide maleate, pentoxifylline, trapidil, dilazep hydrochloride, flunarizine hydrochloride, cinnarizine, nicardipine hydrochloride, nilvadipine and kallidinogenase; antihypertensive drugs such as chlorothiazide, ethacrynic acid, clonidine, reserpine, propranolol, prazosin, hydralazine, papaverine, captopril and nifedipine; anticoagulant drugs such as warfarin; thrombolytic agents such as urokinase; anti-platelet agents such as ozagrel and beraprost.

Examples of drugs for prevention and/or therapy of neurodegenerative diseases include anti-dementia drugs such as tacrine, therapeutic agents for Parkinson's disease such as levodopa, benztropine, deprenyl, biperiden, promethazine and diphenhydramine, as well as the above-mentioned cerebral circulation metabolism activators.

Examples of the drugs for prevention and/or therapy of problematic behavior accompanied by dementia include antidepressant drugs such as amitriptyline, dothiepin, lofepramine, imipramine, fluoxetine, fluvoxamine, mianserin, trazodone, maprotiline and safrazine; antianxiety agents such as diazepam and meprobamate; hypnotics such as haloxazolam and triazolam; and neuroplegics such as chlorpromazine, thioridazine and fluphenazine.

Examples of the drugs for prevention and/or therapy of endocrine diseases include antithyroid drugs (e.g., thionamide, methimazole and iodine), antidiabetic drugs (e.g., insulin formulation, tolbutamide, glipizide, metformin and acarbose), adenocorticotropic hormones (e.g., glucocorticoids such as hydrocortisone, prednisolone, betamethasone, dexamethasone; and mineral corticoids such as aldosterone), and anti-adenocorticotropic hormones (e.g., metyrapone).

Examples of the drugs for prevention and/or therapy of malignant tumors include alkylating agents such as cyclophosphamide and chlorambucil; cytotoxic antibiotics such as doxorubicin; vinca alkaloids such as vincristin; antimetabolites such as methotrexate, fluorouracil, cytarabine and mercaptopurine; and cisplatin.

When the agent for improving learning and/or memory according to the present invention is clinically used, the agent may be in the form of free base or salt thereof per se, or may be admixed with one or more additives such as vehicles, stabilizers, preservatives, buffer agents, solubilizers, emulsifiers, diluents and isotonic agents. The agent may be administered either orally or parenterally. The agent may be formulated in the form of injection solution, tablets, solution, capsules, granules, powder or the like. These formulations may be produced by known formulation techniques. The dose may be appropriately selected depending on the symptoms, age and bodyweight of the patient, and administration route. The dose of the effective component for an adult may be 0.0001 mg to 10 g per day, preferably 0.001 mg to 1 g per day, and the agent may be administered in one time or in several times.

EXAMPLES

The present invention will now be described concretely referring to Reference Examples and Examples.

Reference Example 1

(4aR, 12aR)-2-methyl-4a-(3-hydroxyphenyl)-1,2,3,4,4a,5,12,12a-octahydro-quinoline[2,3-g]isoquinoline 1 Methanesulfonic Acid Salt This compound was synthesized by the method described in WO99/02157.

Reference Example 2

2-methyl-4aα-(3-methoxyphenyl)-11-methyl-1,2,3,4,4a,5,12,12aβ-octahydro-quinolino[2,3-g]isoquinoline 2

To 5 mL of acetic acid, 150 mg (0.55 mmol) of 2-methyl-4α-(3-methoxyphenyl)-6-oxo-1,2,3,4,4a,5,6,7,8,8aβ-octahydroisoquinoline and 100 mg (0.74 mmol) of o-aminoacetophenone were added and the mixture was heated to reflux for 3 hours. After allowing the mixture to cool, saturated aqueous sodium hydrogen carbonate solution was added and the resulting mixture was extracted with ethyl acetate. The organic layer was washed with saturated brine and dried over anhydrous magnesium sulfate. The obtained residue was subjected to silica gel column chromatography (chlroform:methanol:28% aqueous ammonia=20:1:0.1 to 10:1:0.1) for purification to obtain 211 mg of the captioned compound (yield: 100%).

Reference Example 3

2-methyl-4aα-(3-hydroxyphenyl)-11-methyl-1,2,3,4,4a,5,12,12aβ-octahydro-quinolino[2,3-g]isoquinoline 3 Hydrochloric Acid Salt In 7 mL of DMF solvent, 210 mg (0.56 mmol) of 2-methyl-4aα-(3-methoxyphenyl)-11-methyl-1,2,3,4,4a,5,12,12aβ-octahydro-quinolino[2,3-g]isoquinoline obtained in Reference Example 2 and 0.29 mL (3.20 mmol) of n-propanethiol were dissolved under argon atmosphere. To the mixture, 320 mg (2.85 mmol) of potassium-t-butoxide was added and the mixture was heated at 120° C. for 20 hours under stirring. To the mixture, 4 mL of 1N hydrochloric acid was added while cooling the mixture in ice to make the mixture acidic, and then saturated aqueous sodium hydrogen carbonate solution was added to make the mixture again basic, followed by extraction of the resulting mixture with chloroform: methanol (4:1) mixture. The organic layer was washed with water and dried over anhydrous magnesium sulfate, followed by concentration of the resulting product. The obtained residue was recrystallized from dichloromethane-methanol mixture to obtain 131 mg of the captioned compound (yield: 65%). The obtained product was suspended in methanol and hydrochloric acid was added to convert the compound to a salt. After concentration of the product, ether was added and solids were collected by filtration to obtain 143 mg of hydrochloric acid salt of the captioned compound.

Reference Example 4

2-methyl-4aα-(3-methoxphenyl)-11-amino-1,2,3,4,4a,5,12,12aβ-octahydro-quinolino[2,3-g]isoquinoline 4

To 5 mL of acetic acid, 150 mg (0.55 mmol) of 2-methyl-4aα-(3-methoxyphenyl)-6-oxo-1,2,3,4,4a, 5,6,7,8,8aβ-octahydroisoquinoline and 130 mg (1.10 mmol) of o-aminobenzonitrile were added, and the mixture was heated to reflux for 44 hours. After allowing the mixture to cool, saturated aqueous sodium hydrogen carbonate solution was added, and the resulting mixture was extracted with chloroform:methanol (4:1) mixture. The organic layer was washed with brine and dried over anhydrous magnesium sulfate, followed by concentration of the obtained product. The obtained residue was subjected to amine-coated silica gel column chromatography (chloroform:methanol=50:1) for purification to obtain 83 mg of the captioned compound (yield: 41%).

Reference Example 5

2-methyl-4aα-(3-hydroxyphenyl)-11-amino-1,2,3,4,4a,5,12,12aβ-octahydro-quinolino[2,3-g]isoquinoline 5 Hydrochloric Acid Salt In 7 mL of DMF solvent, 83 mg (0.22 mmol) of 2-methyl-4aα-(3-methoxphenyl)-11-amino-1,2,3,4,4a,5,12,12aβ-octahydro-quinolino[2,3-g]isoquinoline obtained in Reference Example 4 and 0.10 mL (1.060 mmol) of n-propanethiol were dissolved under argon atmosphere. To the mixture, 106 mg (0.95 mmol) of potassium-t-butoxide was added and the mixture was heated at 120° C. for 20 hours under stirring. To the mixture, 4 mL of 1N hydrochloric acid was added while cooling the mixture in ice to make the mixture acidic, and then saturated aqueous sodium hydrogen carbonate solution was added to make the mixture again basic, followed by extraction of the resulting mixture with chloroform:methanol (4:1) mixture. The organic layer was washed with water and dried over anhydrous magnesium sulfate, followed by concentration of the resulting product. The obtained residue was recrystallized from dichloromethane-methanol mixture to obtain 35 mg of the captioned compound (yield: 44%). The obtained product was suspended in methanol and hydrochloric acid was added to convert the compound to a salt. After concentration of the product, ether was added and solids were collected by filtration to obtain 40 mg of hydrochloric acid salt of the captioned compound.

Reference Example 6

(+)-7,9-dibromo-4a-(3-methoxyphenyl)-2-methyl-1,2,3,4,4a,5,12,12a-octahydro-quinoline[2,3 g]isoquinoline 6

In ethanol, 382.4 mg of (+)-4a-(3-methoxyphenyl)-2-methyl-6-oxo-1,2,3,4,4a,5,6,7,8,8a-octahydroisoquinoline and 1.95 g of 2-amino-3,5-dibromobenzaldehyde were dissolved, and 0.454 ml of methanesulfonic acid was added, followed by heating the resulting mixture to reflux for 2 hours. After allowing the mixture to cool, saturated aqueous sodium hydrogen carbonate solution was added and the resulting mixture was extracted with ethyl acetate. The organic layer was washed with brine and dried over anhydrous magnesium sulfate. After filtration and concentration, the obtained residue was purified by silica gel column chromatography (chloroform:methanol=40:1) to obtain 683.7 mg of the captioned compound (yield: 95%).

Reference Example 7

(+)-7,9-dibromo-4a-(3-hydroxyphenyl)-2-methyl-1,2,3,4,4a,5,12,12a-octahydro-quinoline[2,3 g]isoquinoline 7

In 15 ml of dichloromethane, 669.6 mg of (+)-7,9-dibromo-4a-(3-methoxyphenyl)-2-methyl-1,2,3,4,4a,5,12,12a-octahydro-quinoline[2,3 g]isoquinoline obtained in Reference Example 6 was dissolved, and 6.49 ml of boron tribromide solution in dichloromethane (1 mol/l) was added dropwise while cooling the mixture in ice. After stirring the mixture at 0° C. for 4 hours, saturated aqueous sodium hydrogen carbonate solution was added and the resulting mixture was vigorously stirred for 30 minutes at room temperature. After extracting the mixture with chloroform, the organic layer was washed with brine and dried over anhydrous sodium sulfate. After filtration and concentration, the obtained residue was purified by silica gel column chromatography (chloroform:methanol=20:1–5:1) to obtain 381.5 mg of the captioned compound (yield: 59%).

Reference Example 8

(+)-7,9-dibromo-4a-(3-hydroxyphenyl)-2-methyl-1,2,3,4,4a,5,12,12a-octahydro-quinoline[2,3 g]isoquinoline Methanesulfonic Acid Salt 8

In methanol, 381.5 mg of (+)-7,9-dibromo-4a-(3-hydroxyphenyl)-2-methyl-1,2,3,4,4a,5,12,12a-octahydro-quinoline[2,3 g]isoquinoline obtained in Reference Example 7 was suspended, and 1.522 ml of methanesulfonic acid was added, followed by stirring the mixture for 10 minutes. The reaction solution was concentrated and the obtained residue was repreciptated from methanol, ethyl acetate and diethylether to obtain 348.2 mg of the captioned compound.

Reference Example 9

(+)-9-fluoro-4a-(3-methoxyphenyl)-2-methyl-1,2,3,4,4a,5,12,12a-octahydro-quinoline[2,3 g]isoquinoline 9

A mixture of 380.3 mg of (+)-4a-(3-methoxyphenyl)-2-methyl-6-oxo-1,2,3,4,4a,5,6,7,8,8a-octahydroisoquinoline and 0.924 ml of dimethylformamide dimethylacetal in toluene solvent was heated to reflux for 5.5 hours. After allowing the mixture to cool, the reaction solution was concentrated and dried under reduced pressure. The residue was dissolved in 8 ml of xylene, and 0.395 ml of 4-fluoroaniline and 0.536 ml of trifluoroacetic acid were added, followed by heating the resulting mixture to reflux for 11 hours. After allowing the mixture to cool, saturated aqueous sodium hydrogen carbonate solution was added and the mixture was extracted with ethyl acetate. The organic layer was washed with brine and dried over anhydrous sodium sulfate. After filtration and concentration, the obtained residue was purified by silica gel column chromatography (chlroform:methanol=15:1–10:1) to obtain 249.9 mg of the captioned compound (yield: 48%).

Reference Example 10

(+)-9-fluoro-4a-(3-hydroxyphenyl)-2-methyl-1,2,3,4,4a,5,12,12a-octahydro-quinoline[2,3 g]isoquinoline 10

In 9 ml of dichloromethane, 249.9 mg of (+)-9-fluoro-4a-(3-methoxyphenyl)-2-methyl-1,2,3,4,4a,5,12,12a-octahydro-quinoline[2,3 g]isoquinoline obtained in Reference Example 9 was dissolved, and 3.32 ml of 1N boron tribromide solution in dichloromethane was added dropwise while cooling the mixture in ice, and then the resulting mixture was stirred for 2 hours. Saturated aqueous sodium hydrogen carbonate solution was slowly added and the mixture was vigorously stirred for 30 minutes. The reaction solution was extracted with chloroform and the organic layer was washed with brine, followed by drying over anhydrous sodium sulfate. After filtration and concentration, the obtained residue was purified by silica gel column chromatography (chlroform:methanol:isopropylamine=97:2.7:0.3), and then by thin layer chromatography (chloroform:chloroform saturated with ammonia=1:1) to obtain 65 mg of the captioned compound (yield: 27%).

Reference Example 11

(+)-9-fluoro-4a-(3-hydroxyphenyl)-2-methyl-1,2,3,4,4a,5,12,12a-octahydro-quinoline[2,3 g]isoquinoline Tartaric Acid Salt 11

In 2 ml of methanol, 48.6 mg of (+)-9-fluoro-4a-(3-hydroxyphenyl)-2-methyl-1,2,3,4,4a,5,12,12a-octahydro-quinoline[2,3 g]isoquinoline obtained in Reference Example 10 was dissolved, and 40.2 mg of L-tartaric acid was added, followed by stirring the mixture for 10 minutes. After concentrating the reaction solution, the residue was reprecipitated from methanol-ethyl acetate mixed solvent to obtain 57.0 mg of the captioned compound.

The chemical structure, acid addition salts and various spectra data of the Compounds 2 to 11 described in the Reference Examples are shown in Tables 53 to 56 below.

TABLE 53

| Yield (%) | NMR (ppm) (300 MHz CDCl3) | m.p. (° C.) |
|---|---|---|
| Compound 2<br>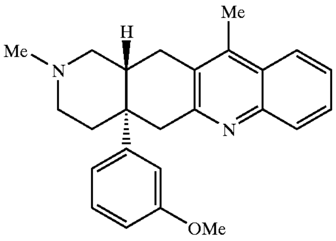 | 2.0(1H, m), 2.16(1H, m), 2.3(1H, m), 2.41(3H, s), 2.51 (3H, s), 2.7(2H, m), 2.82(1H, t, J=11.5Hz), 3.06(3H, m), 3.14(1H, d, J=16.5Hz), 3.68(3H, s), 3.74(1H, d, J=16.5Hz), 6.67(1H, m), 7.06(1H, m), 7.42(1H, m), 7.55(1H, m), 7.9 (2H, m) | Elementary Analysis<br>Composition Formula<br>Calcd.<br>Found<br>IR ($cm^{-1}$) (KBr)<br>2928, 2798, 1607, 1582, 1487, 1431, 1288, 1230<br>Mass (EI) 372 (M+)<br>(data of salt-free compound) |
| Yield (%) | NMR (ppm) (500 MHz, D2O) | m.p.(° C.) |
| Compound 3<br>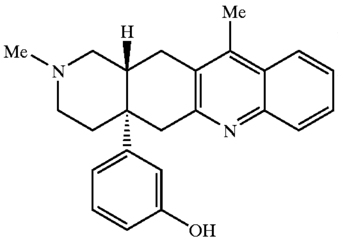 | 2.27(1H, dt, J=14.5, 3.4Hz), 2.68(1H, t, J=11.7Hz), 2.81(3H, s), 2.97(1H, m), 3.3(2H, m), 3.4–3.6(4H, m), 3.68(1H, dd, J=12.7, 3.2Hz), 3.95(1H, d, J=17.0Hz), 6.54(1H, dd, J=8.1, 2.0Hz), 6.95(1H, d, J=7.9Hz), 7.01(1H, m), 7.06(1H, t, J=8.1Hz), 7.83(1H, t, J=7.7Hz), 7.99(1H, t, J=7.7Hz), 8.22 (1H, d, J=8.5Hz), 8.39(1H, d, J=8.7Hz) | Elementary Analysis<br>Composition Formula<br>C24H26N2O/2HCl/0.6H2O<br>Calcd. C: 65.19, H: 6.66, N: 6.33, Cl: 16.03<br>Found C: 65.05, H: 6.90, N: 6.31, Cl: 16.13<br>IR ($cm^{-1}$)<br>Mass (EI) 358 (M+) |

TABLE 54

| Yield (%) | NMR (ppm) (300 MHz, CDCl3) | m.p. (° C.) |
|---|---|---|
| Compound 4<br>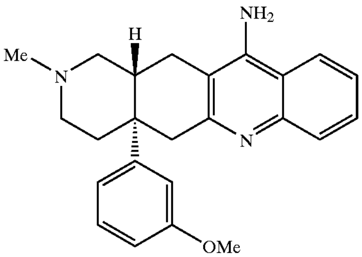 | 2.0(1H, m), 2.1(1H, m), 2.28(1H, m), 2.38(3H, s), 2.6–2.9 (5H, m), 2.97(1H, dd, J=11.0, 3.3Hz), 3.05(1H, d, J=16.5Hz), 3.64(1H, d, J=16.8Hz), 3.67(3H, s), 4.58(2H, brs), 6.58(1H, m), 7.05(3H, m), 7.32(1H, dt, J=7.5, 1.2Hz), 7.51 (1H, dt, J=7.5, 1.2Hz), 7.61(1H, dd, J=8.5, 0.5Hz), 7.82(1H, dd, J=8.5, 0.5Hz) | Elementary Analysis<br>Composition Formula<br>Calcd.<br>Found<br>IR ($cm^{-1}$) (KBr)<br>3058, 2918, 2800, 1651, 1578, 1502, 1439, 1243<br>Mass (EI) 373 (M+) |
| Yield (%) | NMR (ppm) (500 MHz, D2O) | m.p. (° C.) |
| Compound 5<br>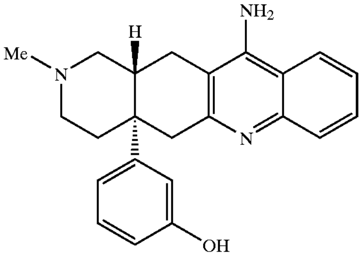 | 2.21 (1H, dt, J=14.5, 2.5Hz) 2.49(1H, d, J=12.5Hz), 2.67(1H, t, J=12.7Hz), 2.84(3H, s), 2.8–2.9(3H, m), 3.17(1H,d, J=16.9Hz), 3.4–3.5(3H, m), 3.60(1H, d, J=10.3Hz), 6.58(2H, m), 6.90(2H, m), 7.09(1H, t, J=8.1Hz), 7.61(1H, d, J=7.3, 1.6Hz), 7.86(2H, m), 8.47(1H, d, J=8.5Hz) | Elementary Analysis<br>Composition Formula<br>Calcd.<br>Found<br>IR ($cm^{-1}$)<br>Mass (EI) 359 (M+) |

TABLE 55

| | NMR (ppm) (300 MHz, CDCl3) | m.p. (° C.) |
|---|---|---|
| Compound 6<br>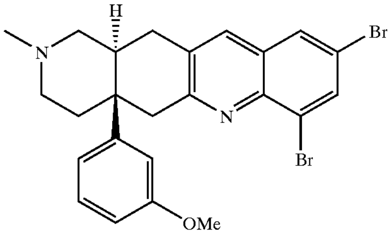 | 2.03–2.09(1H, m), 2.17–2.31(2H, m), 2.40(3H, s), 2.62–2.72 (2H, m), 2.78(1H, t, J=11.5Hz), 3.00(1H, dd, J=2.7, 11.0Hz), 3.08–3.30(3H, m), 3.67(3H, s), 3.83(1H, d, J=16.8Hz), 6.57–6.60(1H, m), 7.03(1H, s), 7.05(1H, s), 7.09(1H, t, J=8.5Hz), 7.58–7.72(2H, brm), 7.92(1H, s) | Elementary Analysis<br>Composition Formula<br>Calcd.<br>Found<br>IR ($cm^{-1}$)<br>Mass |
| Compound 7<br>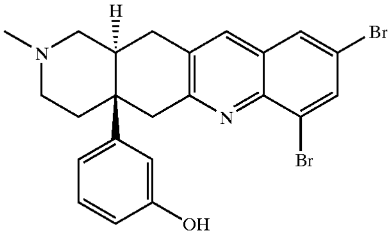 | 2.14(1H, dt, J = 3.6, 14.3Hz), 2.30(1H, d, J=14.6Hz), 2.43(1H, brt, J=11.8Hz), 2.52(3H, s), 2.75–2.84(1H, m), 2.96–3.21(6H, m), 3.76(1H, d, J=17.0Hz), 6.48(1H, td, J=1.6, 8.0Hz), 6.81–6.86(2H, m), 6.93(1H, t, J=7.7Hz), 7.59(1H, s), 7.66 (1H, d, J=2.2Hz), 7.89(1H, t, J=1.1Hz) | Elementary Analysis<br>Composition Formula<br>Calcd.<br>Found<br>IR ($cm^{-1}$)<br>Mass (EI) LR ((M + 2)+)502 |
| | NMR (ppm) (300 MHz, CD3OD) | m.p. (° C.) |
| Compound 8<br>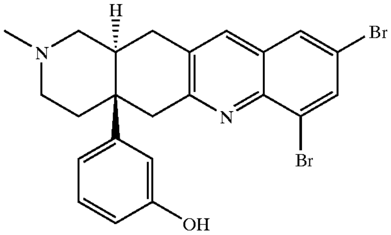<br>dimethanesulfonic acid salt | 2.26–2.30(1H, br), 2.66–2.71(1H, br), 2.71(6H, s), 2.85(1H, t, J=12.6Hz), 2.96(3H, s), 3.38(1H, brd, J=17.3Hz), 3.48–3.58 (3H, brm), 3.66(1H, brt, J=12.9Hz), 3.77(1H, brd, J=12.6Hz), 4.23(1H, brd, J=17.9Hz), 6.59(1H, d, J=8.0Hz), 6.98(1H, brs), 7.03(1H, brd, J=7.7Hz), 7.12(1H, t, J=7.7Hz), 8.18(1H, brs), 8.24(1H, brs), 8.54(1H, brs) | Elementary Analysis<br>Compostion Formula<br>Calcd.<br>Found<br>IR ($cm^{-1}$) (neat)<br>3425, 2529, 1638, 1447<br>Mass |

TABLE 56

| | NMR (ppm) (300 MHz, CDCl3) | m.p. (° C.) |
|---|---|---|
| Compound 9<br>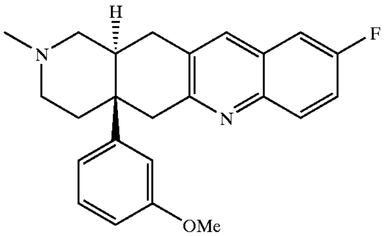 | 1.96(1H, dt, J=3.3, 12.6Hz), 2.10(1H, dt, J=1.9, 12.4Hz), 2.23 (1H, d, J=11.5Hz), 2.33(3H, s), 2.52–2.74(3H, m), 2.90(1H, dd, J=3.8, 11.0Hz), 3.02–3.26(3H, m), 3.63(3H, d, J=0.8Hz), 3.68(1H, d, J=16.5Hz), 6.51–6.57(1H, m), 7.01–7.07(3H, m), 7.16(1H, dd, J=2.7, 9.1Hz), 7.27(1H, dd, J=3.0, 8.5Hz), 7.63 (1H, s), 7.83(1H, dd, J=5.5, 9.3Hz) | Elementary Analysis<br>Composition Formula<br>Calcd.<br>Found<br>IR ($cm^{-1}$)<br>Mass |
| Compound 10<br>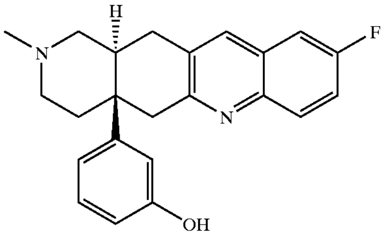 | 1.91–2.00(1H, br), 2.16–2.22(2H, brm), 2.35(3H, s), 2.57–2.65(1H, brm), 2.73(1H, d, J=11.5Hz), 2.85(1H, t, J=11.8Hz), 2.93–3.19(4H, m), 3.58(1H, d, J=16.5Hz), 6.41–6.46(1H, m), 6.82–6.91(3H, m), 7.15(1H, dd, J=2.7, 9.1Hz), 7.20–7.28(1H, m), 7.66(1H, s), 7.73(1H, dd, J=5.2, 9.1Hz) | Elementary Analysis<br>Composition Formula<br>Calcd.<br>Found<br>IR ($cm^{-1}$)<br>Mass (EI) LR (M+)362 |
| | NMR (ppm) (300 MHz, CD3OD) | m.p. (° C.) |

TABLE 56-continued

| | | |
|---|---|---|
| Compound 11<br>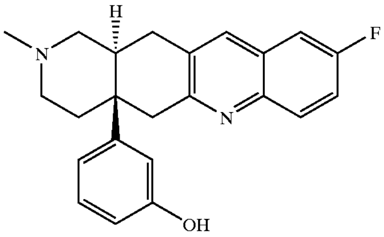<br>ditartaric acid salt | 2.28–2.33(1H, br), 2.52(1H, brd, J=14.8Hz), 2.79–2.88(2H, brm), 2.88(3H, s), 3.17(1H, brd, J=16.2Hz), 3.29–3.69(6H, brm), 4.48(4H, s), 6.53(1H, d, J=6.9Hz), 6.92(1H, s), 6.93 (1H, d, J=6.9Hz), 7.04(1H, t, J=8.0Hz), 7.36–7.42(2H, br), 7.81–7.85(1H, br), 7.90–7.94(1H, br) | Elementary Analysis<br>Composition Formula<br>Calcd.<br>Found<br>IR ($cm^{-1}$)<br>Mass |

Example 1

Evaluation of Activity to Improve Learning and/or Memory Using Morris Water Maze <Experiment Schedule>

In experiments, ICR male mice of 6 weeks old were used. Using Morris water maze as an experiment apparatus, ability of learning and memory of space was evaluated based on the latency until a mouse escapes to a platform arranged in a pool as an index. One trial was maximally 120 seconds, and 1 session was composed of three trials in which each mouse was made to swim in the pool from three different positions. Average time needed for the escape was calculated and evaluation was made based thereon. On the first day (the first session), no drug and nothing were administered. From the second session (Day 2), Compound 1, Compound 8 or a solvent was administered. Trial was repeated for 5 days (5 sessions).

The dose of Compound 1 was 10, 30 or 100 μg/kg, and the dose of Compound 8 was 100 μg/kg. Compound 1, Compound 8 or saline which was the solvent was subcutaneously administered 30 minutes before the first trial of each session. The data was subjected to analysis of variance and significance was evaluated according to Fisher's PLSD test. The cases where $P<0.05$ was evaluated as significant.

<Evaluation of Compound 1>

No difference in the time period required for escaping to the platform between the groups was observed in Session 1. With proceeding of the sessions, the time period required for the escaping to the platform was shortened in the group to which physiological saline was administered. On the other hand, as shown in FIG. 1, by administration of Compound 1, the time period required for the escaping to the platform was shortened dose-dependently from the second session, so that clear improvement in the ability of learning and memory of space was observed.

FIG. 1 shows the comparison between the learning process of the rats to which Compound 1 was administered and that of the rats to which saline was administered. In the graph, the ordinate indicates latency for reaching the plat form (and SE), and abscissa indicates the number of sessions (* means $P<0.05$, and ** means $P<0.01$). It was shown that ability of learning and memory of space was improved in the Morris water maze test by administration of Compound 1.

<Evaluation of Compound 8>

Figure 3:
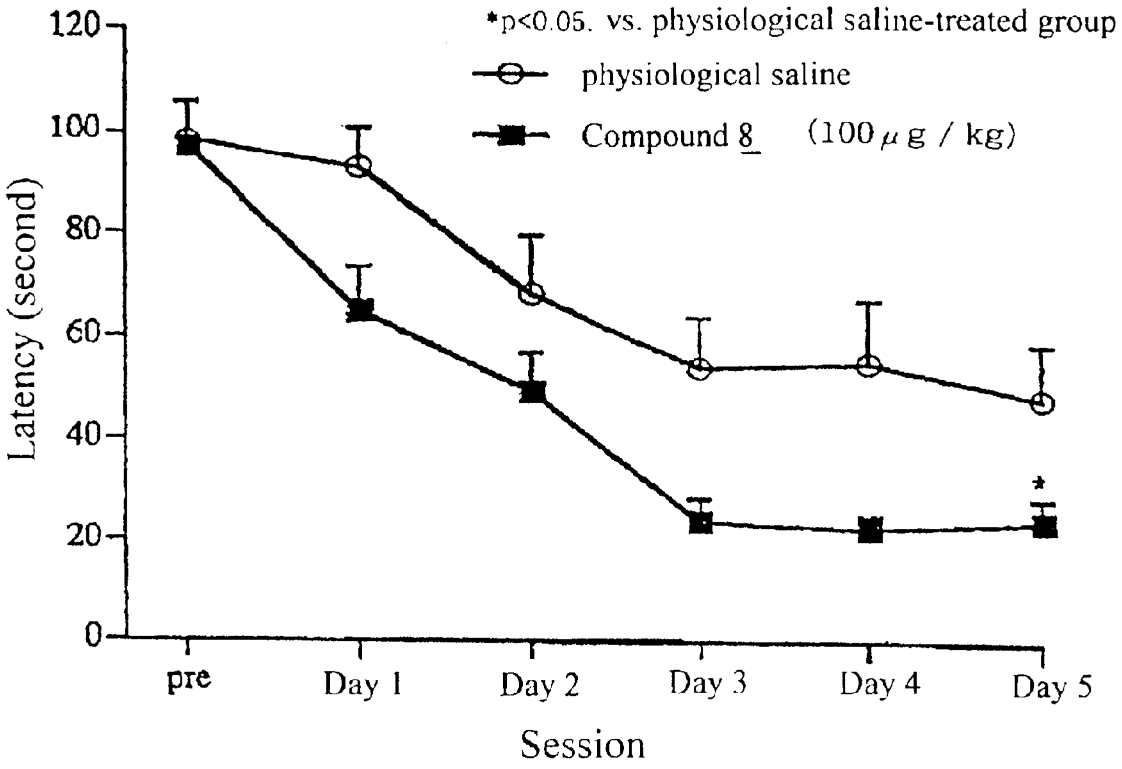
FIG. 3 shows the learning process of the rats to which Compound 8 that is the agent for improving learning and/or memory according to the present invention, in comparison with the learning process of the rats to which saline was administered.

Similar to the evaluation of Compound 1, the latency required for escaping to the platform by mice was shortened by administration of Compound 8, and clear improvement in the ability of learning and memory of space was observed. FIG. 3 shows the comparison between the learning process of the rats to which Compound 8 was administered and that of the rats to which saline was administered.

Example 2

Effect for Improvement of Learning in Test of Learning of Step-Down Type Passive Avoidance <Experiment Schedule>

In experiments, ICR male mice of 6 weeks old were used. The experiment apparatus comprised a plastic box sizing 25×25×30 cm (width×depth×height), a stainless steel grid for giving electrical shock, which was laid on the floor of the box, and a wooden platform sizing 4.5×4.5×3.0 cm (width×depth×height) placed on a corner on the floor grid.

Sixty minutes before the training trial, 100 or 300 μg/kg of Compound 1, or its solvent, saline, was subcutaneously administered. Thirty minutes later, 0.1 mg/kg of MK-801 which is a non-competitive antagonist of NMDA receptor, which is a compound that causes learning disability and/or memory disorder was intraperitoneally administered. Training trial was carried out by placing a mouse on the platform, and the time period until the mouse stepped down to the floor grid, that is, the Step-Down latency, was measured. Simultaneously with the attaching all of the feet of the mouse to the floor, an electrical shock of 0.6 mA was given for 2 seconds, thereby making the mouse to learn that an electrical shock would be given if the mouse would stepped down to the floor. Only the mice which showed the Step-Down latency of 3 to 30 seconds in the training trials were used in the test trials.

Test trials were carried out 24 hours after the training trials. Each mouse was again placed on the platform, and the Step-Down latency was measured for maximally 300 seconds.

<Evaluation of Compound 1>

Figure 2:
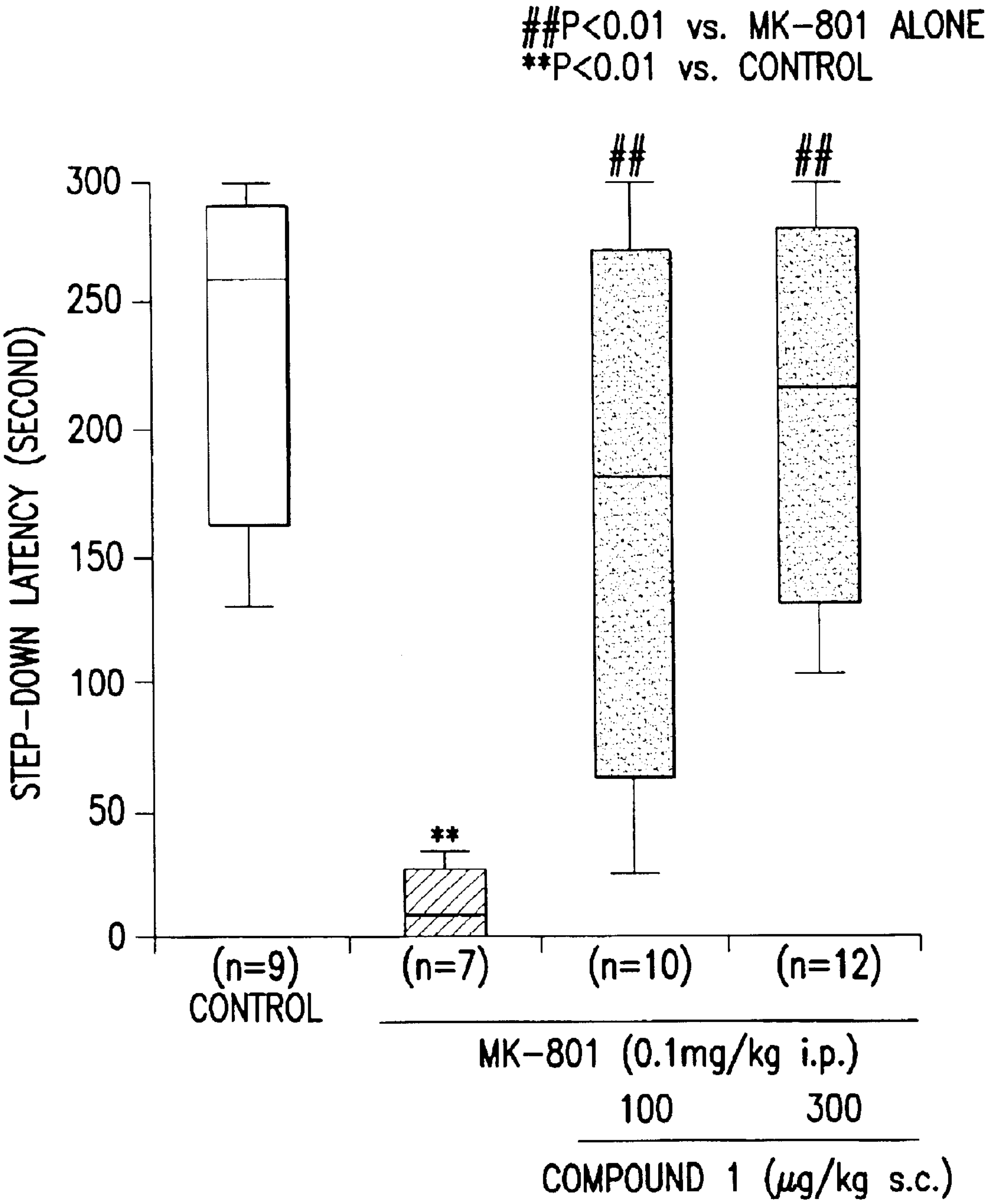
FIG. 2 shows the Step-Down latency of the group of mice to which MK-801 that is a compound inducing learning disability and memory disorder was administered and then Compound 1 which is the agent for improving learning and/or memory according to the present invention was administered, in comparison with the Step-Down latency of the group to which the solvent alone was administered and the Step-Down latency of the group to which MK-801 alone was administered.

The results are shown in FIG. 2. In the control group to which the solvent alone was administered, the Step-Down latency in the test trials was extended than that in the training trials, so that it was shown that the mice memorized that electrical shock was given when they stepped down to the floor. On the other hand, in the group to which MK-801 alone was administered, the Step-Down latency was significantly shorter than that of the control group, so that learning disability and memory disorder were induced. The action of shortening the Step-Down latency by MK-801 was significantly reduced by administration of Compound 1, so that it was observed that Compound 1 exhibited activity to improve the learning disability and memory disorder induced by MK-801.

FIG. 2 shows the Step-Down latency of the control group to which solvent alone was administered, the groups to which MK-801 was administered and of the groups to which Compound 1 was administered (the bar in each column is the median). In the group to which MK-801 was administered, the passive avoidance reaction was significantly suppressed when compared with the control group. This suppressant was recovered by administration of Compound 1, so that it was shown that Compound 1 had an activity to improve the learning disability and memory disorder induced by MK-801 (** means P<0.01 vs. the control, and ## means P<0.01 vs. the group to which MK-801 alone was administered).

Industrial Availability

The agent for improving learning and/or memory according to the present invention is useful for the therapy of dementia accompanying disorder of memory due to a cerebrovascular disease, neurodegererative disease such as Alzheimer's disease, endocrine disease, nutritional or metabolic disorder, infectious disease, drug addiction or the like.

What is claimed is:

1. A method for improving learning and/or memory in a subject which comprises administering to the subject an effective amount of an isoquinoline (I)

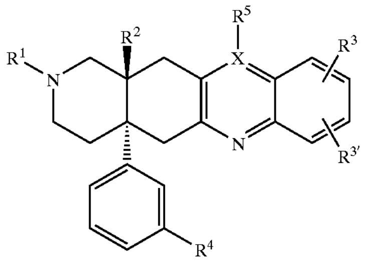

derivative of the Formula (I):

wherein $R^1$ represents hydrogen, $C_1$–$C_5$ alkyl, $C_4$–$C_7$ cycloalkylalkyl, $C_5$–$C_7$ cycloalkenylalkyl, $C_7$–$C_{14}$ aralkyl, $C_4$–$C_5$ transalkenyl, allyl, furanyl-2-ylalkyl, thienyl-2-ylalkyl, $C_1$–$C_5$ alkanoyl, benzoyl, vinyloxycarbonyl, trichloroethoxycarbonyl, benzyloxycarbonyl or $C_8$–$C_{14}$ arylalkanoyl; $R^2$ represents hydrogen or $OR^6$ (wherein $R^6$ represents hydrogen, $C_1$–$C_5$ alkyl or $C_1$–$C_5$ alkanoyl); $R^3$ and $R^{3'}$ independently represent $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino, or $C_1$–$C_3$ alkylamino; $R^4$ represents hydrogen, hydroxy, $C_1$–$C_3$ alkoxy, benzyl, or $C_1$–$C_5$ alkanoyl or halogen; X represents nitrogen or carbon; $R^5$ exists only when X is carbon, and represents $C_1$–$C_5$ alkyl, hydrogen, chlorine, fluorine, bromine, iodine, trifluoromethyl, cyano, hydroxy, $C_1$–$C_3$ alkoxycarbonyl, $C_1$–$C_3$ alkylcarbonylamino, $C_1$–$C_5$ alkoxy, nitro, amino or $C_1$–$C_3$ alkylamino or a pharmaceutically acceptable salt thereof.

2. The method for improving learning and/or memory according to claim 1, wherein in Formula (I), $R^1$ is hydrogen, methyl, ethyl, cyclopropylmethyl, allyl, phenethyl, furan-2-ylethyl or thiophene-2-ylethyl; $R^2$ is hydrogen, hydroxy, methoxy or ethoxy; $R^3$ and $R^{3'}$ independently are methyl, hydrogen, chlorine, fluorine, bromine, iodine, hydroxy, methoxy, nitro, amino or dimethylamino; $R^4$ is hydrogen, hydroxy or methoxy; X is carbon; $R^5$ is methyl, hydrogen, chlorine, fluorine, bromine, iodine, hydroxy, methoxy, nitro, amino or dimethylamino.

* * * * *